United States Patent
Shelton, IV

(10) Patent No.: US 11,853,835 B2
(45) Date of Patent: Dec. 26, 2023

(54) RFID IDENTIFICATION SYSTEMS FOR SURGICAL INSTRUMENTS

(71) Applicant: Cilag GmbH International, Zug (CH)

(72) Inventor: Frederick E. Shelton, IV, Hillsboro, OH (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 16/458,122

(22) Filed: Jun. 30, 2019

(65) Prior Publication Data

US 2020/0410177 A1    Dec. 31, 2020

Related U.S. Application Data

(60) Provisional application No. 62/868,457, filed on Jun. 28, 2019.

(51) Int. Cl.
| | |
|---|---|
| *G06K 7/08* | (2006.01) |
| *G06K 7/10* | (2006.01) |
| *A61B 90/98* | (2016.01) |
| *A61B 17/10* | (2006.01) |
| *G06K 19/07* | (2006.01) |
| *A61B 17/29* | (2006.01) |

(52) U.S. Cl.
CPC .......... *G06K 7/10366* (2013.01); *A61B 17/10* (2013.01); *A61B 90/98* (2016.02); *G06K 19/0723* (2013.01); *A61B 2017/2946* (2013.01)

(58) Field of Classification Search
CPC ........ G06K 7/00; G06K 7/08; G06K 17/0022; G06K 17/0025
USPC ...................... 235/451, 380, 462, 46, 472.02
See application file for complete search history.

(56) References Cited

U.S. PATENT DOCUMENTS

| | | |
|---|---|---|
| 903,739 A | 11/1908 | Lesemann |
| 1,075,556 A | 10/1913 | Fenoughty |
| 1,082,105 A | 12/1913 | Anderson |

(Continued)

FOREIGN PATENT DOCUMENTS

| | | |
|---|---|---|
| AU | 2012268848 A1 | 1/2013 |
| CN | 2785249 Y | 5/2006 |

(Continued)

OTHER PUBLICATIONS

IEEE Std 802.3-2012 (Revision of IEEE Std 802.3-2008, published Dec. 28, 2012.

(Continued)

*Primary Examiner* — Daniel St Cyr

(57) ABSTRACT

A surgical device for applying clips is disclosed including a cartridge, an RFID tag, and a controller. The cartridge includes a plurality of clips. A crimping drive is configured to move a first jaw and a second jaw to a closed position during a crimping stroke. One of the plurality of clips is crimped around tissue during the crimping stroke. Stored data on the RFID tag relates to an identifying characteristic of at least one of the plurality of clips within the cartridge. An RFID scanner is configured to receive a first signal from the RFID tag in response to an interrogation signal. The first signal includes the stored data on the RFID tag. A controller in communication with the RFID scanner is configured to compare the stored data to a set of compatibility data and vary an operational parameter of the surgical device based on the stored data.

22 Claims, 26 Drawing Sheets

(56) References Cited

U.S. PATENT DOCUMENTS

| | | |
|---|---|---|
| 1,466,128 A | 8/1923 | Hallenbeck |
| 2,120,951 A | 6/1938 | Hodgman |
| 2,224,108 A | 12/1940 | Ridgway |
| 2,420,552 A | 5/1947 | Morrill |
| 2,491,872 A | 12/1949 | Neuman |
| 2,724,289 A | 11/1955 | Wight |
| 2,825,178 A | 3/1958 | Hawkins |
| 3,026,744 A | 3/1962 | Rouse |
| 3,035,256 A | 5/1962 | Egbert |
| 3,315,863 A | 4/1967 | O'Dea |
| 3,604,561 A | 9/1971 | Mallina et al. |
| 3,635,394 A | 1/1972 | Natelson |
| 3,661,339 A | 5/1972 | Shimizu |
| 3,685,250 A | 8/1972 | Henry et al. |
| 3,724,237 A | 4/1973 | Wood |
| 3,887,393 A | 6/1975 | La Rue, Jr. |
| 3,973,179 A | 8/1976 | Weber et al. |
| 3,999,110 A | 12/1976 | Ramstrom et al. |
| 4,149,461 A | 4/1979 | Simeth |
| 4,160,857 A | 7/1979 | Nardella et al. |
| 4,203,444 A | 5/1980 | Bonnell et al. |
| 4,389,963 A | 6/1983 | Pearson |
| 4,421,264 A | 12/1983 | Arter et al. |
| 4,425,915 A | 1/1984 | Ivanov |
| 4,476,864 A | 10/1984 | Tezel |
| 4,481,458 A | 11/1984 | Lane |
| 4,514,477 A | 4/1985 | Kobayashi |
| 4,608,980 A | 9/1986 | Aihara |
| 4,624,401 A | 11/1986 | Gassner et al. |
| 4,642,738 A | 2/1987 | Meller |
| 4,827,552 A | 5/1989 | Bojar et al. |
| 4,868,958 A | 9/1989 | Suzuki et al. |
| 4,962,681 A | 10/1990 | Yang |
| 4,976,173 A | 12/1990 | Yang |
| 5,009,222 A | 4/1991 | Her |
| 5,033,552 A | 7/1991 | Hu |
| 5,056,953 A | 10/1991 | Marot et al. |
| 5,100,422 A | 3/1992 | Berguer et al. |
| 5,164,652 A | 11/1992 | Johnson et al. |
| 5,269,794 A | 12/1993 | Rexroth |
| 5,281,400 A | 1/1994 | Berry, Jr. |
| 5,291,133 A | 3/1994 | Gokhale et al. |
| 5,302,148 A | 4/1994 | Heinz |
| 5,303,606 A | 4/1994 | Kokinda |
| 5,308,353 A | 5/1994 | Beurrier |
| 5,308,358 A | 5/1994 | Bond et al. |
| 5,330,486 A | 7/1994 | Wilk |
| 5,350,104 A | 9/1994 | Main et al. |
| 5,389,072 A | 2/1995 | Imran |
| 5,431,645 A | 7/1995 | Smith et al. |
| 5,474,738 A | 12/1995 | Nichols et al. |
| 5,487,377 A | 1/1996 | Smith et al. |
| 5,507,773 A | 4/1996 | Huitema et al. |
| 5,509,918 A | 4/1996 | Romano |
| 5,607,436 A | 3/1997 | Pratt et al. |
| 5,626,979 A | 5/1997 | Mitsui et al. |
| 5,637,110 A | 6/1997 | Pennybacker et al. |
| 5,656,917 A | 8/1997 | Theobald |
| 5,664,404 A | 9/1997 | Ivanov et al. |
| 5,715,836 A | 2/1998 | Kliegis et al. |
| 5,716,352 A | 2/1998 | Viola et al. |
| 5,732,712 A | 3/1998 | Adair |
| 5,736,271 A | 4/1998 | Cisar et al. |
| 5,755,726 A | 5/1998 | Pratt et al. |
| 5,762,458 A | 6/1998 | Wang et al. |
| 5,766,186 A | 6/1998 | Faraz et al. |
| 5,769,640 A | 6/1998 | Jacobus et al. |
| 5,772,099 A | 6/1998 | Gravener |
| 5,807,241 A | 9/1998 | Heimberger |
| 5,868,664 A | 2/1999 | Speier et al. |
| 5,881,943 A | 3/1999 | Heck et al. |
| 5,907,664 A | 5/1999 | Wang et al. |
| 6,013,991 A | 1/2000 | Philipp |
| 6,019,780 A | 2/2000 | Lombardo et al. |
| 6,039,126 A | 3/2000 | Hsieh |
| 6,090,123 A | 7/2000 | Culp et al. |
| 6,094,021 A | 7/2000 | Noro et al. |
| RE36,923 E | 10/2000 | Hiroi et al. |
| 6,317,616 B1 | 11/2001 | Glossop |
| 6,361,542 B1 | 3/2002 | Dimitriu et al. |
| 6,364,828 B1 | 4/2002 | Yeung et al. |
| 6,402,780 B1 | 6/2002 | Williamson, IV et al. |
| 6,457,338 B1 | 10/2002 | Frenken |
| 6,482,063 B1 | 11/2002 | Frigard |
| 6,500,189 B1 | 12/2002 | Lang et al. |
| 6,506,399 B2 | 1/2003 | Donovan |
| 6,554,844 B2 | 4/2003 | Lee et al. |
| 6,572,629 B2 | 6/2003 | Kalloo et al. |
| 6,595,914 B2 | 7/2003 | Kato |
| 6,626,938 B1 | 9/2003 | Butaric et al. |
| 6,726,705 B2 | 4/2004 | Peterson et al. |
| 6,755,825 B2 | 6/2004 | Shoenman et al. |
| 6,801,009 B2 | 10/2004 | Makaran et al. |
| 6,887,244 B1 | 5/2005 | Walker et al. |
| 6,949,196 B2 | 9/2005 | Schmitz et al. |
| 7,021,399 B2 | 4/2006 | Driessen |
| 7,038,421 B2 | 5/2006 | Trifilo |
| 7,081,318 B2 | 7/2006 | Lee et al. |
| 7,197,965 B1 | 4/2007 | Anderson |
| 7,205,959 B2 | 4/2007 | Henriksson |
| 7,226,467 B2 | 6/2007 | Lucatero et al. |
| 7,336,183 B2 | 2/2008 | Reddy et al. |
| 7,354,398 B2 | 4/2008 | Kanazawa |
| 7,367,973 B2 | 5/2008 | Manzo et al. |
| 7,492,261 B2 | 2/2009 | Cambre et al. |
| 7,497,137 B2 | 3/2009 | Tellenbach et al. |
| 7,605,826 B2 | 10/2009 | Sauer |
| 7,618,427 B2 | 11/2009 | Ortiz et al. |
| 7,625,662 B2 | 12/2009 | Vaisnys et al. |
| 7,706,853 B2 | 4/2010 | Hacker et al. |
| 7,709,136 B2 | 5/2010 | Touchton et al. |
| 7,735,704 B2 | 6/2010 | Bilotti |
| 7,779,614 B1 | 8/2010 | McGonagle et al. |
| 7,782,382 B2 | 8/2010 | Fujimura |
| 7,819,894 B2 | 10/2010 | Mitsuishi et al. |
| 7,829,416 B2 | 11/2010 | Kudou et al. |
| 7,845,912 B2 | 12/2010 | Sung et al. |
| 7,887,755 B2 | 2/2011 | Mingerink et al. |
| 7,942,300 B2 | 5/2011 | Rethy et al. |
| 7,948,381 B2 | 5/2011 | Lindsay et al. |
| 7,976,508 B2 | 7/2011 | Hoag |
| 7,981,025 B2 | 7/2011 | Pool et al. |
| 8,028,835 B2 | 10/2011 | Yasuda et al. |
| 8,038,044 B2 | 10/2011 | Viola |
| 8,114,345 B2 | 2/2012 | Dlugos, Jr. et al. |
| 8,157,834 B2 | 4/2012 | Conlon |
| 8,207,863 B2 | 6/2012 | Neubauer et al. |
| 8,235,274 B2 | 8/2012 | Cappola |
| 8,327,514 B2 | 12/2012 | Kim |
| 8,328,065 B2 | 12/2012 | Shah |
| 8,377,059 B2 | 2/2013 | Deville et al. |
| 8,400,108 B2 | 3/2013 | Powell et al. |
| 8,439,830 B2 | 5/2013 | McKinley et al. |
| 8,486,047 B2 | 7/2013 | Stopek |
| 8,499,966 B2 * | 8/2013 | Palmer ............... A61J 7/0038 221/232 |
| 8,499,994 B2 | 8/2013 | D'Arcangelo |
| 8,517,938 B2 | 8/2013 | Eisenhardt et al. |
| 8,523,882 B2 | 9/2013 | Huitema et al. |
| 8,529,599 B2 | 9/2013 | Holsten |
| 8,585,598 B2 | 11/2013 | Razzaque et al. |
| 8,591,400 B2 | 11/2013 | Sugiyama |
| 8,613,384 B2 | 12/2013 | Pastorelli et al. |
| 8,617,155 B2 | 12/2013 | Johnson et al. |
| 8,620,473 B2 | 12/2013 | Diolaiti et al. |
| 8,628,467 B2 | 1/2014 | Whitman et al. |
| 8,656,929 B2 | 2/2014 | Miller et al. |
| 8,672,209 B2 | 3/2014 | Crainich |
| 8,709,012 B2 | 4/2014 | Muller |
| 8,795,159 B2 | 8/2014 | Moriyama |
| 8,828,046 B2 | 9/2014 | Stefanchik et al. |
| 8,851,355 B2 | 10/2014 | Aranyi et al. |
| 8,858,547 B2 | 10/2014 | Brogna |
| 8,869,912 B2 | 10/2014 | Ro.beta.kamp et al. |

(56) References Cited

U.S. PATENT DOCUMENTS

| | | |
|---|---|---|
| 8,869,913 B2 | 10/2014 | Matthias et al. |
| 8,876,698 B2 | 11/2014 | Sakamoto et al. |
| 8,882,660 B2 | 11/2014 | Phee et al. |
| 8,882,792 B2 | 11/2014 | Dietz et al. |
| 8,884,560 B2 | 11/2014 | Ito |
| 8,910,847 B2 | 12/2014 | Nalagatla et al. |
| 8,915,842 B2 | 12/2014 | Weisenburgh, II et al. |
| 8,931,692 B2 | 1/2015 | Sancak |
| 8,939,898 B2 | 1/2015 | Omoto |
| 8,945,098 B2 | 2/2015 | Seibold et al. |
| 8,961,542 B2 | 2/2015 | Whitfield et al. |
| 8,984,711 B2 | 3/2015 | Ota et al. |
| 9,004,799 B1 | 4/2015 | Tibbits |
| 9,014,856 B2 | 4/2015 | Manzo et al. |
| 9,017,849 B2 | 4/2015 | Stulen et al. |
| 9,017,851 B2 | 4/2015 | Felder et al. |
| 9,028,468 B2 | 5/2015 | Scarfogliero et al. |
| 9,040,062 B2 | 5/2015 | Maeda et al. |
| 9,044,238 B2 | 6/2015 | Orszulak |
| 9,050,089 B2 | 6/2015 | Orszulak |
| 9,070,068 B2 | 6/2015 | Coveley et al. |
| 9,084,586 B2 | 7/2015 | Hafner et al. |
| 9,099,922 B2 | 8/2015 | Toosky et al. |
| 9,101,359 B2 | 8/2015 | Smith et al. |
| 9,167,960 B2 | 10/2015 | Yamaguchi et al. |
| 9,171,244 B2 | 10/2015 | Endou et al. |
| 9,179,832 B2 | 11/2015 | Diolaiti |
| 9,192,376 B2 | 11/2015 | Almodovar |
| D746,459 S | 12/2015 | Kaercher et al. |
| 9,220,504 B2 | 12/2015 | Viola et al. |
| 9,226,760 B2 | 1/2016 | Shelton, IV |
| 9,226,799 B2 | 1/2016 | Lightcap et al. |
| 9,241,758 B2 | 1/2016 | Franer et al. |
| 9,265,510 B2 | 2/2016 | Dietzel et al. |
| 9,301,811 B2 | 4/2016 | Goldberg et al. |
| 9,314,291 B2 | 4/2016 | Schall et al. |
| 9,339,342 B2 | 5/2016 | Prisco et al. |
| 9,352,071 B2 | 5/2016 | Landgrebe et al. |
| 9,358,065 B2 | 6/2016 | Ladtkow et al. |
| 9,364,223 B2 | 6/2016 | Scirica |
| 9,370,361 B2 | 6/2016 | Viola et al. |
| 9,385,640 B2 | 7/2016 | Sun et al. |
| 9,392,885 B2 | 7/2016 | Vogler et al. |
| 9,393,354 B2 | 7/2016 | Freedman et al. |
| 9,396,369 B1 | 7/2016 | Whitehurst et al. |
| 9,398,905 B2 | 7/2016 | Martin |
| 9,402,688 B2 | 8/2016 | Min et al. |
| 9,408,605 B1 | 8/2016 | Knodel et al. |
| 9,421,682 B2 | 8/2016 | McClaskey et al. |
| 9,429,204 B2 | 8/2016 | Stefan et al. |
| 9,463,012 B2 | 10/2016 | Bonutti et al. |
| 9,474,513 B2 | 10/2016 | Ishida et al. |
| 9,486,215 B2 | 11/2016 | Olson et al. |
| 9,492,172 B2 | 11/2016 | Weisshaupt et al. |
| 9,504,520 B2 | 11/2016 | Worrell et al. |
| 9,504,528 B2 | 11/2016 | Ivinson et al. |
| 9,507,399 B2 | 11/2016 | Chien |
| 9,517,065 B2 | 12/2016 | Simms et al. |
| 9,522,014 B2 | 12/2016 | Nishizawa et al. |
| 9,526,921 B2 | 12/2016 | Kimball et al. |
| 9,549,733 B2 | 1/2017 | Knodel |
| 9,549,750 B2 | 1/2017 | Shelton, IV et al. |
| 9,554,803 B2 | 1/2017 | Smith et al. |
| 9,561,072 B2 | 2/2017 | Ko |
| 9,610,412 B2 | 4/2017 | Zemlok et al. |
| 9,629,631 B2 | 4/2017 | Nicholas et al. |
| 9,636,112 B2 | 5/2017 | Penna et al. |
| 9,642,642 B2 | 5/2017 | Lim |
| 9,661,991 B2 | 5/2017 | Glossop |
| 9,675,348 B2 | 6/2017 | Smith et al. |
| 9,700,315 B2 | 7/2017 | Chen et al. |
| 9,700,334 B2 | 7/2017 | Hinman et al. |
| 9,702,823 B2 | 7/2017 | Maher et al. |
| 9,730,697 B2 * | 8/2017 | Morgan ............ A61B 17/07207 |
| 9,730,757 B2 | 8/2017 | Brudniok |
| 9,737,298 B2 | 8/2017 | Isbell, Jr. |
| 9,750,503 B2 | 9/2017 | Milliman |
| 9,815,118 B1 | 11/2017 | Schmitt et al. |
| 9,833,235 B2 | 12/2017 | Penna et al. |
| 9,839,481 B2 | 12/2017 | Blumenkranz et al. |
| 9,867,617 B2 | 1/2018 | Ma |
| 9,877,722 B2 | 1/2018 | Schellin et al. |
| 9,888,914 B2 | 2/2018 | Martin et al. |
| 9,907,552 B2 | 3/2018 | Measamer et al. |
| 9,924,943 B2 | 3/2018 | Mohan Pinjala et al. |
| 9,936,952 B2 | 4/2018 | Demmy |
| 9,949,754 B2 | 4/2018 | Newhauser et al. |
| 9,956,677 B2 | 5/2018 | Baskar et al. |
| 9,987,008 B2 | 6/2018 | Scirica et al. |
| 9,993,284 B2 | 6/2018 | Boudreaux |
| 10,010,395 B2 | 7/2018 | Puckett et al. |
| 10,022,120 B2 | 7/2018 | Martin et al. |
| 10,022,123 B2 | 7/2018 | Williams et al. |
| 10,045,869 B2 | 8/2018 | Forsell |
| 10,064,622 B2 | 9/2018 | Murthy Aravalli |
| 10,080,552 B2 | 9/2018 | Nicholas et al. |
| D830,550 S | 10/2018 | Miller et al. |
| 10,105,126 B2 | 10/2018 | Sauer |
| 10,105,149 B2 | 10/2018 | Haider et al. |
| 10,111,658 B2 | 10/2018 | Chowaniec et al. |
| 10,111,665 B2 | 10/2018 | Aranyi et al. |
| D833,608 S | 11/2018 | Miller et al. |
| 10,123,845 B2 | 11/2018 | Yeung |
| 10,130,382 B2 | 11/2018 | Gladstone |
| 10,152,789 B2 | 12/2018 | Carnes et al. |
| 10,161,816 B2 | 12/2018 | Jackson et al. |
| 10,164,466 B2 | 12/2018 | Calderoni |
| 10,172,618 B2 | 1/2019 | Shelton, IV et al. |
| 10,172,669 B2 | 1/2019 | Felder et al. |
| 10,182,868 B2 | 1/2019 | Meier et al. |
| 10,188,389 B2 | 1/2019 | Vendely et al. |
| 10,190,888 B2 | 1/2019 | Hryb et al. |
| 10,213,204 B2 | 2/2019 | Aranyi et al. |
| 10,271,840 B2 | 4/2019 | Sapre |
| 10,285,700 B2 | 5/2019 | Scheib |
| 10,303,851 B2 | 5/2019 | Nguyen et al. |
| 10,314,578 B2 | 6/2019 | Leimbach et al. |
| 10,314,580 B2 | 6/2019 | Scheib et al. |
| 10,349,937 B2 | 7/2019 | Williams |
| 10,404,136 B2 | 9/2019 | Oktavec et al. |
| 10,413,155 B2 | 9/2019 | Inoue |
| 10,420,551 B2 | 9/2019 | Calderoni |
| D865,174 S | 10/2019 | Auld et al. |
| D865,175 S | 10/2019 | Widenhouse et al. |
| 10,426,555 B2 | 10/2019 | Crowley et al. |
| 10,463,371 B2 | 11/2019 | Kostrzewski |
| 10,478,185 B2 | 11/2019 | Nicholas |
| 10,478,187 B2 | 11/2019 | Shelton, IV et al. |
| 10,482,292 B2 | 11/2019 | Clouser et al. |
| 10,499,917 B2 | 12/2019 | Scheib et al. |
| 10,500,000 B2 | 12/2019 | Swayze et al. |
| 10,508,720 B2 | 12/2019 | Nicholas |
| 10,542,976 B2 | 1/2020 | Calderoni et al. |
| 10,548,593 B2 | 2/2020 | Shelton, IV et al. |
| 10,561,419 B2 | 2/2020 | Beardsley |
| 10,568,493 B2 | 2/2020 | Blase et al. |
| 10,588,231 B2 | 3/2020 | Sgroi, Jr. et al. |
| 10,603,041 B2 | 3/2020 | Miller et al. |
| 10,610,346 B2 | 4/2020 | Schwartz |
| 10,624,709 B2 | 4/2020 | Remm |
| 10,625,062 B2 | 4/2020 | Matlock et al. |
| 10,631,858 B2 | 4/2020 | Burbank |
| 10,631,860 B2 | 4/2020 | Bakos et al. |
| 10,645,905 B2 | 5/2020 | Gandola et al. |
| 10,646,292 B2 | 5/2020 | Solomon et al. |
| 10,667,408 B2 | 5/2020 | Sgroi, Jr. et al. |
| D888,953 S | 6/2020 | Baxter, III et al. |
| 10,667,818 B2 | 6/2020 | McLain et al. |
| 10,674,895 B2 | 6/2020 | Yeung et al. |
| 10,675,102 B2 | 6/2020 | Forgione et al. |
| 10,687,819 B2 | 6/2020 | Stokes et al. |
| D893,717 S | 8/2020 | Messerly et al. |
| 10,736,616 B2 | 8/2020 | Scheib et al. |
| 10,772,628 B2 | 9/2020 | Chen et al. |

(56) References Cited

U.S. PATENT DOCUMENTS

| | | |
|---|---|---|
| 10,772,651 B2 | 9/2020 | Shelton, IV et al. |
| 10,806,451 B2 | 10/2020 | Harris et al. |
| 10,813,683 B2 | 10/2020 | Baxter, III et al. |
| 10,842,473 B2 | 11/2020 | Scheib et al. |
| D904,612 S | 12/2020 | Wynn et al. |
| D906,355 S | 12/2020 | Messerly et al. |
| 10,849,621 B2 | 12/2020 | Whitfield et al. |
| 10,849,623 B2 | 12/2020 | Dunki-Jacobs et al. |
| 10,849,697 B2 | 12/2020 | Yates et al. |
| 10,874,392 B2 | 12/2020 | Scirica et al. |
| 10,874,393 B2 | 12/2020 | Satti, III et al. |
| D907,647 S | 1/2021 | Siebel et al. |
| D907,648 S | 1/2021 | Siebel et al. |
| D908,216 S | 1/2021 | Messerly et al. |
| 10,892,899 B2 | 1/2021 | Shelton, IV et al. |
| D910,847 S | 2/2021 | Shelton, IV et al. |
| 10,919,156 B2 | 2/2021 | Roberts et al. |
| D914,878 S | 3/2021 | Shelton, IV et al. |
| 10,932,804 B2 | 3/2021 | Scheib et al. |
| 10,932,872 B2 | 3/2021 | Shelton, IV et al. |
| 10,944,728 B2 | 3/2021 | Wiener et al. |
| 10,952,708 B2 | 3/2021 | Scheib et al. |
| D917,500 S | 4/2021 | Siebel et al. |
| 10,966,791 B2 | 4/2021 | Harris et al. |
| 10,973,520 B2 | 4/2021 | Shelton, IV et al. |
| 10,987,178 B2 | 4/2021 | Shelton, IV et al. |
| 11,013,563 B2 | 5/2021 | Shelton, IV et al. |
| 11,020,016 B2 | 6/2021 | Wallace et al. |
| 11,026,751 B2 | 6/2021 | Shelton, IV et al. |
| 11,051,807 B2 | 7/2021 | Shelton, IV et al. |
| 11,058,498 B2 | 7/2021 | Shelton, IV et al. |
| 11,069,012 B2 | 7/2021 | Shelton, IV et al. |
| 11,076,921 B2 | 8/2021 | Shelton, IV et al. |
| 11,090,047 B2 | 8/2021 | Shelton, IV et al. |
| 11,096,688 B2 | 8/2021 | Shelton, IV et al. |
| 11,100,631 B2 | 8/2021 | Yates et al. |
| 11,116,485 B2 | 9/2021 | Scheib et al. |
| 11,123,069 B2 | 9/2021 | Baxter, III et al. |
| 11,129,634 B2 | 9/2021 | Scheib et al. |
| 11,132,462 B2 | 9/2021 | Shelton, IV et al. |
| 11,166,716 B2 | 11/2021 | Shelton, IV et al. |
| 11,166,772 B2 | 11/2021 | Shelton, IV et al. |
| 11,179,208 B2 | 11/2021 | Yates et al. |
| 11,197,668 B2 | 12/2021 | Shelton, IV et al. |
| 11,202,570 B2 | 12/2021 | Shelton, IV et al. |
| 11,202,633 B2 | 12/2021 | Harris et al. |
| 11,207,067 B2 | 12/2021 | Shelton, IV et al. |
| 11,207,146 B2 | 12/2021 | Shelton, IV et al. |
| 11,213,294 B2 | 1/2022 | Shelton, IV et al. |
| 11,213,359 B2 | 1/2022 | Shelton, IV et al. |
| 11,219,453 B2 | 1/2022 | Shelton, IV et al. |
| 11,219,455 B2 | 1/2022 | Shelton, IV et al. |
| 11,229,437 B2 | 1/2022 | Shelton, IV et al. |
| 2002/0023126 A1 | 2/2002 | Flavin |
| 2002/0138086 A1 | 9/2002 | Sixto et al. |
| 2002/0177848 A1 | 11/2002 | Truckai et al. |
| 2003/0047230 A1 | 3/2003 | Kim |
| 2003/0050654 A1 | 3/2003 | Whitman et al. |
| 2003/0163029 A1 | 8/2003 | Sonnenschein et al. |
| 2004/0034287 A1 | 2/2004 | Hickle |
| 2004/0093020 A1 | 5/2004 | Sinton |
| 2004/0239582 A1 | 12/2004 | Seymour |
| 2005/0120836 A1 | 6/2005 | Anderson |
| 2005/0191936 A1 | 9/2005 | Marine et al. |
| 2005/0242950 A1 | 11/2005 | Lindsay et al. |
| 2005/0256546 A1 | 11/2005 | Vaisnys et al. |
| 2005/0258963 A1 | 11/2005 | Rodriguez et al. |
| 2006/0020167 A1 | 1/2006 | Sitzmann |
| 2006/0176242 A1 | 8/2006 | Jaramaz et al. |
| 2006/0226957 A1 | 10/2006 | Miller et al. |
| 2006/0247584 A1 | 11/2006 | Sheetz et al. |
| 2006/0252981 A1 | 11/2006 | Matsuda et al. |
| 2007/0005045 A1 | 1/2007 | Mintz et al. |
| 2007/0118115 A1 | 5/2007 | Artale et al. |
| 2007/0152829 A1 | 7/2007 | Lindsay et al. |
| 2007/0191915 A1 | 8/2007 | Strother et al. |
| 2007/0260132 A1 | 11/2007 | Sterling |
| 2007/0270660 A1 | 11/2007 | Caylor et al. |
| 2008/0064920 A1 | 3/2008 | Bakos et al. |
| 2008/0069736 A1 | 3/2008 | Mingerink et al. |
| 2008/0081948 A1 | 4/2008 | Weisenburgh et al. |
| 2008/0083811 A1 | 4/2008 | Marczyk |
| 2008/0208058 A1 | 8/2008 | Sabata et al. |
| 2008/0234866 A1 | 9/2008 | Kishi et al. |
| 2008/0243088 A1 | 10/2008 | Evans |
| 2008/0255420 A1 | 10/2008 | Lee et al. |
| 2009/0110533 A1 | 4/2009 | Jinno |
| 2009/0135280 A1 | 5/2009 | Johnston et al. |
| 2009/0177218 A1 | 7/2009 | Young et al. |
| 2009/0273353 A1 | 11/2009 | Kroh et al. |
| 2009/0277288 A1 | 11/2009 | Doepker et al. |
| 2010/0016853 A1 | 1/2010 | Burbank |
| 2010/0030239 A1 | 2/2010 | Viola et al. |
| 2010/0032179 A1 | 2/2010 | Hanspers et al. |
| 2010/0069833 A1 | 3/2010 | Wenderow et al. |
| 2010/0159435 A1 | 6/2010 | Mueller et al. |
| 2010/0234687 A1 | 9/2010 | Azarbarzin et al. |
| 2010/0291184 A1 | 11/2010 | Clark et al. |
| 2011/0009694 A1 | 1/2011 | Schultz et al. |
| 2011/0028991 A1 | 2/2011 | Ikeda et al. |
| 2011/0029270 A1* | 2/2011 | Mueglitz ............... B25J 9/1692 702/105 |
| 2011/0056717 A1 | 3/2011 | Herisse |
| 2011/0095067 A1 | 4/2011 | Ohdaira |
| 2011/0118708 A1 | 5/2011 | Burbank et al. |
| 2011/0220381 A1 | 9/2011 | Friese et al. |
| 2011/0235168 A1 | 9/2011 | Sander |
| 2011/0251606 A1 | 10/2011 | Kerr |
| 2011/0285507 A1 | 11/2011 | Nelson |
| 2011/0292258 A1 | 12/2011 | Adler et al. |
| 2012/0008880 A1 | 1/2012 | Toth |
| 2012/0078243 A1 | 3/2012 | Worrell et al. |
| 2012/0190964 A1 | 7/2012 | Hyde et al. |
| 2012/0316424 A1 | 12/2012 | Stopek |
| 2013/0075447 A1 | 3/2013 | Weisenburgh, II et al. |
| 2013/0112729 A1 | 5/2013 | Beardsley et al. |
| 2013/0172713 A1 | 7/2013 | Kirschenman |
| 2013/0183769 A1 | 7/2013 | Tajima |
| 2013/0231681 A1 | 9/2013 | Robinson et al. |
| 2013/0284792 A1 | 10/2013 | Ma |
| 2013/0293353 A1 | 11/2013 | McPherson et al. |
| 2013/0303845 A1 | 11/2013 | Skula et al. |
| 2014/0008289 A1 | 1/2014 | Williams et al. |
| 2014/0022283 A1 | 1/2014 | Chan et al. |
| 2014/0041191 A1 | 2/2014 | Knodel |
| 2014/0107697 A1 | 4/2014 | Patani et al. |
| 2014/0155916 A1 | 6/2014 | Hodgkinson et al. |
| 2014/0183244 A1 | 7/2014 | Duque et al. |
| 2014/0262408 A1 | 9/2014 | Woodard |
| 2014/0358163 A1 | 12/2014 | Farin et al. |
| 2015/0001272 A1 | 1/2015 | Sniffin et al. |
| 2015/0025571 A1 | 1/2015 | Suzuki et al. |
| 2015/0039010 A1 | 2/2015 | Beardsley et al. |
| 2015/0082624 A1 | 3/2015 | Craig et al. |
| 2015/0087952 A1 | 3/2015 | Albert et al. |
| 2015/0090760 A1* | 4/2015 | Giordano ............... A61B 34/71 227/176.1 |
| 2015/0230794 A1 | 8/2015 | Wellman et al. |
| 2015/0297824 A1 | 10/2015 | Cabiri et al. |
| 2015/0367497 A1 | 12/2015 | Ito et al. |
| 2016/0029998 A1 | 2/2016 | Brister et al. |
| 2016/0030043 A1 | 2/2016 | Fanelli et al. |
| 2016/0074035 A1 | 3/2016 | Whitman et al. |
| 2016/0135895 A1 | 5/2016 | Faasse et al. |
| 2016/0139666 A1 | 5/2016 | Rubin et al. |
| 2016/0242855 A1 | 8/2016 | Fichtinger et al. |
| 2016/0256221 A1 | 9/2016 | Smith |
| 2016/0270781 A1 | 9/2016 | Scirica |
| 2016/0302820 A1 | 10/2016 | Hibner et al. |
| 2016/0314717 A1 | 10/2016 | Grubbs |
| 2016/0345972 A1 | 12/2016 | Beardsley et al. |
| 2016/0374665 A1 | 12/2016 | DiNardo et al. |
| 2016/0374716 A1 | 12/2016 | Kessler |
| 2017/0000553 A1 | 1/2017 | Wiener et al. |

(56) References Cited

U.S. PATENT DOCUMENTS

| | | |
|---|---|---|
| 2017/0007234 A1 | 1/2017 | Chin et al. |
| 2017/0055981 A1* | 3/2017 | Vendely ............... A61B 17/068 |
| 2017/0066054 A1 | 3/2017 | Birky |
| 2017/0095922 A1 | 4/2017 | Licht et al. |
| 2017/0106302 A1 | 4/2017 | Cummings et al. |
| 2017/0135711 A1 | 5/2017 | Overmyer et al. |
| 2017/0135717 A1 | 5/2017 | Boudreaux et al. |
| 2017/0135747 A1 | 5/2017 | Broderick et al. |
| 2017/0172549 A1 | 6/2017 | Smaby et al. |
| 2017/0182195 A1 | 6/2017 | Wagner |
| 2017/0231629 A1 | 8/2017 | Stopek et al. |
| 2017/0242455 A1 | 8/2017 | Dickens |
| 2017/0245949 A1 | 8/2017 | Randle |
| 2017/0255799 A1 | 9/2017 | Zhao et al. |
| 2017/0296173 A1* | 10/2017 | Shelton, IV ......... A61B 17/068 |
| 2017/0319047 A1 | 11/2017 | Poulsen et al. |
| 2018/0049794 A1 | 2/2018 | Swayze et al. |
| 2018/0051780 A1 | 2/2018 | Shelton, IV et al. |
| 2018/0055501 A1 | 3/2018 | Zemlok et al. |
| 2018/0085120 A1 | 3/2018 | Viola |
| 2018/0092710 A1 | 4/2018 | Bosisio et al. |
| 2018/0133521 A1 | 5/2018 | Frushour et al. |
| 2018/0153634 A1 | 6/2018 | Zemlok et al. |
| 2018/0168572 A1 | 6/2018 | Burbank |
| 2018/0168574 A1 | 6/2018 | Robinson et al. |
| 2018/0168754 A1 | 6/2018 | Overmyer |
| 2018/0235609 A1 | 8/2018 | Harris et al. |
| 2018/0236181 A1 | 8/2018 | Marlin et al. |
| 2018/0242970 A1 | 8/2018 | Mozdzierz |
| 2018/0289371 A1 | 10/2018 | Wang et al. |
| 2018/0296290 A1 | 10/2018 | Namiki et al. |
| 2018/0317905 A1 | 11/2018 | Olson et al. |
| 2018/0368066 A1 | 12/2018 | Howell et al. |
| 2018/0372806 A1 | 12/2018 | Laughery et al. |
| 2019/0000481 A1 | 1/2019 | Harris et al. |
| 2019/0008515 A1 | 1/2019 | Beardsley et al. |
| 2019/0038285 A1 | 2/2019 | Mozdzierz |
| 2019/0046189 A1 | 2/2019 | Dunki-Jacobs et al. |
| 2019/0104919 A1 | 4/2019 | Shelton, IV et al. |
| 2019/0110779 A1 | 4/2019 | Gardner et al. |
| 2019/0125320 A1 | 5/2019 | Shelton, IV et al. |
| 2019/0125321 A1 | 5/2019 | Shelton, IV et al. |
| 2019/0125335 A1 | 5/2019 | Shelton, IV et al. |
| 2019/0125336 A1 | 5/2019 | Deck et al. |
| 2019/0125337 A1 | 5/2019 | Shelton, IV et al. |
| 2019/0125338 A1 | 5/2019 | Shelton, IV et al. |
| 2019/0125339 A1 | 5/2019 | Shelton, IV et al. |
| 2019/0125342 A1 | 5/2019 | Beardsley et al. |
| 2019/0125347 A1 | 5/2019 | Stokes et al. |
| 2019/0125348 A1 | 5/2019 | Shelton, IV et al. |
| 2019/0125352 A1 | 5/2019 | Shelton, IV et al. |
| 2019/0125353 A1 | 5/2019 | Shelton, IV et al. |
| 2019/0125354 A1 | 5/2019 | Deck et al. |
| 2019/0125355 A1 | 5/2019 | Shelton, IV et al. |
| 2019/0125356 A1 | 5/2019 | Shelton, IV et al. |
| 2019/0125357 A1 | 5/2019 | Shelton, IV et al. |
| 2019/0125358 A1 | 5/2019 | Shelton, IV et al. |
| 2019/0125359 A1 | 5/2019 | Shelton, IV et al. |
| 2019/0125360 A1 | 5/2019 | Shelton, IV et al. |
| 2019/0125361 A1 | 5/2019 | Shelton, IV et al. |
| 2019/0125377 A1 | 5/2019 | Shelton, IV |
| 2019/0125378 A1 | 5/2019 | Shelton, IV et al. |
| 2019/0125379 A1 | 5/2019 | Shelton, IV et al. |
| 2019/0125386 A1 | 5/2019 | Shelton, IV et al. |
| 2019/0125387 A1 | 5/2019 | Parihar et al. |
| 2019/0125388 A1 | 5/2019 | Shelton, IV et al. |
| 2019/0125389 A1 | 5/2019 | Shelton, IV et al. |
| 2019/0125430 A1 | 5/2019 | Shelton, IV et al. |
| 2019/0125431 A1 | 5/2019 | Shelton, IV et al. |
| 2019/0125432 A1 | 5/2019 | Shelton, IV et al. |
| 2019/0125454 A1 | 5/2019 | Stokes et al. |
| 2019/0125455 A1 | 5/2019 | Shelton, IV et al. |
| 2019/0125456 A1 | 5/2019 | Shelton, IV et al. |
| 2019/0125457 A1 | 5/2019 | Parihar et al. |
| 2019/0125458 A1 | 5/2019 | Shelton, IV et al. |
| 2019/0125459 A1 | 5/2019 | Shelton, IV et al. |
| 2019/0125476 A1 | 5/2019 | Shelton, IV et al. |
| 2019/0138770 A1 | 5/2019 | Compaijen et al. |
| 2019/0142449 A1 | 5/2019 | Shelton, IV et al. |
| 2019/0150925 A1 | 5/2019 | Marczyk et al. |
| 2019/0151029 A1 | 5/2019 | Robinson |
| 2019/0159778 A1 | 5/2019 | Shelton, IV et al. |
| 2019/0175847 A1 | 6/2019 | Pocreva, III et al. |
| 2019/0200844 A1 | 7/2019 | Shelton, IV et al. |
| 2019/0200905 A1 | 7/2019 | Shelton, IV et al. |
| 2019/0200906 A1 | 7/2019 | Shelton, IV et al. |
| 2019/0200977 A1 | 7/2019 | Shelton, IV et al. |
| 2019/0200981 A1* | 7/2019 | Harris ................ A61B 1/00009 |
| 2019/0200998 A1 | 7/2019 | Shelton, IV et al. |
| 2019/0201023 A1 | 7/2019 | Shelton, IV et al. |
| 2019/0201024 A1 | 7/2019 | Shelton, IV et al. |
| 2019/0201026 A1 | 7/2019 | Shelton, IV et al. |
| 2019/0201027 A1 | 7/2019 | Shelton, IV et al. |
| 2019/0201029 A1 | 7/2019 | Shelton, IV et al. |
| 2019/0201030 A1 | 7/2019 | Shelton, IV et al. |
| 2019/0201033 A1 | 7/2019 | Yates et al. |
| 2019/0201034 A1 | 7/2019 | Shelton, IV et al. |
| 2019/0201045 A1 | 7/2019 | Yates et al. |
| 2019/0201046 A1 | 7/2019 | Shelton, IV et al. |
| 2019/0201047 A1 | 7/2019 | Yates et al. |
| 2019/0201104 A1 | 7/2019 | Shelton, IV et al. |
| 2019/0201112 A1 | 7/2019 | Wiener et al. |
| 2019/0201113 A1 | 7/2019 | Shelton, IV et al. |
| 2019/0201115 A1 | 7/2019 | Shelton, IV et al. |
| 2019/0201116 A1 | 7/2019 | Shelton, IV et al. |
| 2019/0201118 A1 | 7/2019 | Shelton, IV et al. |
| 2019/0201120 A1 | 7/2019 | Shelton, IV et al. |
| 2019/0201136 A1 | 7/2019 | Shelton, IV et al. |
| 2019/0201137 A1 | 7/2019 | Shelton, IV et al. |
| 2019/0201139 A1 | 7/2019 | Shelton, IV et al. |
| 2019/0201140 A1 | 7/2019 | Yates et al. |
| 2019/0201142 A1 | 7/2019 | Shelton, IV et al. |
| 2019/0201594 A1 | 7/2019 | Shelton, IV et al. |
| 2019/0205001 A1 | 7/2019 | Messerly et al. |
| 2019/0205567 A1 | 7/2019 | Shelton, IV et al. |
| 2019/0206003 A1 | 7/2019 | Harris et al. |
| 2019/0206551 A1 | 7/2019 | Yates et al. |
| 2019/0206555 A1 | 7/2019 | Morgan et al. |
| 2019/0206561 A1 | 7/2019 | Shelton, IV et al. |
| 2019/0206563 A1 | 7/2019 | Shelton, IV et al. |
| 2019/0206564 A1 | 7/2019 | Shelton, IV et al. |
| 2019/0206565 A1 | 7/2019 | Shelton, IV |
| 2019/0206569 A1 | 7/2019 | Shelton, IV et al. |
| 2019/0208641 A1 | 7/2019 | Yates et al. |
| 2019/0261983 A1 | 8/2019 | Granger et al. |
| 2019/0261987 A1 | 8/2019 | Viola et al. |
| 2019/0282233 A1 | 9/2019 | Burbank et al. |
| 2019/0290266 A1 | 9/2019 | Scheib et al. |
| 2019/0290297 A1 | 9/2019 | Haider et al. |
| 2019/0298340 A1 | 10/2019 | Shelton, IV et al. |
| 2019/0298350 A1 | 10/2019 | Shelton, IV et al. |
| 2019/0298352 A1 | 10/2019 | Shelton, IV et al. |
| 2019/0298353 A1 | 10/2019 | Shelton, IV et al. |
| 2019/0298354 A1 | 10/2019 | Shelton, IV et al. |
| 2019/0298356 A1 | 10/2019 | Shelton, IV et al. |
| 2019/0298357 A1 | 10/2019 | Shelton, IV et al. |
| 2019/0350581 A1 | 11/2019 | Baxter, III et al. |
| 2020/0015915 A1 | 1/2020 | Swayze et al. |
| 2020/0060523 A1 | 2/2020 | Matsuda et al. |
| 2020/0138534 A1 | 5/2020 | Garcia Kilroy et al. |
| 2020/0146676 A1 | 5/2020 | Yates et al. |
| 2020/0197027 A1 | 6/2020 | Hershberger et al. |
| 2020/0261075 A1 | 8/2020 | Boudreaux et al. |
| 2020/0261076 A1 | 8/2020 | Boudreaux et al. |
| 2020/0261077 A1 | 8/2020 | Shelton, IV et al. |
| 2020/0261078 A1 | 8/2020 | Bakos et al. |
| 2020/0261080 A1 | 8/2020 | Bakos et al. |
| 2020/0261081 A1 | 8/2020 | Boudreaux et al. |
| 2020/0261082 A1 | 8/2020 | Boudreaux et al. |
| 2020/0261083 A1 | 8/2020 | Bakos et al. |
| 2020/0261084 A1 | 8/2020 | Bakos et al. |
| 2020/0261085 A1 | 8/2020 | Boudreaux et al. |
| 2020/0261086 A1 | 8/2020 | Zeiner et al. |
| 2020/0261087 A1 | 8/2020 | Timm et al. |

(56) References Cited

U.S. PATENT DOCUMENTS

| | | |
|---|---|---|
| 2020/0261088 A1 | 8/2020 | Harris et al. |
| 2020/0261089 A1 | 8/2020 | Shelton, IV et al. |
| 2020/0280219 A1 | 9/2020 | Laughery et al. |
| 2020/0289112 A1 | 9/2020 | Whitfield et al. |
| 2020/0297340 A1 | 9/2020 | Hess et al. |
| 2020/0297341 A1 | 9/2020 | Yates et al. |
| 2020/0297346 A1 | 9/2020 | Shelton, IV et al. |
| 2020/0297438 A1 | 9/2020 | Shelton, IV et al. |
| 2020/0305862 A1 | 10/2020 | Yates et al. |
| 2020/0305863 A1 | 10/2020 | Yates et al. |
| 2020/0305864 A1 | 10/2020 | Yates et al. |
| 2020/0305865 A1 | 10/2020 | Shelton, IV |
| 2020/0305868 A1 | 10/2020 | Shelton, IV |
| 2020/0305869 A1 | 10/2020 | Shelton, IV |
| 2020/0305870 A1 | 10/2020 | Shelton, IV |
| 2020/0305871 A1 | 10/2020 | Shelton, IV et al. |
| 2020/0305872 A1 | 10/2020 | Weidner et al. |
| 2020/0305874 A1 | 10/2020 | Huitema et al. |
| 2020/0315612 A1 | 10/2020 | Shelton, IV et al. |
| 2020/0315615 A1 | 10/2020 | Yates et al. |
| 2020/0315616 A1 | 10/2020 | Yates et al. |
| 2020/0315625 A1 | 10/2020 | Hall et al. |
| 2020/0315983 A1 | 10/2020 | Widenhouse et al. |
| 2020/0323526 A1 | 10/2020 | Huang et al. |
| 2020/0330092 A1 | 10/2020 | Shelton, IV et al. |
| 2020/0330093 A1 | 10/2020 | Shelton, IV et al. |
| 2020/0330094 A1 | 10/2020 | Baxter, III et al. |
| 2020/0330096 A1 | 10/2020 | Shelton, IV et al. |
| 2020/0330181 A1 | 10/2020 | Junger et al. |
| 2020/0337693 A1 | 10/2020 | Shelton, IV et al. |
| 2020/0337702 A1 | 10/2020 | Shelton, IV et al. |
| 2020/0337703 A1 | 10/2020 | Shelton, IV et al. |
| 2020/0337791 A1 | 10/2020 | Shelton, IV et al. |
| 2020/0345346 A1 | 11/2020 | Shelton, IV et al. |
| 2020/0345349 A1 | 11/2020 | Kimball et al. |
| 2020/0345352 A1 | 11/2020 | Shelton, IV et al. |
| 2020/0345353 A1 | 11/2020 | Leimbach et al. |
| 2020/0345354 A1 | 11/2020 | Leimbach et al. |
| 2020/0345355 A1 | 11/2020 | Baxter, III et al. |
| 2020/0345356 A1 | 11/2020 | Leimbach et al. |
| 2020/0345357 A1 | 11/2020 | Leimbach et al. |
| 2020/0345358 A1 | 11/2020 | Jenkins |
| 2020/0345359 A1 | 11/2020 | Baxter, III et al. |
| 2020/0345360 A1 | 11/2020 | Leimbach et al. |
| 2020/0345361 A1 | 11/2020 | Shelton, IV et al. |
| 2020/0345446 A1 | 11/2020 | Kimball et al. |
| 2020/0352562 A1 | 11/2020 | Timm et al. |
| 2020/0367885 A1 | 11/2020 | Yates et al. |
| 2020/0367886 A1 | 11/2020 | Shelton, IV et al. |
| 2020/0375585 A1 | 12/2020 | Swayze et al. |
| 2020/0375592 A1 | 12/2020 | Hall et al. |
| 2020/0375593 A1 | 12/2020 | Hunter et al. |
| 2020/0375597 A1 | 12/2020 | Shelton, IV et al. |
| 2020/0390444 A1 | 12/2020 | Harris et al. |
| 2020/0397433 A1 | 12/2020 | Lytle, IV et al. |
| 2020/0397434 A1 | 12/2020 | Overmyer et al. |
| 2020/0405290 A1 | 12/2020 | Shelton, IV et al. |
| 2020/0405292 A1 | 12/2020 | Shelton, IV et al. |
| 2020/0405293 A1 | 12/2020 | Shelton, IV et al. |
| 2020/0405294 A1 | 12/2020 | Shelton, IV |
| 2020/0405295 A1 | 12/2020 | Shelton, IV et al. |
| 2020/0405296 A1 | 12/2020 | Shelton, IV et al. |
| 2020/0405297 A1 | 12/2020 | Shelton, IV et al. |
| 2020/0405302 A1 | 12/2020 | Shelton, IV et al. |
| 2020/0405303 A1 | 12/2020 | Shelton, IV |
| 2020/0405306 A1 | 12/2020 | Shelton, IV et al. |
| 2020/0405307 A1 | 12/2020 | Shelton, IV et al. |
| 2020/0405308 A1 | 12/2020 | Shelton, IV |
| 2020/0405309 A1 | 12/2020 | Shelton, IV et al. |
| 2020/0405311 A1 | 12/2020 | Shelton, IV et al. |
| 2020/0405312 A1 | 12/2020 | Shelton, IV et al. |
| 2020/0405313 A1 | 12/2020 | Shelton, IV |
| 2020/0405314 A1 | 12/2020 | Shelton, IV et al. |
| 2020/0405316 A1 | 12/2020 | Shelton, IV et al. |
| 2020/0405341 A1 | 12/2020 | Hess et al. |
| 2020/0405409 A1 | 12/2020 | Shelton, IV et al. |
| 2020/0405410 A1 | 12/2020 | Shelton, IV |
| 2020/0405416 A1 | 12/2020 | Shelton, IV et al. |
| 2020/0405436 A1 | 12/2020 | Shelton, IV et al. |
| 2020/0405437 A1 | 12/2020 | Shelton, IV et al. |
| 2020/0405438 A1 | 12/2020 | Shelton, IV et al. |
| 2020/0405439 A1 | 12/2020 | Shelton, IV et al. |
| 2020/0405440 A1 | 12/2020 | Shelton, IV et al. |
| 2020/0405441 A1 | 12/2020 | Shelton, IV et al. |
| 2020/0410180 A1 | 12/2020 | Shelton, IV et al. |
| 2021/0000466 A1 | 1/2021 | Leimbach et al. |
| 2021/0000467 A1 | 1/2021 | Shelton, IV et al. |
| 2021/0000470 A1 | 1/2021 | Leimbach et al. |
| 2021/0015480 A1 | 1/2021 | Shelton, IV et al. |
| 2021/0022741 A1 | 1/2021 | Baxter, III et al. |
| 2021/0030416 A1 | 2/2021 | Shelton, IV et al. |
| 2021/0045742 A1 | 2/2021 | Shelton, IV et al. |
| 2021/0052271 A1 | 2/2021 | Harris et al. |
| 2021/0059661 A1 | 3/2021 | Schmid et al. |
| 2021/0059662 A1 | 3/2021 | Shelton, IV |
| 2021/0059664 A1 | 3/2021 | Hensel et al. |
| 2021/0059666 A1 | 3/2021 | Schmid et al. |
| 2021/0059669 A1 | 3/2021 | Yates et al. |
| 2021/0059670 A1 | 3/2021 | Overmyer et al. |
| 2021/0059671 A1 | 3/2021 | Shelton, IV et al. |
| 2021/0059672 A1 | 3/2021 | Giordano et al. |
| 2021/0059673 A1 | 3/2021 | Shelton, IV et al. |
| 2021/0068817 A1 | 3/2021 | Shelton, IV et al. |
| 2021/0068818 A1 | 3/2021 | Overmyer et al. |
| 2021/0068820 A1 | 3/2021 | Parihar et al. |
| 2021/0068829 A1 | 3/2021 | Miller et al. |
| 2021/0068830 A1 | 3/2021 | Baber et al. |
| 2021/0068831 A1 | 3/2021 | Baber et al. |
| 2021/0068832 A1 | 3/2021 | Yates et al. |
| 2021/0068835 A1 | 3/2021 | Shelton, IV et al. |
| 2021/0077092 A1 | 3/2021 | Parihar et al. |
| 2021/0077099 A1 | 3/2021 | Shelton, IV et al. |
| 2021/0077100 A1 | 3/2021 | Shelton, IV et al. |
| 2021/0077109 A1 | 3/2021 | Harris et al. |
| 2021/0085313 A1 | 3/2021 | Morgan et al. |
| 2021/0085314 A1 | 3/2021 | Schmid et al. |
| 2021/0085315 A1 | 3/2021 | Aronhalt et al. |
| 2021/0085316 A1 | 3/2021 | Harris et al. |
| 2021/0085317 A1 | 3/2021 | Miller et al. |
| 2021/0085318 A1 | 3/2021 | Swayze et al. |
| 2021/0085319 A1 | 3/2021 | Swayze et al. |
| 2021/0085320 A1 | 3/2021 | Leimbach et al. |
| 2021/0085321 A1 | 3/2021 | Shelton, IV et al. |
| 2021/0085325 A1 | 3/2021 | Shelton, IV et al. |
| 2021/0085326 A1 | 3/2021 | Vendely et al. |
| 2021/0093321 A1 | 4/2021 | Auld et al. |
| 2021/0093323 A1 | 4/2021 | Scirica et al. |
| 2021/0100541 A1 | 4/2021 | Shelton, IV et al. |
| 2021/0100550 A1 | 4/2021 | Shelton, IV et al. |
| 2021/0100982 A1 | 4/2021 | Laby et al. |
| 2021/0106333 A1 | 4/2021 | Shelton, IV et al. |
| 2021/0107031 A1 | 4/2021 | Bales, Jr. et al. |
| 2021/0121175 A1 | 4/2021 | Yates et al. |
| 2021/0128146 A1 | 5/2021 | Shelton, IV et al. |
| 2021/0137522 A1 | 5/2021 | Shelton, IV et al. |
| 2021/0186490 A1 | 6/2021 | Shelton, IV et al. |
| 2021/0186492 A1 | 6/2021 | Shelton, IV et al. |
| 2021/0186493 A1 | 6/2021 | Shelton, IV et al. |
| 2021/0186494 A1 | 6/2021 | Shelton, IV et al. |
| 2021/0186495 A1 | 6/2021 | Shelton, IV et al. |
| 2021/0186497 A1 | 6/2021 | Shelton, IV et al. |
| 2021/0186498 A1 | 6/2021 | Boudreaux et al. |
| 2021/0186499 A1 | 6/2021 | Shelton, IV et al. |
| 2021/0186500 A1 | 6/2021 | Shelton, IV et al. |
| 2021/0186501 A1 | 6/2021 | Shelton, IV et al. |
| 2021/0186502 A1 | 6/2021 | Shelton, IV et al. |
| 2021/0186503 A1 | 6/2021 | Shelton, IV et al. |
| 2021/0186504 A1 | 6/2021 | Shelton, IV et al. |
| 2021/0186505 A1 | 6/2021 | Shelton, IV et al. |
| 2021/0186506 A1 | 6/2021 | Shelton, IV et al. |
| 2021/0186507 A1 | 6/2021 | Shelton, IV et al. |
| 2021/0212691 A1 | 7/2021 | Smith et al. |
| 2021/0212776 A1 | 7/2021 | Schmitt et al. |
| 2021/0219976 A1 | 7/2021 | DiNardo et al. |

(56) References Cited

U.S. PATENT DOCUMENTS

| | | |
|---|---|---|
| 2021/0228209 A1 | 7/2021 | Shelton, IV et al. |
| 2021/0236117 A1 | 8/2021 | Morgan et al. |
| 2021/0236124 A1 | 8/2021 | Shelton, IV et al. |
| 2021/0244406 A1 | 8/2021 | Kerr et al. |
| 2021/0244407 A1 | 8/2021 | Shelton, IV et al. |
| 2021/0244410 A1 | 8/2021 | Swayze et al. |
| 2021/0244412 A1 | 8/2021 | Vendely et al. |
| 2021/0259681 A1 | 8/2021 | Shelton, IV et al. |
| 2021/0259687 A1 | 8/2021 | Gonzalez et al. |
| 2021/0259986 A1 | 8/2021 | Widenhouse et al. |
| 2021/0259987 A1 | 8/2021 | Widenhouse et al. |
| 2021/0267589 A1 | 9/2021 | Swayze et al. |
| 2021/0267592 A1 | 9/2021 | Baxter, III et al. |
| 2021/0267594 A1 | 9/2021 | Morgan et al. |
| 2021/0267595 A1 | 9/2021 | Posada et al. |
| 2021/0267596 A1 | 9/2021 | Fanelli et al. |
| 2021/0275053 A1 | 9/2021 | Shelton, IV et al. |
| 2021/0275172 A1 | 9/2021 | Harris et al. |
| 2021/0275173 A1 | 9/2021 | Shelton, IV et al. |
| 2021/0275176 A1 | 9/2021 | Beckman et al. |
| 2021/0282767 A1 | 9/2021 | Shelton, IV et al. |
| 2021/0282769 A1 | 9/2021 | Baxter, III et al. |
| 2021/0282774 A1 | 9/2021 | Shelton, IV et al. |
| 2021/0282776 A1 | 9/2021 | Overmyer et al. |
| 2021/0290226 A1 | 9/2021 | Mandakolathur Vasudevan et al. |
| 2021/0290231 A1 | 9/2021 | Baxter, III et al. |
| 2021/0290232 A1 | 9/2021 | Harris et al. |
| 2021/0290233 A1 | 9/2021 | Shelton, IV et al. |
| 2021/0290236 A1 | 9/2021 | Moore et al. |
| 2021/0298745 A1 | 9/2021 | Leimbach et al. |
| 2021/0298746 A1 | 9/2021 | Leimbach et al. |
| 2021/0307748 A1 | 10/2021 | Harris et al. |
| 2021/0307754 A1 | 10/2021 | Shelton, IV et al. |
| 2021/0315566 A1 | 10/2021 | Yates et al. |
| 2021/0315570 A1 | 10/2021 | Shelton, IV |
| 2021/0315571 A1 | 10/2021 | Swayze et al. |
| 2021/0315573 A1 | 10/2021 | Shelton, IV et al. |
| 2021/0315574 A1 | 10/2021 | Shelton, IV et al. |
| 2021/0315576 A1 | 10/2021 | Shelton, IV et al. |
| 2021/0315577 A1 | 10/2021 | Shelton, IV et al. |
| 2021/0322009 A1 | 10/2021 | Huang et al. |
| 2021/0330321 A1 | 10/2021 | Leimbach et al. |
| 2021/0338233 A1 | 11/2021 | Shelton, IV et al. |
| 2021/0338234 A1 | 11/2021 | Shelton, IV et al. |
| 2021/0369273 A1 | 12/2021 | Yates et al. |
| 2021/0378669 A1 | 12/2021 | Shelton, IV et al. |
| 2021/0393260 A1 | 12/2021 | Shelton, IV et al. |
| 2021/0393261 A1 | 12/2021 | Harris et al. |
| 2021/0393262 A1 | 12/2021 | Shelton, IV et al. |
| 2021/0393268 A1 | 12/2021 | Shelton, IV et al. |
| 2021/0393366 A1 | 12/2021 | Shelton, IV et al. |
| 2022/0000478 A1 | 1/2022 | Shelton, IV et al. |

FOREIGN PATENT DOCUMENTS

| | | | | |
|---|---|---|---|---|
| CN | 101188900 | A | 5/2008 | |
| CN | 101203085 | A | 6/2008 | |
| CN | 101273908 | A | 10/2008 | |
| CN | 101716090 | A | 6/2010 | |
| CN | 101756727 | A | 6/2010 | |
| CN | 101856250 | A | 10/2010 | |
| CN | 102243850 | A | 11/2011 | |
| CN | 102247182 | A | 11/2011 | |
| CN | 102309352 | A | 1/2012 | |
| CN | 102743201 | A | 10/2012 | |
| CN | 103083053 | A | 5/2013 | |
| CN | 103391037 | A | 11/2013 | |
| CN | 203328751 | U | 12/2013 | |
| CN | 103505264 | A | 1/2014 | |
| CN | 103635150 | A | 3/2014 | |
| CN | 103860221 | A | 6/2014 | |
| CN | 104027145 | A | 9/2014 | |
| CN | 104422849 | A | 3/2015 | |
| CN | 204520822 | U | 8/2015 | |
| CN | 105919642 | A | 9/2016 | |
| CN | 105997173 | A | 10/2016 | |
| CN | 208625784 | U | 3/2019 | |
| DE | 102004041871 | A1 | 3/2006 | |
| DE | 102013101158 | A1 | 8/2014 | |
| EM | 1558161 | A1 | 8/2005 | |
| EP | 1064882 | A1 | 1/2001 | |
| EP | 2789299 | A1 | 10/2014 | |
| EP | 2878274 | A1 | 6/2015 | |
| EP | 3326548 | A1 | 5/2018 | |
| EP | 3476334 | A1 | 5/2019 | |
| ES | 1070456 | U | 9/2009 | |
| JP | H02106189 | A | 4/1990 | |
| JP | H06304176 | A | 11/1994 | |
| JP | 2000210299 | A | 8/2000 | |
| JP | 2001-69758 | A | 3/2001 | |
| JP | 2001208655 | A | 8/2001 | |
| JP | 2007-97252 | A | 4/2007 | |
| JP | 2007304057 | A | 11/2007 | |
| JP | 2007306710 | A | 11/2007 | |
| JP | 2008154804 | A | 7/2008 | |
| JP | 2010065594 | A | 3/2010 | |
| JP | 2011200665 | A | 10/2011 | |
| JP | 2013541982 | A | 11/2013 | |
| JP | 2013541997 | A | 11/2013 | |
| JP | 2014171879 | A | 9/2014 | |
| JP | 2015516838 | A | 6/2015 | |
| JP | 2015521524 | A | 7/2015 | |
| JP | 2016007800 | A | 1/2016 | |
| JP | 2016508792 | A | 3/2016 | |
| JP | 2016530949 | A | 10/2016 | |
| JP | 2017513563 | A | 6/2017 | |
| JP | 2019513530 | A | 5/2019 | |
| KR | 20180053811 | * | 5/2018 | ............ A61L 31/10 |
| SU | 1042742 | A1 | 9/1983 | |
| WO | WO-9308754 | A1 | 5/1993 | |
| WO | WO-2014175894 | A1 | 10/2014 | |
| WO | WO-2015076780 | A1 | 5/2015 | |
| WO | WO-2015137040 | A1 | 9/2015 | |
| WO | WO-2019036490 | A1 | 2/2019 | |

OTHER PUBLICATIONS

"ATM-MPLS Network Interworking Version 2.0, af-aic-0178.001" ATM Standard, The ATM Forum Technical Committee, published Aug. 2003.

Yang et al.; "4D printing reconfigurable, deployable and mechanically tunable metamaterials," Material Horizons, vol. 6, pp. 1244-1250 (2019).

"Council Directive 93/42/EEC of Jun. 14, 1993 Concerning Medical Devices," Official Journal of the European Communities, L&C. Ligislation and Competition, S, No. L 169, Jun. 14, 1993, pp. 1-43.

* cited by examiner

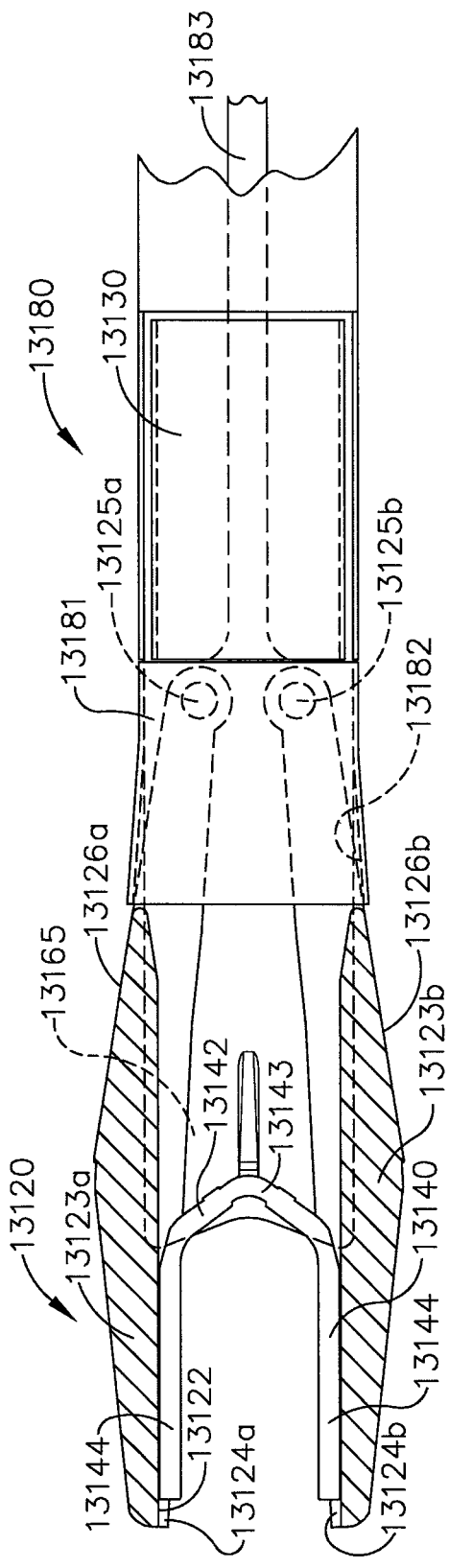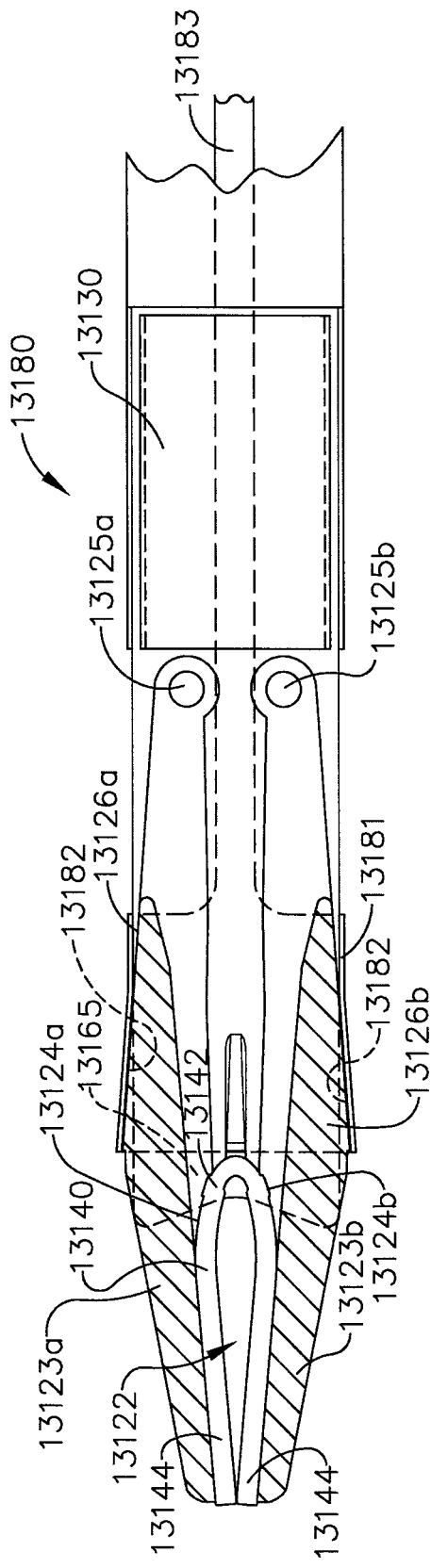

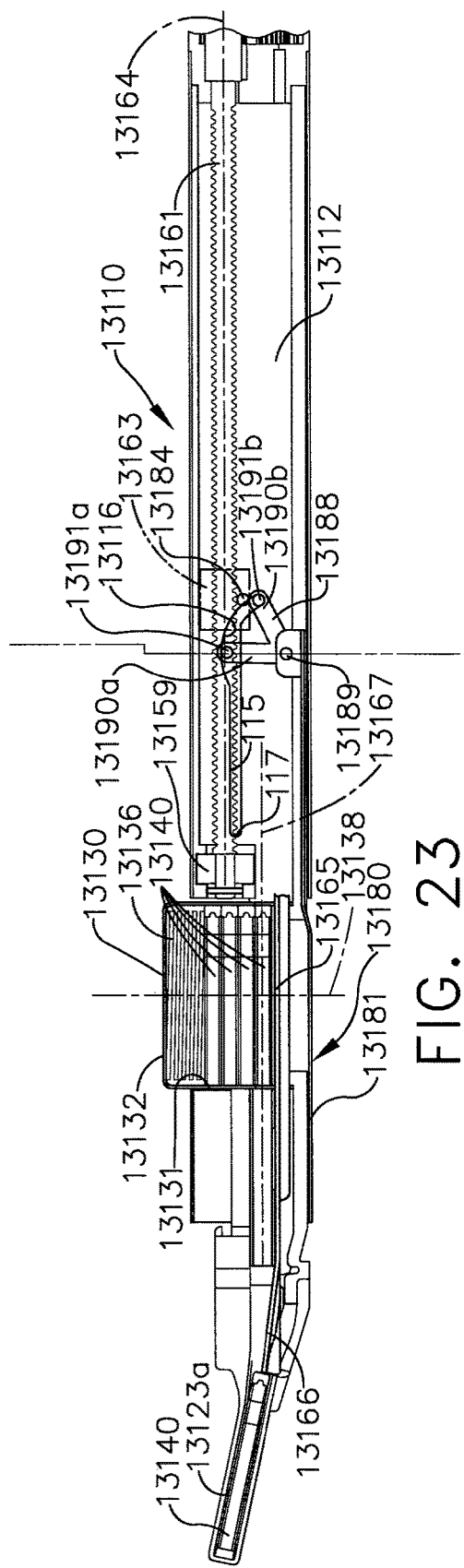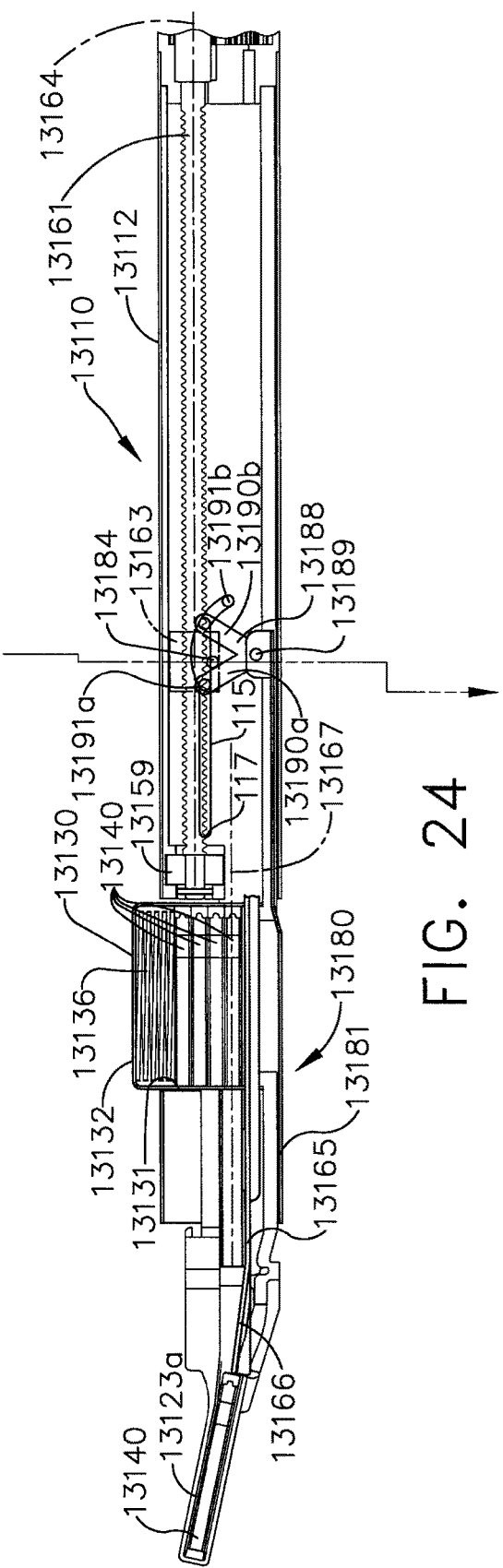

RFID IDENTIFICATION SYSTEMS FOR SURGICAL INSTRUMENTS

CROSS-REFERENCE TO RELATED APPLICATIONS

This application is a non-provisional application claiming priority under 35 U.S.C. § 119(e) to U.S. Provisional Patent Application Ser. No. 62/868,457, entitled SURGICAL SYSTEMS WITH MULTIPLE RFID TAGS, filed on Jun. 28, 2019, the entire disclosure of which is hereby incorporated by reference herein.

BACKGROUND

The present invention relates to surgical instruments and, in various embodiments, to surgical cutting and stapling instruments and staple cartridges therefor that are designed to cut and staple tissue. In various embodiments, RFID technology can be used to identify the components of a surgical instrument, such as staple cartridges, for example. Examples of surgical systems which use RFID technology can be found in the disclosures of U.S. Pat. No. 7,959,050, entitled ELECTRICALLY SELF-POWERED SURGICAL INSTRUMENT WITH MANUAL RELEASE, which issued on Jun. 14, 2011, and U.S. Patent Application No. 2015/0053743, entitled ERROR DETECTION ARRANGEMENTS FOR SURGICAL INSTRUMENT ASSEMBLIES, which published on Feb. 26, 2015, and both of which are incorporated by reference herein in their entireties.

SUMMARY

In various embodiments, a surgical device for applying clips is disclosed. The surgical device includes an elongate shaft extending from a housing, an end effector extending from the elongate shaft, a cartridge, a crimping drive, an RFID tag including stored data, an RFID scanner configured to send an interrogation signal to the RFID tag and receive a first signal from the RFID tag in response to the interrogation signal, and a controller in communication with the RFID scanner. The end effector includes a first jaw and a second jaw. The first jaw and the second jaw are movable relative to each other between an open position and a closed position. The cartridge includes a storage chamber and a plurality of clips removably positioned within the storage chamber. The crimping drive is configured to move the first jaw and the second jaw to the closed position during a crimping stroke. One of the plurality of clips is crimped around tissue of a patient during the crimping stroke. The stored data on the RFID tag relates to an identifying characteristic of at least one of the plurality of clips within the cartridge. The first signal includes the stored data on the RFID tag. The controller is configured to compare the stored data received by the RFID scanner to a set of compatibility data stored in a memory of the controller and vary an operational parameter of the surgical device based on the stored data received by the RFID scanner.

In various embodiments, a surgical device for applying clips is disclosed. The surgical device includes an elongate shaft extending from a housing, an end effector extending from the elongate shaft, a clip including an RFID tag, a crimping drive, an RFID scanner, and a controller in communication with the RFID scanner. The end effector includes a first jaw and a second jaw. The first jaw is movable relative to the second jaw between an open position and a closed position. The RFID tag includes stored data. The stored data on the RFID tag is representative of the clip. The crimping drive is configured to move the first jaw and the second jaw to the closed position during a crimping stroke. The clip is crimped around tissue of a patient during the crimping stroke. The RFID scanner is configured to receive the stored data on the RFID tag. The controller is configured to determine if the clip is compatible for use with the surgical device by comparing the stored data received by the RFID scanner to a set of compatibility data, permit the surgical device to perform a function when the controller determines the clip is compatible for use with the surgical device, and prevent the surgical device from performing the function when the controller determines the clip is incompatible for use with the surgical device.

In various embodiments, a surgical device for applying clips is disclosed. The surgical device includes an elongate shaft extending from a housing, an end effector extending from the elongate shaft, a cartridge, a crimping drive, an RFID tag including stored data, an RFID scanner configured to communicate with the RFID tag, and a controller in communication with the RFID scanner. The end effector includes a first jaw and a second jaw. The first jaw and the second jaw are movable relative to each other between an open position and a closed position. The cartridge includes a storage chamber and a plurality of clips removably positioned within the storage chamber. The crimping drive is configured to move the first jaw and the second jaw to the closed position during a crimping stroke. One of the plurality of clips is crimped around tissue of a patient during the crimping stroke. The stored data on the RFID tag relates to an identifying characteristic of the plurality of clips within the cartridge. The RFID scanner is configured to receive the stored data from the RFID tag. The controller is configured to compare the stored data received by the RFID scanner to a set of authenticity data, permit the surgical device to perform the crimping stroke when the controller determines that the plurality of clips are authentic, and prevent the surgical device from performing the crimping stroke when the controller determines that the plurality of clips are inauthentic.

BRIEF DESCRIPTION OF THE DRAWINGS

Various features of the embodiments described herein, together with advantages thereof, may be understood in accordance with the following description taken in conjunction with the accompanying drawings as follows:

FIG. 19 is a partial cross-sectional view of the clip applier of FIG. 17 in an open configuration;

FIG. 20 is a partial cross-sectional view of the clip applier of FIG. 17 in a closed configuration;

FIG. 23 is a cross-sectional view of the end effector of FIG. 18 illustrating the firing drive coming into engagement with the crimping drive;

FIG. 24 is a cross-sectional view of the end effector of FIG. 18 illustrating the crimping drive in an at least partially fired condition;

DESCRIPTION

Figure 1:
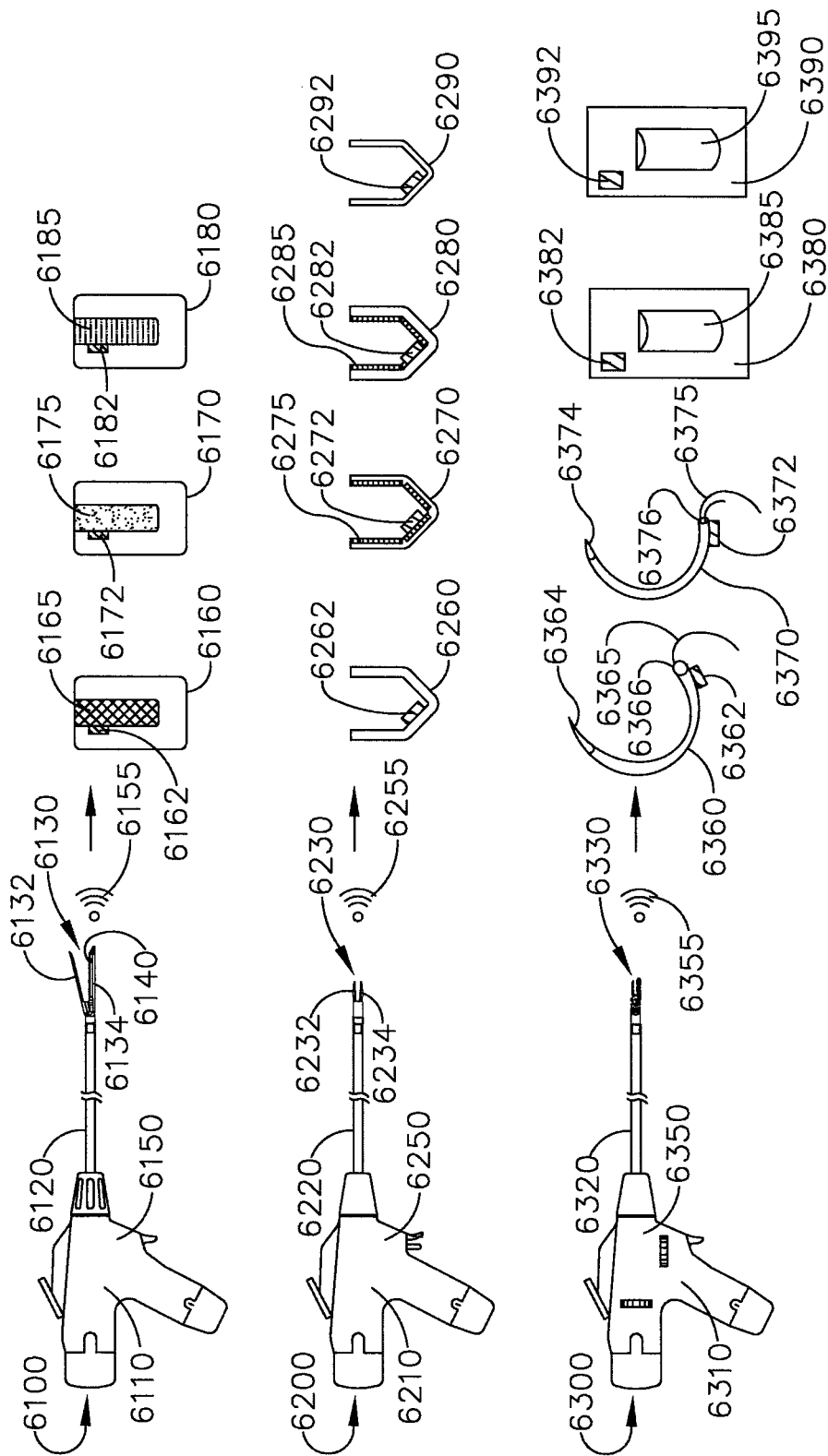
FIG. 1 is a schematic of various surgical instruments and supplemental components for use with the surgical instruments.

Applicant of the present application owns the following U.S. patent applications that were filed on Jun. 30, 2019 and which are each herein incorporated by reference in their respective entireties:

U.S. patent application Ser. No. 16/458,104, entitled METHOD FOR AUTHENTICATING THE COMPATIBILITY OF A STAPLE CARTRIDGE WITH A SURGICAL INSTRUMENT, now U.S. Patent Application Publication No. 2020/0405301;

U.S. patent application Ser. No. 16/458,108, entitled SURGICAL INSTRUMENT SYSTEM COMPRISING AN RFID SYSTEM, now U.S. Patent Application Publication No. 2020/0405436;

U.S. patent application Ser. No. 16/458,111, entitled SURGICAL INSTRUMENT COMPRISING AN RFID SYSTEM FOR TRACKING A MOVABLE COMPONENT, now U.S. Patent Application Publication No. 2020/0405437;

U.S. patent application Ser. No. 16/458,114, entitled SURGICAL INSTRUMENT COMPRISING AN ALIGNED RFID SENSOR, now U.S. Patent Application Publication No. 2020/0405438;

U.S. patent application Ser. No. 16/458,105, entitled SURGICAL STAPLING SYSTEM HAVING AN INFORMATION DECRYPTION PROTOCOL, now U.S. Patent Application Publication No. 2020/0015914;

U.S. patent application Ser. No. 16/458,110, entitled SURGICAL STAPLING SYSTEM HAVING AN INFORMATION ENCRYPTION PROTOCOL, now U.S. Patent Application Publication No. 2020/0405297;

U.S. patent application Ser. No. 16/458,120, entitled SURGICAL STAPLING SYSTEM HAVING A LOCKOUT MECHANISM FOR AN INCOMPATIBLE CARTRIDGE, now U.S. Patent Application Publication No. 2020/0405303;

U.S. patent application Ser. No. 16/458,125, entitled SURGICAL STAPLING SYSTEM HAVING A FRANGIBLE RFID TAG, now U.S. Patent Application Publication No. 2020/0405441; and U.S. patent application Ser. No. 16/458,103, entitled PACKAGING FOR A REPLACEABLE COMPONENT OF A SURGICAL STAPLING SYSTEM, now U.S. Patent Application Publication No. 2020/0405296.

Applicant of the present application owns the following U.S. patent applications that were filed on Jun. 30, 2019 and which are each herein incorporated by reference in their respective entireties:

U.S. patent application Ser. No. 16/458,107, entitled METHOD OF USING MULTIPLE RFID CHIPS WITH A SURGICAL ASSEMBLY, now U.S. Patent Application Publication No. 2020/0405311;

U.S. patent application Ser. No. 16/458,109, entitled MECHANISMS FOR PROPER ANVIL ATTACH- MENT SURGICAL STAPLING HEAD ASSEMBLY, now U.S. Patent Application Publication No. 2020/0405312;

U.S. patent application Ser. No. 16/458,119, entitled MECHANISMS FOR MOTOR CONTROL ADJUSTMENTS OF A MOTORIZED SURGICAL INSTRUMENT, now U.S. Patent Application Publication No. 2020/0405314;

U.S. patent application Ser. No. 16/458,115, entitled SURGICAL INSTRUMENT WITH BATTERY COMPATIBILITY VERIFICATION FUNCTIONALITY, now U.S. Patent Application Publication No. 2020/0405313;

U.S. patent application Ser. No. 16/458,117, entitled SURGICAL SYSTEM WITH RFID TAGS FOR UPDATING MOTOR ASSEMBLY PARAMETERS, now U.S. Patent Application Publication No. 2020/0405439;

U.S. patent application Ser. No. 16/458,121, entitled SURGICAL SYSTEMS WITH MULTIPLE RFID TAGS, now U.S. Patent Application Publication No. 2020/0405440;

U.S. patent application Ser. No. 16/458,106, entitled RFID IDENTIFICATION SYSTEMS FOR SURGICAL INSTRUMENTS, now U.S. Patent Application Publication No. 2020/0405316;

U.S. patent application Ser. No. 16/458,112, entitled SURGICAL RFID ASSEMBLIES FOR DISPLAY AND COMMUNICATION, now U.S. Patent Application Publication No. 2020/0405409;

U.S. patent application Ser. No. 16/458,116, entitled SURGICAL RFID ASSEMBLIES FOR COMPATIBILITY DETECTION, now U.S. Patent Application Publication No. 2020/0410180; and U.S. patent application Ser. No. 16/458,118, entitled SURGICAL RFID ASSEMBLIES FOR INSTRUMENT OPERATIONAL SETTING CONTROL, now U.S. Patent Application Publication No. 2020/0405410.

Applicant of the present application owns the following U.S. patent applications that were filed on May 1, 2018 and which are each herein incorporated by reference in their respective entireties:

U.S. Provisional Patent Application Ser. No. 62/665,129, entitled SURGICAL SUTURING SYSTEMS;

U.S. Provisional Patent Application Ser. No. 62/665,139, entitled SURGICAL INSTRUMENTS COMPRISING CONTROL SYSTEMS;

U.S. Provisional Patent Application Ser. No. 62/665,177, entitled SURGICAL INSTRUMENTS COMPRISING HANDLE ARRANGEMENTS;

U.S. Provisional Patent Application Ser. No. 62/665,128, entitled MODULAR SURGICAL INSTRUMENTS;

U.S. Provisional Patent Application Ser. No. 62/665,192, entitled SURGICAL DISSECTORS; AND U.S. Provisional Patent Application Ser. No. 62/665,134, entitled SURGICAL CLIP APPLIER.

Applicant of the present application owns the following U.S. patent applications that were filed on Aug. 24, 2018 which are each herein incorporated by reference in their respective entireties:

U.S. patent application Ser. No. 16/112,129, entitled SURGICAL SUTURING INSTRUMENT CONFIGURED TO MANIPULATE TISSUE USING MECHANICAL AND ELECTRICAL POWER;

U.S. patent application Ser. No. 16/112,155, entitled SURGICAL SUTURING INSTRUMENT COMPRISING A CAPTURE WIDTH WHICH IS LARGER THAN TROCAR DIAMETER;

U.S. patent application Ser. No. 16/112,168, entitled SURGICAL SUTURING INSTRUMENT COMPRISING A NON-CIRCULAR NEEDLE;

U.S. patent application Ser. No. 16/112,180, entitled ELECTRICAL POWER OUTPUT CONTROL BASED ON MECHANICAL FORCES;

U.S. patent application Ser. No. 16/112,193, entitled REACTIVE ALGORITHM FOR SURGICAL SYSTEM;

U.S. patent application Ser. No. 16/112,099, entitled SURGICAL INSTRUMENT COMPRISING AN ADAPTIVE ELECTRICAL SYSTEM;

U.S. patent application Ser. No. 16/112,112, entitled CONTROL SYSTEM ARRANGEMENTS FOR A MODULAR SURGICAL INSTRUMENT;

U.S. patent application Ser. No. 16/112,119, entitled ADAPTIVE CONTROL PROGRAMS FOR A SURGICAL SYSTEM COMPRISING MORE THAN ONE TYPE OF CARTRIDGE;

U.S. patent application Ser. No. 16/112,097, entitled SURGICAL INSTRUMENT SYSTEMS COMPRISING BATTERY ARRANGEMENTS;

U.S. patent application Ser. No. 16/112,109, entitled SURGICAL INSTRUMENT SYSTEMS COMPRISING HANDLE ARRANGEMENTS;

U.S. patent application Ser. No. 16/112,114, entitled SURGICAL INSTRUMENT SYSTEMS COMPRISING FEEDBACK MECHANISMS;

U.S. patent application Ser. No. 16/112,117, entitled SURGICAL INSTRUMENT SYSTEMS COMPRISING LOCKOUT MECHANISMS;

U.S. patent application Ser. No. 16/112,095, entitled SURGICAL INSTRUMENTS COMPRISING A LOCKABLE END EFFECTOR SOCKET;

U.S. patent application Ser. No. 16/112,121, entitled SURGICAL INSTRUMENTS COMPRISING A SHIFTING MECHANISM;

U.S. patent application Ser. No. 16/112,151, entitled SURGICAL INSTRUMENTS COMPRISING A SYSTEM FOR ARTICULATION AND ROTATION COMPENSATION;

U.S. patent application Ser. No. 16/112,154, entitled SURGICAL INSTRUMENTS COMPRISING A BIASED SHIFTING MECHANISM;

U.S. patent application Ser. No. 16/112,226, entitled SURGICAL INSTRUMENTS COMPRISING AN ARTICULATION DRIVE THAT PROVIDES FOR HIGH ARTICULATION ANGLES;

U.S. patent application Ser. No. 16/112,062, entitled SURGICAL DISSECTORS AND MANUFACTURING TECHNIQUES;

U.S. patent application Ser. No. 16/112,098, entitled SURGICAL DISSECTORS CONFIGURED TO APPLY MECHANICAL AND ELECTRICAL ENERGY;

U.S. patent application Ser. No. 16/112,237, entitled SURGICAL CLIP APPLIER CONFIGURED TO STORE CLIPS IN A STORED STATE;

U.S. patent application Ser. No. 16/112,245, entitled SURGICAL CLIP APPLIER COMPRISING AN EMPTY CLIP CARTRIDGE LOCKOUT;

U.S. patent application Ser. No. 16/112,249, entitled SURGICAL CLIP APPLIER COMPRISING AN AUTOMATIC CLIP FEEDING SYSTEM;

U.S. patent application Ser. No. 16/112,253, entitled SURGICAL CLIP APPLIER COMPRISING ADAPTIVE FIRING CONTROL; and U.S. patent application Ser. No. 16/112,257, entitled SURGICAL CLIP APPLIER COMPRISING ADAPTIVE CONTROL IN RESPONSE TO A STRAIN GAUGE CIRCUIT.

Applicant of the present application owns the following U.S. patent applications that were filed on Oct. 26, 2018 which are each herein incorporated by reference in their respective entireties:

U.S. patent application Ser. No. 16/172,130, entitled CLIP APPLIER COMPRISING INTERCHANGEABLE CLIP RELOADS;

U.S. patent application Ser. No. 16/172,066, entitled CLIP APPLIER COMPRISING A MOVABLE CLIP MAGAZINE;

U.S. patent application Ser. No. 16/172,078, entitled CLIP APPLIER COMPRISING A ROTATABLE CLIP MAGAZINE;

U.S. patent application Ser. No. 16/172,087, entitled CLIP APPLIER COMPRISING CLIP ADVANCING SYSTEMS;

U.S. patent application Ser. No. 16/172,094, entitled CLIP APPLIER COMPRISING A CLIP CRIMPING SYSTEM;

U.S. patent application Ser. No. 16/172,128, entitled CLIP APPLIER COMPRISING A RECIPROCATING CLIP ADVANCING MEMBER;

U.S. patent application Ser. No. 16/172,168, entitled CLIP APPLIER COMPRISING A MOTOR CONTROLLER;

U.S. patent application Ser. No. 16/172,164, entitled SURGICAL SYSTEM COMPRISING A SURGICAL TOOL AND A SURGICAL HUB; and U.S. patent application Ser. No. 16/172,303, entitled METHOD FOR OPERATING A POWERED ARTICULATING MULTI-CLIP APPLIER.

Applicant of the present application owns the following U.S. patent applications, filed on Dec. 4, 2018, the disclosure of each of which is herein incorporated by reference in its entirety:

U.S. patent application Ser. No. 16/209,385, titled METHOD OF HUB COMMUNICATION, PROCESSING, STORAGE AND DISPLAY;

U.S. patent application Ser. No. 16/209,395, titled METHOD OF HUB COMMUNICATION;

U.S. patent application Ser. No. 16/209,403, titled METHOD OF CLOUD BASED DATA ANALYTICS FOR USE WITH THE HUB;

U.S. patent application Ser. No. 16/209,407, titled METHOD OF ROBOTIC HUB COMMUNICATION, DETECTION, AND CONTROL;

U.S. patent application Ser. No. 16/209,416, titled METHOD OF HUB COMMUNICATION, PROCESSING, DISPLAY, AND CLOUD ANALYTICS;

U.S. patent application Ser. No. 16/209,423, titled METHOD OF COMPRESSING TISSUE WITHIN A STAPLING DEVICE AND SIMULTANEOUSLY DISPLAYING THE LOCATION OF THE TISSUE WITHIN THE JAWS;

U.S. patent application Ser. No. 16/209,427, titled METHOD OF USING REINFORCED FLEXIBLE CIRCUITS WITH MULTIPLE SENSORS TO OPTIMIZE PERFORMANCE OF RADIO FREQUENCY DEVICES;

U.S. patent application Ser. No. 16/209,433, titled METHOD OF SENSING PARTICULATE FROM SMOKE EVACUATED FROM A PATIENT, ADJUSTING THE PUMP SPEED BASED ON THE SENSED INFORMATION, AND COMMUNICATING THE FUNCTIONAL PARAMETERS OF THE SYSTEM TO THE HUB;

U.S. patent application Ser. No. 16/209,447, titled METHOD FOR SMOKE EVACUATION FOR SURGICAL HUB;

U.S. patent application Ser. No. 16/209,453, titled METHOD FOR CONTROLLING SMART ENERGY DEVICES;

U.S. patent application Ser. No. 16/209,458, titled METHOD FOR SMART ENERGY DEVICE INFRASTRUCTURE;

U.S. patent application Ser. No. 16/209,465, titled METHOD FOR ADAPTIVE CONTROL SCHEMES FOR SURGICAL NETWORK CONTROL AND INTERACTION;

U.S. patent application Ser. No. 16/209,478, titled METHOD FOR SITUATIONAL AWARENESS FOR SURGICAL NETWORK OR SURGICAL NETWORK CONNECTED DEVICE CAPABLE OF ADJUSTING FUNCTION BASED ON A SENSED SITUATION OR USAGE;

U.S. patent application Ser. No. 16/209,490, titled METHOD FOR FACILITY DATA COLLECTION AND INTERPRETATION; and U.S. patent application Ser. No. 16/209,491, titled METHOD FOR CIRCULAR STAPLER CONTROL ALGORITHM ADJUSTMENT BASED ON SITUATIONAL AWARENESS.

Before explaining various aspects of surgical devices and systems in detail, it should be noted that the illustrative examples are not limited in application or use to the details of construction and arrangement of parts illustrated in the accompanying drawings and description. The illustrative examples may be implemented or incorporated in other aspects, variations, and modifications and may be practiced or carried out in various ways. Further, unless otherwise indicated, the terms and expressions employed herein have been chosen for the purpose of describing the illustrative examples for the convenience of the reader and are not for the purpose of limitation thereof. Also, it will be appreciated that one or more of the following-described aspects, expressions of aspects, and/or examples, can be combined with any one or more of the other following-described aspects, expressions of aspects and/or examples.

Various surgical systems and instruments (e.g. surgical stapling instrument, surgical clip applier, surgical suturing instrument) are described in connection with the present disclosure. The surgical systems and/or instruments comprise a radio-frequency identification (RFID) system that includes one or more RFID scanners and one or more RFID tags, as will be discussed in greater detail below. Examples of surgical systems which use RFID technology are disclosed in U.S. Pat. No. 7,959,050 and U.S. Patent Application No. 2015/0053743, both of which are incorporated by reference herein in their entireties.

Radio-frequency identification (RFID) is used in a variety of industries to track and identify objects. RFID relies on radio waves to transfer digitally-stored information from a RFID tag to a RFID reader or receiver configured to receive the information. RFID technology uses RFID tags, sometimes referred to as chips, which contain electronically-stored information, and RFID readers, which serve to identify and communicate with the RFID tags. There are two different types of RFID systems—active RFID systems and passive RFID systems. Active RFID systems include RFID tags that comprise an on-board power source to broadcast their signals. Active RFID tags can include a battery within the RFID tag which allows the active RFID tag to function independently from the RFID reader. As such, RFID tags in an active RFID system do not need to wait to receive a signal from a RFID reader before sending out information. Instead, the active RFID tags are free to continuously send out a signal, or beacon. Many commercially available active RFID systems often operate at one of two main frequency ranges—433 MHz and 915 MHz, but any suitable frequency range can be used. Typically, a RFID tag must be within a specific distance or frequency range in order to be identified by its corresponding RFID reader.

Passive RFID systems include RFID tags which do not comprise an on-board power source but instead receive the energy needed to operate from an RFID reader. Contrary to active RFID tags, RFID tags in a passive RFID system do not actively send out a signal before receiving a prompt. Instead, passive RFID tags wait to receive information from a RFID reader before sending out a signal. Many commercially-available passive RFID systems often operate within three frequency ranges—Low Frequency ("LF"), High Frequency ("HF") & Near-Field Communication ("NFC"), and Ultra High Frequency ("UHF"). The LF bandwidth is 125-134 KHz and includes a longer wavelength with a short read range of approximately one to ten centimeters. The HF and NFC bandwidth is 13.56 MHz and includes a medium wavelength with a typical read range of one centimeter to one meter. The UHF bandwidth is 865-960 MHz and includes a short, high-energy wavelength of one meter which translates into a long read range. The above being said, any suitable frequency can be used.

A variety of RFID systems comprising differently-sized RFID tags exist. However, some are better suited for use in technology areas that require the tracking of very small objects. For example, Hitachi Chemical Co. Ltd. is a leading manufacturer in the RFID technology field. The Ultra Small size UHF RFID tag manufactured by Hitachi Chemical Co. Ltd. is typically no larger than 1.0 to 13 mm and enables communication between a RFID tag and a RFID reader at distances of several centimeters or more. Due to its compact nature, the Hitachi RFID tag is suitable for very small products which need to be identified. Each Hitachi RFID tag comprises an antenna, an IC chip connected to the antenna, and a sealing material that seals the IC chip and the antenna. Because the Hitachi RFID tag incorporates an antenna and an IC chip in a single unit, the Hitachi RFID tag is convenient enough to easily affix to any small object using an adhesive or tape, for example.

The Hitachi RFID tag comprises a square stainless steel plate and a metal antenna. The antenna comprises a LC resonant circuit or any other suitable circuit and is electrically connected to the plate. After the plate and the antenna are connected to one another, the antenna and plate are sealed together in a single unit with a sealing material. The sealing material is primarily composed of epoxy, carbon, and silica to enhance the heat resistance capabilities of the Hitachi RFID tag. That is, the heat resistance of the RFID tag substantially depends on the heat resistance capabilities of the sealing material. The sealing material has a high heat resistance withstanding temperatures of up to 250 to 300° C. for shorter time periods, such as a few seconds, and is resistant to heat for longer periods of time up to 150° C. Accordingly, the Hitachi RFID tag has a higher heat resistance than conventional RFID tags and can still operate normally even at high temperatures. Additional information regarding the Hitachi RFID tag can be found in U.S. Pat. No. 9,171,244, which is incorporated by reference herein in its entirety.

During various surgical procedures, a surgical instrument comprising at least one replaceable component are used. It is important that such replaceable components be replaced with functional and/or compatible components. Various identification systems described in greater detail herein verify, among other things, a component's compatibility with the surgical instrument and/or verify an operating status of the component. For instance, a controller and/or an identification system can serve to, for example, ensure that the packaging containing the replaceable component has not been destroyed and/or tampered with, alert a clinician if a component is compatible or incompatible with the surgical instrument, alert the clinician if the replaceable component is expired, and/or alert the clinician if a recall exists for a particular manufacturing batch and/or type of the replaceable component.

The identification systems described herein can either be active systems or passive systems. In various embodiments, a combination of active and passive identification systems are used. Passive systems can include, for example, a barcode, a quick response (QR) code, and/or a radio frequency identification (RFID) tag. Passive systems do not comprise an internal power source, and the passive systems described herein require a reader and/or scanner to send a first signal, such as an interrogation signal, for example.

Passive radio frequency identification (RFID) systems communicate information by using radio frequencies. Such passive RFID systems comprise an RFID scanner and an RFID tag with no internal power source. The RFID tag is powered by electromagnetic energy transmitted from the RFID scanner. Each RFID tag comprises a chip, such as a microchip, for example, that stores information about the replaceable component and/or a surgical instrument with which the replaceable component is compatible. While the chip may only contain an identification number, in various instances, the chip can store additional information such as, for example, the manufacturing data, shipping data, and/or maintenance history. Each RFID tag comprises a radio antenna that allows the RFID tag to communicate with the RFID scanner. The radio antenna extends the range in which the RFID tag can receive signals from the RFID scanner and transmit response signals back to the RFID scanner. In a passive RFID system, the RFID scanner, which also comprises its own antenna, transmits radio signals that activate RFID tags that are positioned within a pre-determined range. The RFID scanner is configured to receive the response signals that are "bounced back" from RFID tags, allowing the RFID scanner is to capture the identification information representative of the replaceable component. In various instances, the one or more response signals comprise the same signal as the interrogation signal. In various instances, the one or more response signals comprise a modified signal from the interrogation signal. In various instances, the RFID scanner is also able to write, or encode, information directly onto the RFID tag. In any event, the RFID scanner is able to pass information about the replaceable component to a controller, such as the control system of a surgical instrument and/or a remote surgical system. The RFID scanner is configured to read multiple RFID tags at once, as the RFID tags are activated by radio signals. Additionally, in certain instances, the RFID scanner is able to update, or rewrite, information stored on an RFID tag in signal range with the RFID scanner. The updates can, for example, be transmitted to the RFID scanner from a surgical hub, or any suitable server. Various surgical hubs are described in described in U.S. patent application Ser. No. 16/209,395, titled METHOD OF HUB COMMUNICATION, and filed Dec. 4, 2018, which is hereby incorporated by reference in its entirety.

Active radio frequency identification (RFID) systems also comprise an RFID tag and an RFID scanner. However, the RFID tag in an active RFID system comprises an internal power source. Active RFID systems utilize battery-powered RFID tags that are configured to continuously broadcast their own signal. One type of active RFID tag is commonly referred to as a "beacon." Such beacon RFID tags do not wait to receive a first signal from an RFID scanner. Instead, the beacon RFID tag continuously transmits its stored information. For example, the beacon can send out its information at an interval of every 3-5 seconds. Another type of active RFID tag comprises a transponder. In such systems, the RFID scanner transmits a signal first. The RFID transponder tag then sends a signal back to the RFID scanner with the relevant information. Such RFID transponder tag systems are efficient, as they conserve battery life when, for example, the RFID tag is out of range of the RFID scanner. In various instances, the active RFID tag comprises an on-board sensor to track an environmental parameter. For example, the on-board sensor can track moisture levels, temperature, and/or other data that might be relevant.

FIG. 1 illustrates various surgical instruments that are configured to receive various supplemental components that can be replaced during a surgical procedure. Such surgical instruments can benefit from the inclusion of at least one of the identification systems described herein, such as an RFID system. For example, a surgical stapling instrument 6100 comprises a handle 6110, an elongate shaft 6120 extending from the handle 6110, and an end effector 6130 extending from the elongate shaft 6120. The end effector 6130 comprises a first jaw 6132 and a second jaw 6134, wherein the second jaw 6134 is configured to receive a replaceable staple cartridge 6140. During a particular surgical procedure, a clinician may want to attach various supplemental components to the end effector 6130. Such supplemental components, or adjunct materials, are used to reinforce the staples and/or supplement the function of the staples. For example, a buttress, or tissue thickness compensator, 6165 may be attached to the first jaw 6132 and/or the second jaw 6134 to accommodate for varying tissue thicknesses. The addition of the buttress 6165 to the end effector 6130 can assist in forming a uniform staple line on the patient tissue, for example. In an effort to facilitate attachment of the buttress 6165 to the end effector 6130 and/or for storage, the buttress 6165 can be supported on a mounting member 6160. In various instances, the clinician can attach a layer of hemostatic agent 6175 to the first jaw 6132 and/or the second jaw 6134 of the end effector 6130 to promote rapid blood coagulation, among other things. The layer of hemostatic agent 6175 can improve the seal created by the staples, for example. In an effort to facilitate attachment of the layer of hemostatic agent 6175 to the end effector 6130 and/or for storage, the layer of hemostatic agent 6175 can be supported on a mounting member 6170. In various instances, the clinician can attach a layer of adhesive 6185 to the first jaw 6132 and/or the second jaw 6134 of the end effector 6130 to promote healing of the treated tissue and/or enhance the connection between two layers of tissue, among other things. The layer of adhesive 6185 can improve the seal created by the staples, for example. In an effort to facilitate attachment of the layer of adhesive can be supported on a mounting member 6180.

As described in greater detail herein, a first RFID tag 6162 is positioned on the mounting member 6160. The first RFID tag 6162 comprises stored information, wherein the stored information comprises data that identifies a characteristic of the buttress 6165 supported on the mounting member 6160. A second RFID tag 6172 is positioned on the mounting member 6170. The second RFID tag 6172 comprises stored information, wherein the stored information comprises data that identifies a characteristic of the layer of hemostatic agent 6175 supported on the mounting member 6170. A third RFID tag 6182 is positioned on the mounting member 6180. The third RFID tag 6182 comprises stored information, wherein the stored information comprises data that identifies a characteristic of the layer of adhesive 6185 supported on the mounting member 6180. The surgical stapling instrument 6100 further comprises an RFID scanner 6150. As discussed in greater detail herein, the RFID scanner 6150 can be positioned in any suitable location on the surgical instrument 6100 that allows the RFID scanner 6150 to communicate with the first RFID tag 6162, the second RFID tag 6172, and/or the third RFID tag 6182 as the supplemental component is being attached and/or after the supplemental component is attached to the end effector 6130.

A surgical clip applier 6200 comprises a handle 6210, an elongate shaft 6220 extending from the handle 6210, and an end effector 6230 extending from the elongate shaft 6220. The end effector 6230 comprises a first jaw 6232 and a second jaw 6234, wherein at least one of the first jaw 6232 and the second jaw 6234 is movable relative to one another during a clip crimping stroke. During a particular surgical procedure, a clinician may want to attach various supplemental components to the end effector 6230. For example, a clip 6260 comprising a first thickness may be loaded into the surgical clip applier 6200. The clip 6260 may be loaded individually into the surgical clip applier 6200 and/or the clip 6260 may be loaded into the surgical clip applier 6200 as a part of a clip cartridge. The attachment of the clip 6260 to the surgical clip applier 6200 can be beneficial when the patient tissue is thick and/or dense, for example. In various instances, the clinician can attach a clip 6290 comprising a second thickness to the surgical clip applier 6200. In various instances, the second thickness of the clip 6290 is smaller than the first thickness of the clip 6260. The attachment of the clip 6290 to the surgical clip applier 6200 can be beneficial when the patient tissue is thin and/or delicate, for example. In various instances, the clinician can attach a clip 6270 comprising a plurality of projections 6275 to the surgical clip applier 6200. The projections 6275 of the clip 6270 can serve to enhance the grip between the clip 6270 and the patient tissue and/or maintain the position of a crimped clip 6270 on the patient tissue, among other things. As shown on clip 6270, the projections 6275 may be attached to a thin clip. Utilization of the projections 6275 on the thin clip is beneficial when the patient tissue is thin and/or delicate, for example. In various instances, the clinician can attach a clip 6280 comprising a plurality of projections 6285 to the surgical clip applier 6200. The projections 6285 of the clip 6280 can serve to enhance the grip between the clip 6280 and the patient tissue and/or maintain the position of a crimped clip 6280 on the patient tissue, among other things. As shown on clip 6280, the projections 6285 may be attached to a thick clip. Utilization of the projections 6285 on the thick clip is beneficial when the patient tissue is thick and/or dense, for example.

As described in greater detail herein, a first RFID tag 6262 is positioned on the first clip 6260. The first RFID tag 6162 comprises stored information, wherein the stored information comprises data that identifies a characteristic of the clip 6260. A second RFID tag 6272 is positioned on the second clip 6270. The second RFID tag 6272 comprises stored information, wherein the stored information comprises data that identifies a characteristic of the second clip 6270. A third RFID tag 6282 is positioned on the third clip 6280. The third RFID tag 6282 comprises stored information, wherein the stored information comprises data that identifies a characteristic of the third clip 6280. A fourth RFID tag 6292 is positioned on the fourth clip 6290. The fourth RFID tag 6292 comprises stored information, wherein the stored information comprises data that identifies a characteristic of the fourth clip 6290. The surgical clip applier 6200 further comprises an RFID scanner 6250. As discussed in greater detail herein, the RFID scanner 6250 can be positioned in any suitable location on the surgical instrument 6200 that allows the RFID scanner 6250 to communicate with the first RFID tag 6262, the second RFID tag 6272, the third RFID tag 6282, and/or the fourth RFID tag 6292 as the supplemental component is being and/or after the supplemental component is attached to the suturing device 6200.

A surgical suturing device 6300 comprises a handle 6310, an elongate shaft 6320 extending from the handle 6310, and an end effector 6330 extending from the elongate shaft 6320. The end effector 6330 comprises a needle track configured to receive a portion of a replaceable needle. During a particular surgical procedure, a clinician may want to attach various supplemental components to the end effector 6330. Different knot tying mechanisms and/or different suture termination elements can be used to finish a line of sutures instead of tying a knot laparoscopically. For example, a needle 6360 comprising a first thickness may be loaded into the end effector 6330. The needle 6360 comprises a first end 6364 and a second end 6366. The first end 6364 comprises a pointed tip that comprises a first degree of sharpness. The second end 6366 comprises a suturing material 6365 attached thereto. The attachment of the shaft needle 6360 to the end effector 6330 can be beneficial when the patient tissue is thick and/or dense, for example. In various instances, the clinician can attach a needle 6370 comprising a second thickness to the end effector 6330. In various instances, the second thickness of the clip 6370 is smaller than the first thickness of the clip 6360. The clip 6370 further comprises a first end 6374 comprising a pointed tip that comprises a second degree of sharpness. In various instances, the second degree of sharpness of the clip 6370 is less than the first degree of sharpness of the clip 6360. The second end 6376 comprises a suturing material 6375 attached thereto. The attachment of the needle 6370 to the end effector 6330 can be beneficial when the patient tissue is thin and/or delicate, for example. In various instances, the clinician can select a particular suturing material to be attached to the replaceable needle. For example, a first suturing material 6385 can be made of a first material, comprise a first length, and/or comprise a first thickness. The first suturing material 6385 can be stored in a first packaging 6380 prior to attachment to a replaceable needle. A second suturing material 6395 can be made of a second material, comprise a second length, and/or comprise a second thickness. The second suturing material 6395 can be stored in a second packaging 6390 prior to attachment to a replaceable needle.

As described in greater detail herein, a first RFID tag 6362 is positioned on the first replaceable needle 6360. The first RFID tag 6362 comprises stored information, wherein the stored information comprises data that identifies a characteristic of the replaceable needle 6360 and/or the suturing material 6365 attached thereto. A second RFID tag 6372 is positioned on the second replaceable needle 6370. The second RFID tag 6372 comprises stored information, wherein the stored information comprises data that identifies a characteristic of the second replaceable needle 6370 and/or the suturing material 6375 attached thereto. A third RFID tag 6382 is positioned on the packaging 6380 of the third suturing material 6385. The third RFID tag 6382 comprises stored information, wherein the stored information comprises data that identifies a characteristic of the third suturing material 6385. A fourth RFID tag 6392 is positioned on the packaging 6390 of the fourth suturing material 6395. The fourth RFID tag 6392 comprises stored information, wherein the stored information comprises data that identifies a characteristic of the fourth suturing material 6390. The surgical suturing device 6300 further comprises an RFID scanner 6350. As discussed in greater detail herein, the RFID scanner 6350 can be positioned in any suitable location on the surgical instrument 6300 that allows the RFID scanner 6350 to communicate with the first RFID tag 6362 and/or the second RFID tag 6372 as one of the replaceable needles 6360, 6370 is being positioned and/or after the replaceable needle is positioned within the needle track of the end effector 6330 and/or to communicate with the third RFID tag 6382 and/or the fourth RFID tag 6392 when the packaging 6380, 6390 is brought within a pre-defined distance from the RFID scanner 6300.

Supplemental components, such as, for example, the buttress 6165, the hemostatic agent 6175, and/or the adhesive 6185, are contained within a sealed packaging after being manufactured until the packaging in opened in the operating room. In various instances, the supplemental component is supported on a mounting member within the packaging, for example, to facilitate storage and/or facilitate attachment of the supplemental component to the surgical instrument. Various forms of packaging include, for example, peel-pouches, woven and/or non-woven material wrappers, and rigid containers.

Figure 2:
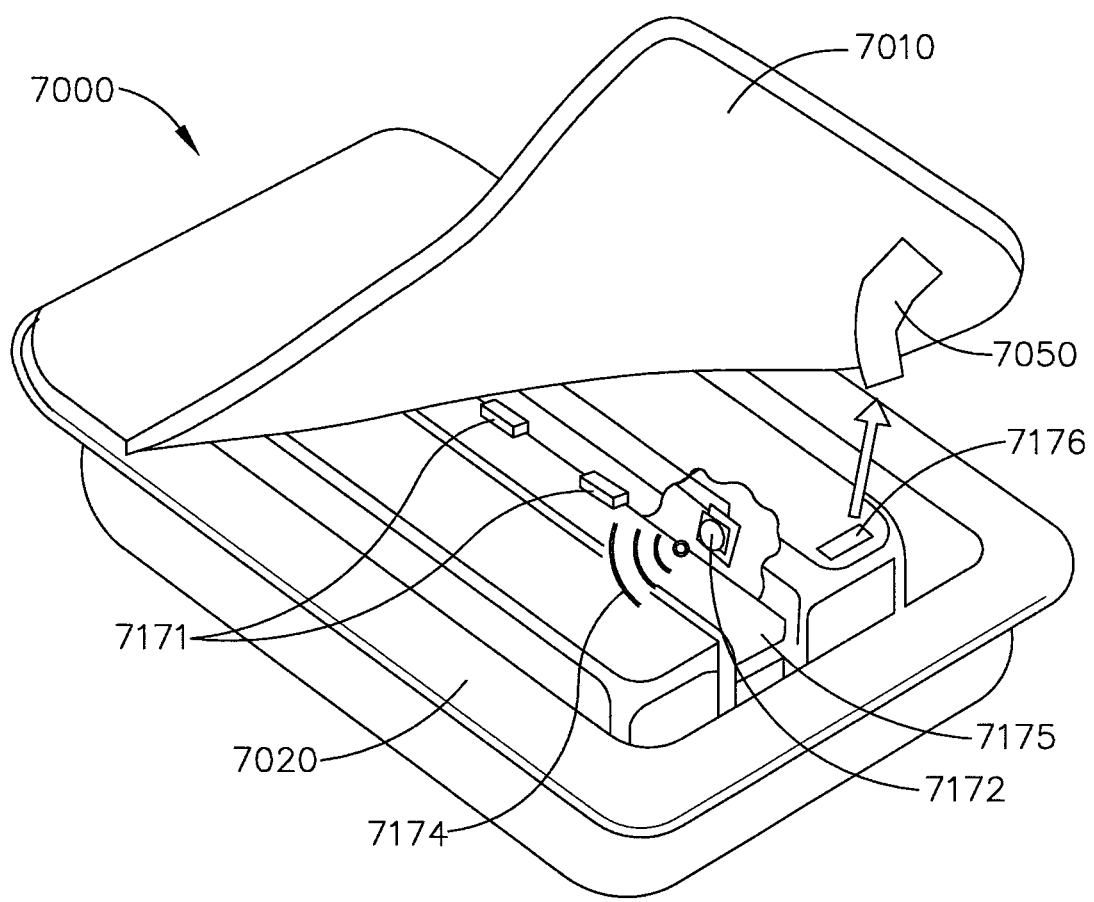
FIG. 2 is a perspective view of a packaging, wherein the packaging comprises an identifying characteristic of the supplemental component contained therein.

FIG. 2 depicts an example of a sealed packaging 7000. The depicted packaging 7000 is a peel-pouch. The packaging 7000 comprises a first layer 7010 and a second layer 7020. The first layer 7010 and the second layer 7020 form a protective barrier around a layer of hemostatic agent 7175, which is configured to be attached to a surgical staple cartridge. The layer of hemostatic agent 7175 is supported on a mounting member 7170 prior to the attachment of the layer of hemostatic agent 7175 to a surgical instrument. The mounting member 7170 comprises retention members 7171 configured to receive a portion of the layer of hemostatic agent 7175 and to, for example, facilitate alignment of the layer of hemostatic agent 7175. An adhesive bonds the first layer 7010 and the second layer 7020 together to form an airtight and/or fluid-tight seal and/or pouch around the layer of hemostatic agent 7175. The adhesive forms a seal without creases, wrinkles, and/or gaps. The seal created by the adhesive prevents contaminants from coming into contact with the layer of hemostatic agent 7175 and/or prevents components of the layer of hemostatic agent 7175 from being misplaced, for example. In various instances, the hemostatic agent 7175 is hermetically sealed within the packaging 7000. In various instances, the packaging 7000 provides a completely fluid-tight and airtight seal.

The first layer 7010 and the second layer 7020 are comprised of a material such as, for example, paper with a laminated inner surface. The laminated inner surface provides a barrier to prevent contaminants from entering the sealed portion of the packaging 7000. In various instances, the first layer 7010 and the second layer 7020 are comprised of plastic. The first layer 7010 and the second layer 7020 can be comprised of a material with a particular degree of transparency to allow a clinician, for example, to observe the contents of the packaging 7000 prior to breaking the seal. The above being said, any suitable material and/or combinations of materials can be used for the first layer 7010 and/or the second layer 7020. The first layer 7010 comprises a first portion positioned outside of the seal, and the second layer 7020 comprises a second portion positioned outside of the seal. The clinician can expose the sealed layer of hemostatic agent 7175 by holding the first portion and the second portion in separate hands and pulling the first portion in a direction away from the second layer 7020, although any suitable opening method can be used.

FIG. 2 depicts an RFID system 7500 integrated with the packaging 7000. The RFID system 7500 comprises an RFID tag 7172 and an insulator 7050. The RFID tag 7172 comprises a chip, such as a microchip, for example, that stores information about the packaging 7000 and/or the contents of the packaging 7000. In various instances, the chip comprises an identification number. Such an identification number can be assigned to the chip that can communicate the chip's existence to an RFID scanner. In various instances, the chip comprises additional information such as, for example, manufacturing data, shipping data, and/or compatibility data. The RFID tag 7172 further comprises a radio antenna 7173 configured to facilitate communication between the RFID tag 7172 and the RFID scanner.

The insulator 7050 is attached to the first layer 7010 of the packaging 7000, while the RFID tag 7172 is attached to a mounting member 7170 supporting the layer of hemostatic agent 7175. When the packaging 7000 is in a sealed configuration, the insulator 7050 is affixed to, or otherwise connected to an integrated battery 7176 of the RFID tag 7172. The integrated battery 7176 is activated when the packaging 7000 is opened. Prior to the packaging 7000 being opened, the interface between the insulator 7050 and the integrated battery 7176 prevents the integrated battery 7176 from providing power to the RFID tag 7172. In such instances, the RFID tag 7172 is unable to emit a signal. When a clinician breaks the seal of the packaging 7000 by peeling the first layer 7010 away from the second layer 7020, the insulator 7050 is disconnected, or otherwise disassociated, from the integrated battery 7176 of the RFID tag 7172. Upon disassociation of the insulator 7050 from the integrated battery 7176, the circuit between the integrated battery 7176 and the RFID tag 7172 is closed, and the RFID tag 7172 is energized. As shown in FIG. 2, the RFID tag 7172 begins emitting a signal 7174 upon being energized. The RFID tag 7172 is configured to emit the signal 7174 at any appropriate frequency and/or for any appropriate duration. For example, the RFID tag 7172 can continuously emit the signal 7174 or the RFID tag 7172 can emit the signal 7174 every 3-5 seconds. The signal 7174 comprises some, or all, of the information stored on the chip of the RFID tag 7172. In various instances, the signal 7174 may serve to alert a surgical instrument that the packaging 7000 has been tampered with during shipping and/or storage or simply that the packaging 7000 has been unsealed, for example.

Figure 4:
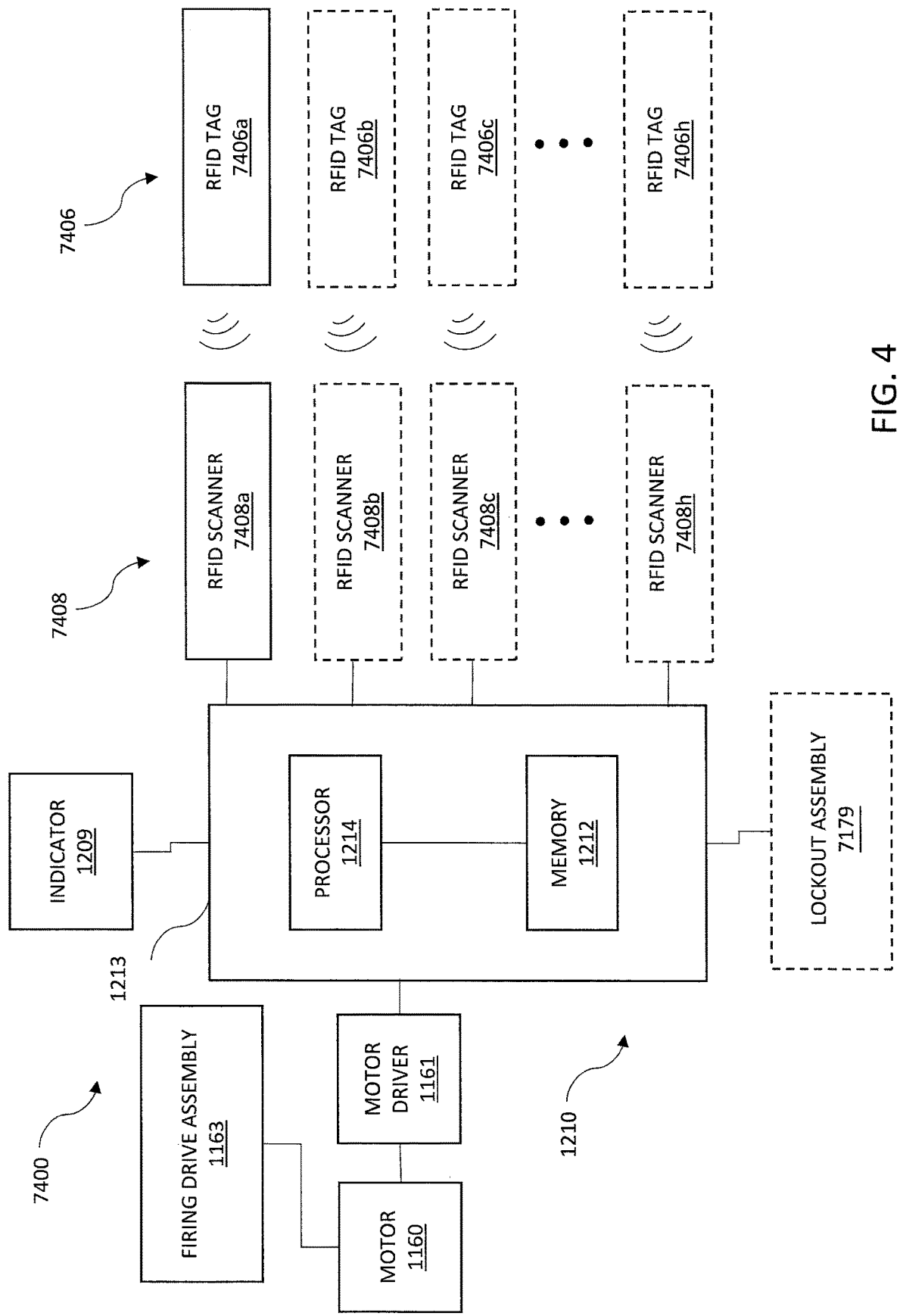
FIG. 4 is a representation of an RFID system for use with the surgical instruments disclosed herein.

FIG. 4 illustrates a block diagram of an RFID system and/or control system 7400 of the surgical stapling instrument and/or tool 7100; however the control system 7400 can be adapted for use with alternative surgical instruments and/or tools, such as the surgical clip applier 7200 and/or the surgical suturing device 7300 described in greater detail herein. The control system 7400 includes a control circuit 1210 that can be integrated with the RFID scanner, such as RFID scanner 7408a or can be coupled to, but positioned separately from, the RFID scanner 7408a. The control circuit 1210 can be configured to receive input from the RFID scanner 7408a indicative of the information stored in the RFID tag 7406a about the supplemental component 7175 and/or information about the packaging 7000 of the supplemental component 7175. In various instances, the RFID system 7400 comprises more than one RFID scanner 7408b-h and/or more than one RFID tag 7406b-h. The RFID scanners 7408a-h are communicably coupled to that the control circuit 1210 can receive data from the RFID scanners 7408a-h and then take various actions based upon the read data, as are described below.

In at least one example, the control circuit 1210 includes a microcontroller 1213 that has a processor 1214 and a storage medium such as, for example, a memory 1212. The memory 1212 stores program instructions for performing various processes such as, for example, identity verification. The program instructions, when executed by the processor 1214, cause the processor 1214 to verify the identity of the packaging 7000 and/or the supplemental component 7175 by comparing the identification information received from the RFID tag(s) 7406a-h to identification information stored in the memory 1212 in the form of an identity database or look-up table, for example. In various examples, the memory 1212 comprises a local memory of the instrument 7100. In other examples, identity databases or tables and/or compatibility databases or tables can be downloaded from a remote server. In various aspects, the instrument 7100 may transmit the information received from RFID tag(s) 7406a-7406h to a remote server that stores the databases or tables for performing the identity and/or compatibility checks remotely.

The RFID tag 7172 is configured to communicate with an RFID scanner. Once the insulator 7050 has been removed, the integrated battery 7176 of the RFID tag 7172 allows the RFID tag 7172 to emit the signal 7174 prior to receiving a first signal, such as an interrogation signal, from the RFID scanner. The RFID scanner comprises a scanner antenna configured to transmit and/or receive radio signals 7174 from the RFID tag 7172. In various instances, the RFID scanner comprises reading and writing capabilities. The RFID scanner is configured to pass the collected information from the RFID tag 7172 to a controller of the surgical instrument for further interpretation. In various instances, the controller is configured to determine if the supplemental component is compatible with the particular surgical instrument. In various instances, the controller is configured to activate a lockout assembly 7179 to prevent the surgical instrument from performing a function with the firing drive assembly 1163 such as, for example, a staple firing stroke, a suture firing stroke, and/or a clip crimping stroke if the controller determines that the supplemental component is not compatible with the particular surgical instrument and/or for use during the particular surgical procedure. Various lockout assemblies are described in greater detail in U.S. Pat. No. 7,143,923, entitled SURGICAL STAPLING INSTRUMENT HAVING A FIRING LOCKOUT FOR AN UNCLOSED ANVIL, which issued on Dec. 5, 2006; U.S. Pat. No. 7,044,352, SURGICAL STAPLING INSTRUMENT HAVING A SINGLE LOCKOUT MECHANISM FOR PREVENTION OF FIRING, which issued on May 16, 2006; U.S. Pat. No. 7,000,818, SURGICAL STAPLING INSTRUMENT HAVING SEPARATE DISTINCT CLOSING AND FIRING SYSTEMS, which issued on Feb. 21, 2006; U.S. Pat. No. 6,988,649, SURGICAL STAPLING INSTRUMENT HAVING A SPENT CARTRIDGE LOCKOUT, which issued on Jan. 24, 2006; and U.S. Pat. No. 6,978,921, SURGICAL STAPLING INSTRUMENT INCORPORATING AN E-BEAM FIRING MECHANISM, which issued on Dec. 27, 2005, the disclosures of which are incorporated by reference herein in their entireties. The RFID scanner is positioned within a pre-determined range of the RFID tag 7172 that allows for the RFID scanner to be able to receive the emitted signal 7174 transmitted by the RFID tag 7172. Depending on the application, the RFID scanner can be positioned on a surgical instrument, on the contents of the packaging, and/or remotely located on a console, such as a remote surgical system in communication with the surgical instrument. Additionally, the controller can be located in any suitable location, such as, for example, the surgical instrument or on a remote console.

In various instances, the tag antenna of the RFID tag 7172 is destroyed and/or is otherwise rendered inoperable as the packaging 7000 is opened and/or after the packaging 7000 is opened. The RFID tag 7172 is unable to transmit and/or receive communication and/or signals from an RFID scanner when the tag antenna is inoperable. In such instances, the RFID scanner is configured to receive a first signal from the RFID tag 7172 before the packaging is opened. Once the RFID scanner receives the first signal, the controller of the surgical instrument is configured to authenticate the packaging 7000 and the contents of the packaging 7000. If the RFID scanner does not receive the first signal from the RFID tag 7172, the controller is configured to prevent the surgical instrument from performing a function with the firing drive assembly 1163. The failure of the RFID scanner to receive the first signal is indicative of a tampered packaging and/or an inauthentic packaging, among other things. In various instances, the tag antenna is still operable after the packaging 7000 is opened; however, the communication range of the tag antenna is diminished. In such instances, the diminished communication range prevents the RFID tag 7172 from receiving and/or transmitting communication to the RFID scanner.

In various instances, a switch is positioned between the RFID tag 7172 and the power source. The insulator 7050 biases the switch open when the packaging 7000 is in a sealed configuration, and the power source is unable to supply power to the RFID tag 7172. In such circumstances, the RFID tag 7172 is unable to communicate with the RFID scanner. When the packaging 7000 in an unsealed configuration, the insulator 7050 is disassociated from the RFID tag 7172, and the switch is closed. In such circumstances, the power source is able to supply power to the RFID tag 7172, and the RFID tag 7172 is able to communicate with the RFID scanner.

In various instances, an RFID system comprising an RFID tag mounted to the second layer 7020 of the packaging 7000 can be used. Further to the above, the RFID tag comprises an internal power source positioned on the second layer 7020 of the packaging 7000. An insulator, similar to the insulator 7050, is attached to the packaging 7000 and, when the packaging 7000 is opened, the RFID tag on the second layer 7020 is activated. The insulator is attached to, or otherwise associated with, the first layer 7010 of the packaging 7000. When the packaging 7000 is in a sealed configuration, the insulator 7050 is attached to, or otherwise connected to, the RFID tag on the second layer 7020 of the packaging 7000 and holds open the circuit between the integrated power source and the RFID tag. The interface between the insulator 7050 and the RFID tag prevents the power source from activating the RFID tag, and the RFID tag is unable to emit a signal. When a clinician breaks the seal of the packaging 7000 by peeling away the first layer 7010, for example, the insulator 7050 is disconnected, or otherwise disassociated, from the RFID tag and the circuit between the power source and the RFID tag is closed. At such point, the RFID tag is energized and begins to emit a signal.

In various instances, the RFID system 7500 further comprises a transponder. The transponder receives a first communication from an RFID scanner. In various instances, the first communication from the RFID scanner energizes the transponder to a degree sufficient for the transponder to communicate with the RFID tag. In various instances, the transponder is energized prior to receiving the first communication from the RFID scanner. In any event, the transponder is configured to automatically transmit a signal to the RFID tag upon hearing, or otherwise receiving, the first communication from the RFID scanner. The power source of the RFID tag energizes the RFID tag upon receiving the signal from the transponder, and the RFID tag is able to respond to the communication transmitted by the RFID scanner. The transponder serves to, among other things, preserve the battery life of the RFID tag until, for example, the RFID tag is within range of the RFID scanner.

As described in greater detail herein, it is valuable for a clinician to be able to verify the compatibility of a supplemental component for use with a particular surgical instrument and/or for use during a particular surgical procedure. For various reasons, it can be also be meaningful for a clinician to be able to ensure that the supplemental component has not been previously used and/or tampered with. The clinician may also want to confirm, for example, that the supplemental component is not contaminated, that the supplemental component is intact, and/or that the supplemental component comprises an acceptable composition and/or dimension.

Figure 3:
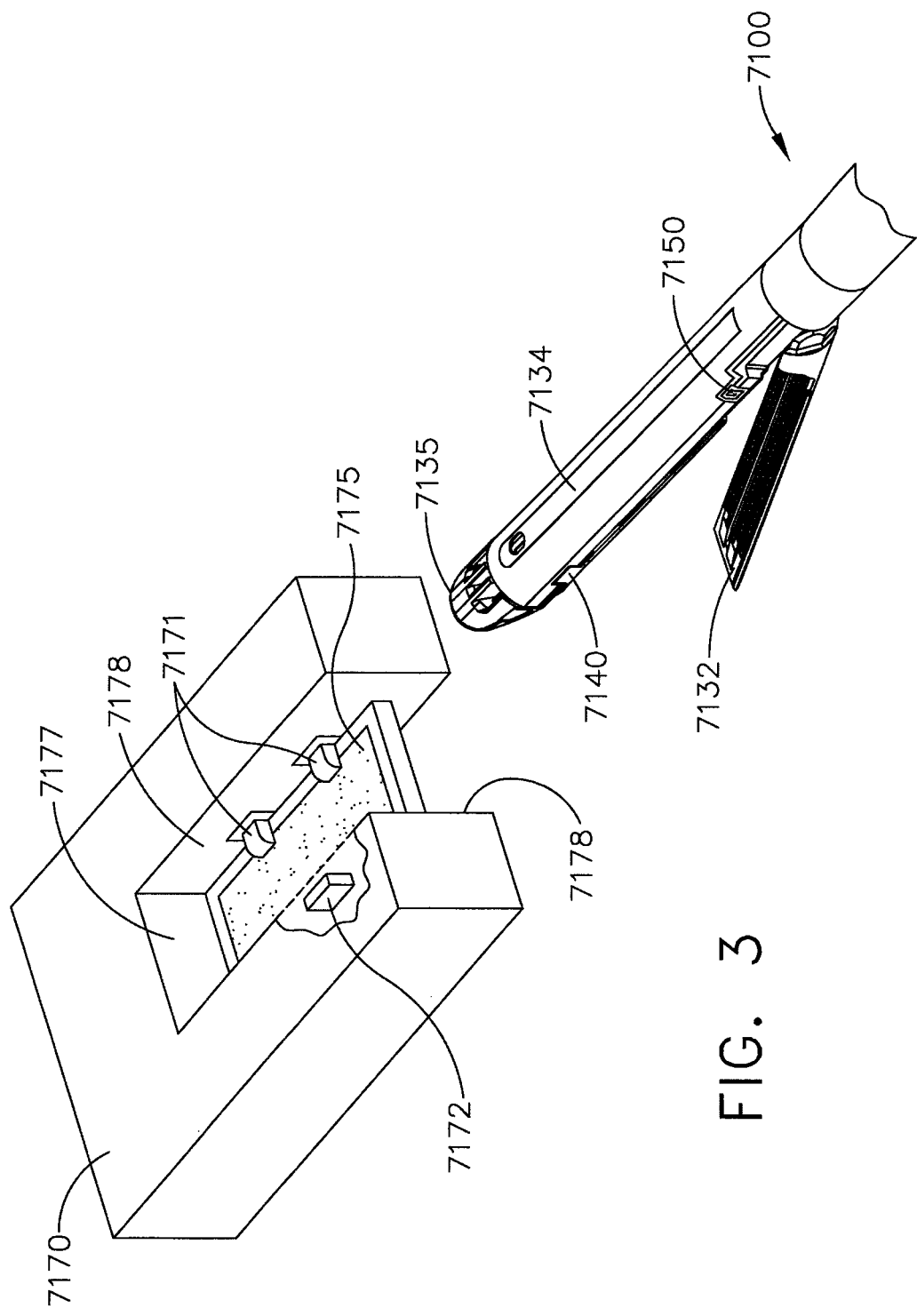
FIG. 3 is a partial cross-sectional view of a surgical stapling instrument system comprising a mounting member and a supplemental component, wherein the mounting member comprises an RFID tag.

FIG. 3 illustrates a portion of a surgical stapling instrument 7100. As discussed in greater detail elsewhere herein, the surgical stapling instrument 7100 comprises an end effector 7130 extending from an elongate shaft 7120 of the surgical stapling instrument 7100. The end effector 7130 comprises a first jaw 7132, wherein the first jaw 7132 is an anvil. The first jaw 7132 comprises a plurality of staple forming pockets. The end effector 7130 further comprises a second jaw 7134 comprising a channel configured to receive a replaceable staple cartridge 7140. The replaceable staple cartridge 7140 comprises a cartridge body and a plurality of staples removably stored within the cartridge body. The plurality of staples are driven out of the cartridge body during a staple firing stroke 1163. In an effort to, for example, promote rapid blood coagulation, of patient tissue affected during the staple firing and tissue cutting stroke 1163, the clinician can attach a layer of hemostatic agent 7175 to the end effector 7130 prior to performing the staple firing stroke 1163. In various instances, the layer of hemostatic agent 7175 is attached to a deck surface of the cartridge body. In various instances, the layer of hemostatic agent 7175 is attached to a tissue-supporting surface of the anvil. In any event, the layer of hemostatic agent 7175 is in contact with the patient tissue during and/or after the staple firing stroke 1163.

As discussed above, the layer of hemostatic agent 7175 is sealed within a packaging prior to attachment to the surgical instrument. Within the packaging, the layer of hemostatic agent 7175 is part of a mounting assembly configured to facilitate storage and attachment of the layer of hemostatic agent 7175. The mounting assembly comprises a mounting member 7170. In various instances, the mounting member 7170 provides a physical barrier between the layers of the packaging and the hemostatic agent 7175 and prevents the layers of the packaging from coming into contact with the hemostatic agent 7175. For example, the mounting member 7170 prevents the layer of hemostatic agent 7175 from sticking and/or otherwise adhering to one or both of the layers of the packaging. The layer of hemostatic agent 7175 is positioned between an opening within the mounting member 7170 defined by sidewalls 7177, 7188 of the mounting member 7170. The mounting member 7170 comprises retention members 7171 that receive a portion of the layer of hemostatic agent 7175. The retention members 7171 maintain the alignment of the layer of hemostatic agent 7175 and secure the layer of hemostatic agent 7175 to the mounting member 7170. The mounting member 7170 also provides a surface for the clinician to hold when aligning the layer of hemostatic agent 7175 for attachment to the end effector 7130 of the surgical instrument. The surface provided by the mounting member 7170 allows a clinician to attach the layer of hemostatic agent 7175 to the end effector 7130 without having to touch or otherwise contact the layer of hemostatic agent 7175.

The mounting member 7170 further comprises an RFID tag 7172. The RFID tag 7172 comprises a chip, such as a microchip, for example, that stores information about the mounting member 7170 and/or the layer of hemostatic agent 7175. In various instances, the set of stored information stored on the RFID chip comprises data that identifies the type of supplemental component the mounting member 7170 is supporting. In the depicted embodiment, the mounting member 7170 is supporting a layer of hemostatic agent 7175. However, the mounting member 7170 can support any suitable form of supplemental component such as, for example, a tissue thickness compensator and/or an adhesive. As shown in FIG. 3, the RFID tag 7172 is mounted to a sidewall 7178 of the mounting member 7170. However, the RFID tag 7172 can be embedded within and/or attached to the mounting member 7170 by any suitable method. In various instances, the RFID tag 7172 can be positioned on the layer of hemostatic agent 7175.

The RFID tag 7172 in the mounting member 7170 provides a lockout 7179 for the surgical instrument. The surgical instrument will not perform a function with the firing drive assembly 1163, such as a staple firing stroke and/or a jaw closure stroke, for example, if the information stored on the RFID tag 7172 is not received by a controller of the surgical instrument. In various instances, the surgical instrument will not perform the function with the firing drive assembly 1163 when the RFID tag 7172 is still in communication with an RFID scanner 7150 after the layer of hemostatic agent 7175 has been attached to the end effector 7130. Such a lockout 7179 prevents the surgical instrument from performing the function with the firing drive assembly 1163 when the mounting member 7170 is still attached to the layer of hemostatic agent 7175 and/or the layer of hemostatic agent 7175 has been inappropriately attached to the end effector 7130.

As mentioned in greater detail herein, the surgical stapling instrument 7100 comprises an RFID scanner 7150 configured to communicate with nearby RFID tags. The RFID scanner 7150 comprises a scanner antenna configured to transmit radio signals. The radio signals activate RFID tags that are positioned within a pre-determined range of the RFID scanner 7150. The RFID scanner 7150 then receives one or more response signals that are "bounced back" from the RFID tag(s). In various instances, the one or more response signals comprise the same signal as the interrogation signal. In various instances, the one or more response signals comprise a modified signal from the interrogation signal. In various instances, the RFID scanner 7150 comprises reading and writing capabilities. The RFID scanner 7150 is then able to pass the collected information from the RFID tag to a controller for further interpretation. The controller can be positioned in the surgical instrument, the remote console, or in any suitable location. The RFID scanner 7150 and/or the controller can comprise a stored set of information that corresponds to surgical stapling assemblies that are compatible with a particular surgical instrument and/or for use during a particular surgical procedure.

More specifically, the surgical system comprises an RFID scanner 7150 configured to interact with the RFID tag 7172 attached to the mounting member 7170. The RFID scanner 7150 can be present in various locations. For example, the RFID scanner 7150 can be retained by the staple cartridge 7140. In various instances, the RFID scanner is powered by the battery and/or power source of the surgical instrument. In the depicted embodiment, the RFID scanner 7150 is positioned on the second jaw 7134 of the end effector 7130; however, the RFID scanner 7150 can be located in an alternative location within the surgical system and/or any other suitable location that would allow for communication between the RFID tag 7172 and the RFID scanner 7150 when the mounting member 7170 is within a pre-determined range of the end effector 7130. The RFID scanner 7150 and/or the RFID tag 7172 are powered such that the signal(s) they emit can only be detected within a limited radius. That said, as the mounting member 7170 is removed from the layer of hemostatic agent 7175 after attaching the layer of hemostatic agent 7175 to the end effector 7130, the RFID tag 7172 is unable to communicate with the RFID scanner 7150.

In various instances, the end effector 7130 comprises an RFID scanner positioned on a distal end of the end effector 7130. An RFID tag is retained by a back wall 7177 of the mounting member 7170. During proper attachment of the supplemental component 7175 to the end effector 7130, the distal end of the end effector 7130 is brought close to, aligned with, and/or brought into contact with the back wall 7177 of the mounting member 7170. In various instances, the communication range of the RFID scanner spans a distance that only encompasses the RFID tag of the back wall 7177 of the mounting member 7170 when the end effector 7130 is brought close to and/or brought into contact with the back wall 7177. Such a communication range allows the RFID tag to communicate with the RFID scanner only when the supplemental component 7175 is fully aligned with the end effector 7130. The communication between the RFID tag and the RFID scanner can alert a clinician that the supplemental component 7175 is fully aligned with the end effector 7130 and a function with the firing drive assembly 1163 of the surgical instrument can be performed. If the RFID scanner does not receive a communication from the RFID tag, the supplemental component 7175 may be misaligned and/or not fully attached to the end effector 7130, for example, which can lead to the formation of a non-uniform staple line, for example. In various instances, the controller of the surgical instrument prevents the surgical instrument from performing a function with the firing drive assembly 1163, such as a staple firing stroke, for example. In various instances, if the RFID scanner continues to receive communication from the RFID tag when the clinician believes the supplemental component 7175 is attached to the end effector, the controller is configured to prevent the function with the firing drive assembly 1163 of the surgical instrument. The continued communication indicates that the mounting member 7170 is still attached to the supplemental component 7175. In such circumstances, the loss of communication indicates that the mounting member 7170 has been removed and/or moved out of communication distance from the end effector 7130 and/or the supplemental component 7175.

If the mounting member 7170 does not comprise an RFID tag and/or the RFID tag 7172 comprises information that is not compatible with the surgical instrument, the supplemental component verification system of the surgical instrument will be unable to permit the surgical instrument to perform a function with the firing drive assembly 1163, such as the staple firing stroke or the jaw closure stroke. If the RFID scanner 7150 receives a response to an interrogation signal that is not found within a stored set of compatible supplemental components, the controller of the surgical instrument is programmed to communicate an error to the clinician. Likewise, if the RFID scanner 7150 does not receive a response to the interrogation signal, the controller of the surgical instrument is programmed to communicate an error to the clinician. In various instances, the detection of an error by the controller can render the surgical instrument inoperable for use with that particular supplemental component. In various instances, a detected error can prevent the surgical instrument from performing a staple firing stroke, jaw closure stroke, and/or tissue cutting stroke. In various instances, the surgical instrument further comprises a manual override that can be activated to allow a clinician to override any system lockout 7179 and utilize operational functions of the surgical instrument in an emergency. As discussed above, the controller is configured to alert the clinician that an error has been detected by way of an indicator 1209. Such an alert can be communicated through various forms of feedback, including, for example, haptic, acoustic, and/or visual feedback. In at least one instance, the feedback comprises audio feedback, and the surgical instrument can comprise a speaker which emits a sound, such as a beep, for example, when an error is detected. In certain instances, the feedback comprises visual feedback and the surgical instrument can comprise a light emitting diode (LED), for example, which flashes when an error is detected. In various instances, the feedback comprises haptic feedback and the surgical instrument can comprise an electric motor 1160 comprising an eccentric element which vibrates when an error is detected. The alert can be specific or generic. For example, the alert can specifically state that the RFID tag 7172 on the mounting member 7170 is unable to be detected, or the alert can specifically state that the RFID tag 7172 comprises information representative of an incompatible and/or defective supplemental component 7175.

In various instances, the controller can be configured to select and/or modify various operational parameters based on the identification of the layer of hemostatic agent 7175 using the information stored on the RFID tag 7172. Such an identification can include the material the layer of hemostatic agent 7175 is comprised of and/or the thickness of the layer of hemostatic agent 7175, among other things. After identification of the layer of hemostatic agent 7175, the controller is configured to permit the surgical instrument to perform the desired function with the firing drive assembly 1163 using the modified operational parameters.

Figure 5:
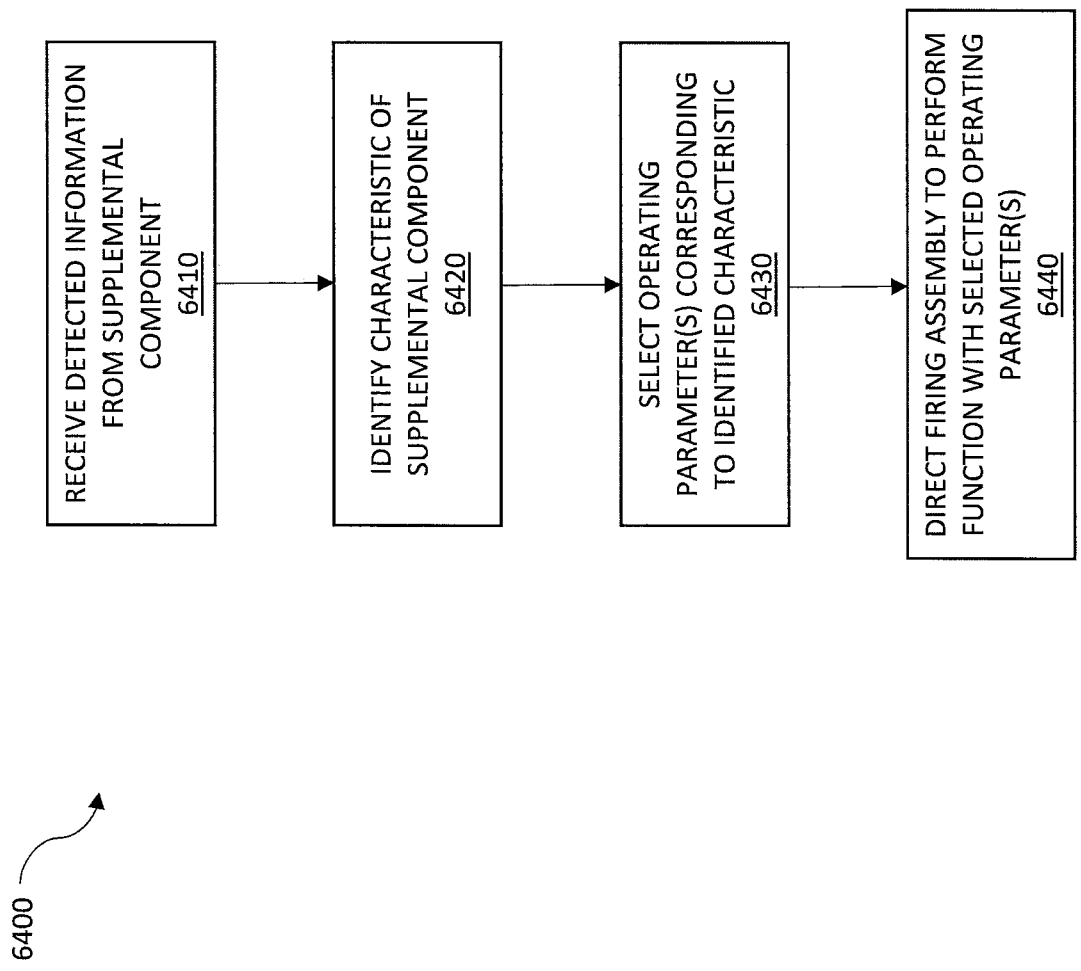
FIG. 5 is a flowchart representative of a process of a controller for modifying at least one operational parameter based on an identified supplemental component.

For example, FIG. 5 depicts an exemplary process 6400 of the control circuit 1210. As discussed above, the control circuit 1210 is configured to receive 6410 the information stored on the RFID tag 7172 corresponding to the supplemental component, such as the layer of hemostatic agent 7175. Using the received information, the control circuit 1210 is configured to identify 6420 a characteristic of the supplemental component 7175 using the received information. The control circuit 1210 is configured to select 6430 one or more appropriate operating parameters that correspond to the identified characteristic of the supplemental component 7175. The control circuit 1210 is configured to direct 6440 the firing assembly to perform a function, such as a staple firing stroke, with the selected operating parameter(s).

In various instances, and as discussed above, the RFID tag 7172 can comprise an integrated power source and become activated upon the opening of the packaging 7000. In such instances, the RFID tag 7172 can continuously transmit the stored set of information, and the RFID tag 7172 does not need to wait for an interrogation signal from the RFID scanner 7300 to transmit the stored set of information.

Figure 6:
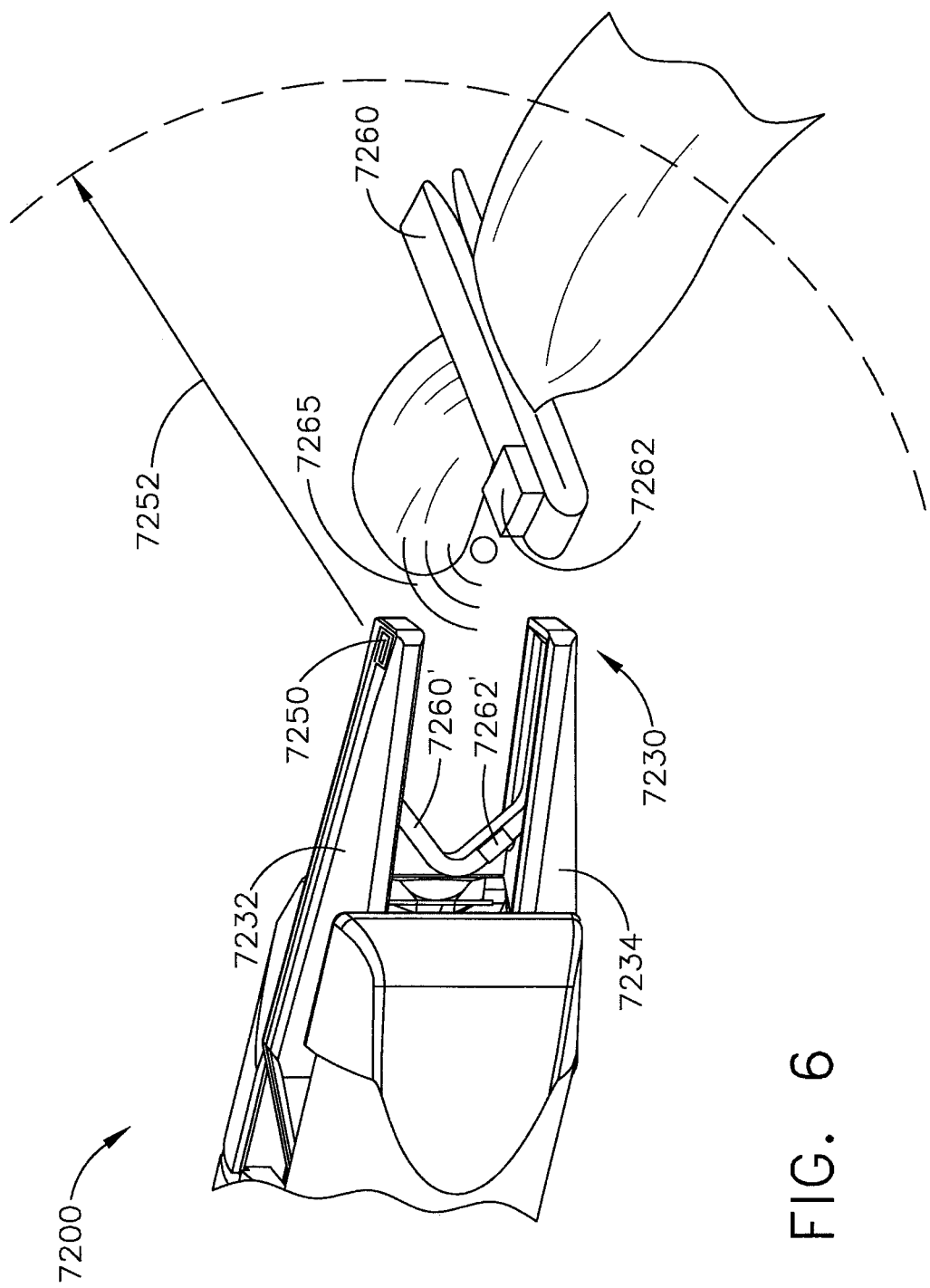
FIG. 6 is a partial perspective view of a surgical clip applier comprising an RFID system.

FIG. 6 illustrates a portion of a surgical clip applier 7200. As discussed in greater detail herein, the surgical clip applier 7200 comprises an end effector 7230. The end effector 7230 comprises a first jaw 7232 and a second jaw 7234. At least one of the first jaw and the second jaw are movable toward one another during a crimping stroke. The surgical clip applier 7200 further comprises at least one clip. In various instances, the surgical clip applier 7200 is configured to receive a cartridge comprising a plurality of clips. In other instances, the surgical slip applier 7200 is configured to receive one clip at a time. Each clip is configured to be crimped around patient tissue T one at a time during the crimping strokes.

The surgical clip applier 7200 is configured to receive a clip cartridge comprising a first clip 7260 and a second clip 7260'. The first clip 7260 comprises a first RFID tag 7262. The first RFID tag 7262 comprises a chip, such as a microchip, for example, that stores information about the surgical clip applier 7200, the first clip 7260, and/or the cartridge attached to the surgical clip applier 7200. In various instances, the set of information stored on the RFID chip comprises data that identifies the type of clip 7260 and/or clip cartridge attached to the surgical instrument 7200. As shown in FIG. 6, the first RFID tag 7262 is mounted to an outer surface of the first clip 7260. The first RFID tag 7262 is positioned on the outer surface of the first clip 7260 so that the first RFID tag 7262 is not in contact with patient tissue T when the first clip 7260 is crimped. Such placement can minimize damage and/or trauma to the patient tissue T, for example. The first RFID tag 7262 is positioned on a portion of the first clip 7260 that is not bent during the crimping stroke. Such placement avoids damaging the first RFID tag 7262 during the crimping stroke, for example. That said, the first RFID tag 7262 can be embedded within and/or attached to the first clip 7260 by any suitable method and/or at any suitable location.

The first RFID tag 7262 on the first clip 7260 provides a lockout for the surgical instrument, such as lockout 7179, for example. The clip applier will not perform a function with the firing drive assembly 1163, such as the crimping stroke on the first clip 7260, for example, if the information stored on the first RFID tag 7262 is not received by a controller of the surgical instrument. In various instances, the surgical instrument will not perform the function with the firing drive assembly 1163 when the first RFID tag 7262 is still in communication with an RFID scanner 7250 after the crimping stroke has been performed on the first clip 7260. As described in greater detail herein, the continued communication between the first RFID tag 7262 and the RFID scanner 7250 after the crimping stroke has been performed on the first clip 7260 indicates, among other things, that the clip applier is positioned too close to the formed first clip 7260. In various instances, the clip applier can alert a clinician of the detected location of the clip applier with respect to the formed first clip 7260 to prevent the clip applier from applying clips too close together, for example.

Figure 7:
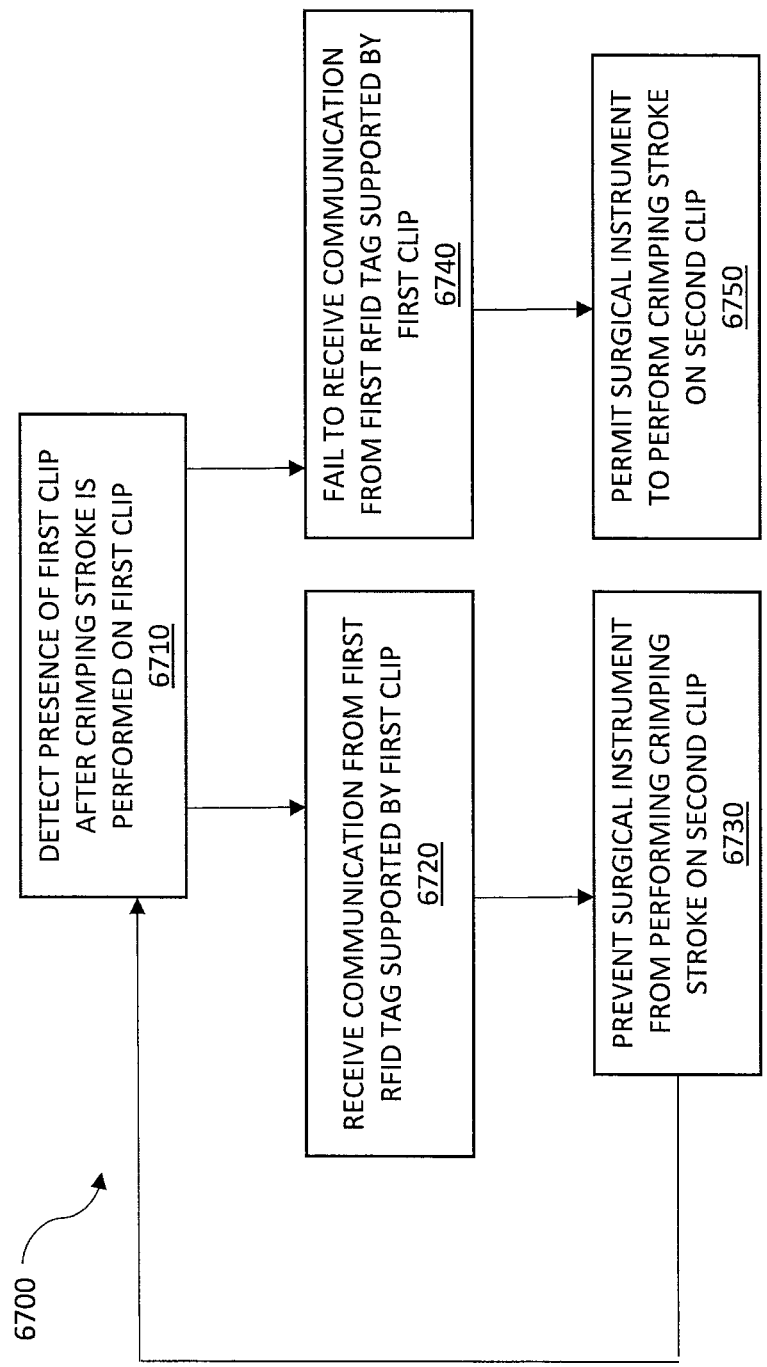
FIG. 7 is a flowchart representative of a process of a controller for controlling the performance of a crimping stroke based on the detection of an RFID tag.

For example, a process 6700 of the control circuit 1210 is depicted in FIG. 7. The control circuit 1210 is configured to detect 6710 the presence of a first clip after a crimping stroke is performed on the first clip. If the controller, through an RFID scanner, receives 6720 a communication and/or signal from the first RFID tag supported by the first clip, the controller is configured to prevent 6730 the surgical instrument 7200 from performing a crimping stroke on a second clip. If the controller, through the RFID scanner, fails to receive 6740 a communication and/or signal from the first RFID tag supported by the first clip, the controller is configured to permit 6750 the surgical instrument 7200 to perform the crimping stroke on the second clip.

Figure 8:
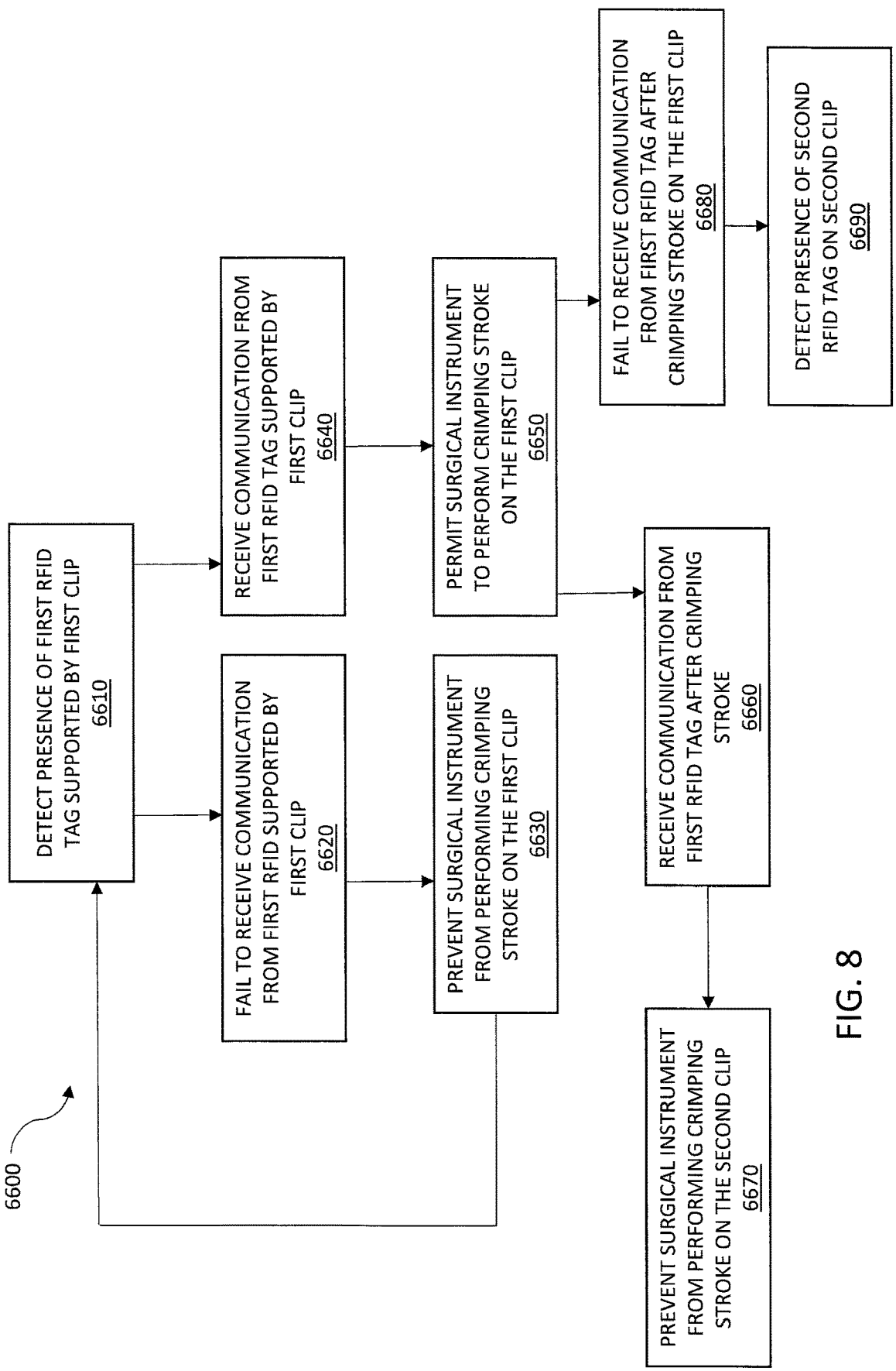
FIG. 8 is a flowchart representative of a process of a controller for controlling the performance of a crimping stroke based on the monitoring of multiple RFID tags.

An additional process 6600 of the control circuit 1210 is depicted in FIG. 8. The control circuit 1210 is configured to detect the presence of a first RFID tag supported by a first clip 6610. If the control circuit 1210 fails to receive a communication from the first RFID tag 6620, through an RFID scanner, the controller is configured to prevent the surgical instrument 7200 from performing a function 6630, such as a crimping stroke, on the first clip. The control circuit 1210 continues to detect the presence of the first RFID tag 6610 until the controller receives a communication from the first RFID tag 6640. Upon receiving the communication from the first RFID tag 6640, through the RFID scanner, the control circuit 1210 is configured to permit the surgical instrument 7200 to perform a crimping stroke on the first clip. After the crimping stroke is performed on the first clip, if the controller continues to receive communication from the first RFID tag 6660, the controller is configured to prevent the surgical instrument 7200 from performing a crimping stroke on a second clip 6670. After the crimping stroke is performed on the first clip, if the controller no longer receives communication from the first RFID tag 6680, the controller is configured to permit the surgical instrument 7200 to perform the crimping stroke on the second clip 6690.

As mentioned in greater detail herein, the surgical clip applier 7200 comprises an RFID scanner 7250 configured to communicate with nearby RFID tags. The RFID scanner 7250 comprises a scanner antenna configured to transmit radio signals. The radio signals activate RFID tags that are positioned within a pre-determined range of the RFID scanner 7250. The RFID scanner 7250 then receives one or more response signals that are "bounced back" from the RFID tag(s). In various instances, the one or more response signals comprise the same signal as the interrogation signal. In various instances, the one or more response signals comprise a modified signal from the interrogation signal. In various instances, the RFID scanner 7250 comprises reading and writing capabilities. The RFID scanner 7250 is then able to pass the collected information from the RFID tag to a controller for further interpretation. The controller can be positioned in the surgical instrument 7200, the remote console, or in any suitable location. The RFID scanner 7250 and/or the controller can comprise a stored set of compatibility information that corresponds to clip cartridges and/or clips that are compatible with a particular surgical instrument and/or for use during a particular surgical procedure.

More specifically, the surgical system 7200 comprises an RFID scanner 7250 configured to interact with the RFID tag 7262 attached to the first clip 7262. The RFID scanner 7250 can be present in various locations. In the depicted embodiment, the RFID scanner 7250 is positioned on the second jaw 7234 of the end effector 7230; however, the RFID scanner 7250 can be located in an alternative location within the surgical system 7200 and/or any other suitable location that would allow for communication between the first RFID tag 7262 and the RFID scanner 7250. The RFID scanner 7250 and/or the first RFID tag 7262 are powered such that the signal(s) they emit can only be detected within a communication range 7252 defined by a limited radius. That said, as the surgical clip applier 7200 is moved away from the patient tissue T where the first clip 7260 was applied, the first RFID tag 7262 is unable to communicate with the RFID scanner 7250. In such circumstances, the RFID tag 7262 moves outside of the communication range 7252 of the RFID scanner 7250. The RFID tag 7262 is unable to transmit and/or receive signals from the RFID scanner 7250 when the RFID tag 7262 is positioned outside of the communication range 7252.

If the first clip 7260 does not comprise an RFID tag and/or the first RFID tag 7262 comprises information that is not compatible with the surgical instrument 7200, the supplemental component verification system of the surgical instrument 7200 will be unable to permit the surgical instrument to perform a function with the firing drive assembly 1163, such as the crimping stroke. If the RFID scanner 7250 receives a response to an interrogation signal that is not found within a stored set of compatible supplemental components, the controller of the surgical instrument is programmed to communicate an error to the clinician. Likewise, if the RFID scanner 7250 does not receive a response to the interrogation signal, the controller of the surgical instrument is programmed to communicate an error to the clinician. In various instances, the detection of an error by the controller can render the surgical instrument inoperable for use with that particular clip cartridge and/or clip 7260. In various instances, a detected error can prevent the surgical instrument from performing a clip applying and/or crimping stroke. In various instances, the surgical instrument further comprises a manual override that can be activated to allow a clinician to override any system lockout 7179 and utilize operational functions of the surgical instrument in an emergency. As discussed above, the controller is configured to alert the clinician that an error has been detected through an indicator 1209. Such an alert can be communicated through various forms of feedback, including, for example, haptic, acoustic, and/or visual feedback. The alert can be specific or generic. For example, the alert can specifically state that the first RFID tag 7262 on the first clip 7260 is unable to be detected, or the alert can specifically state that the first RFID tag 7262 comprises information representative of an incompatible and/or defective clip cartridge and/or clip 7260.

Figure 9:
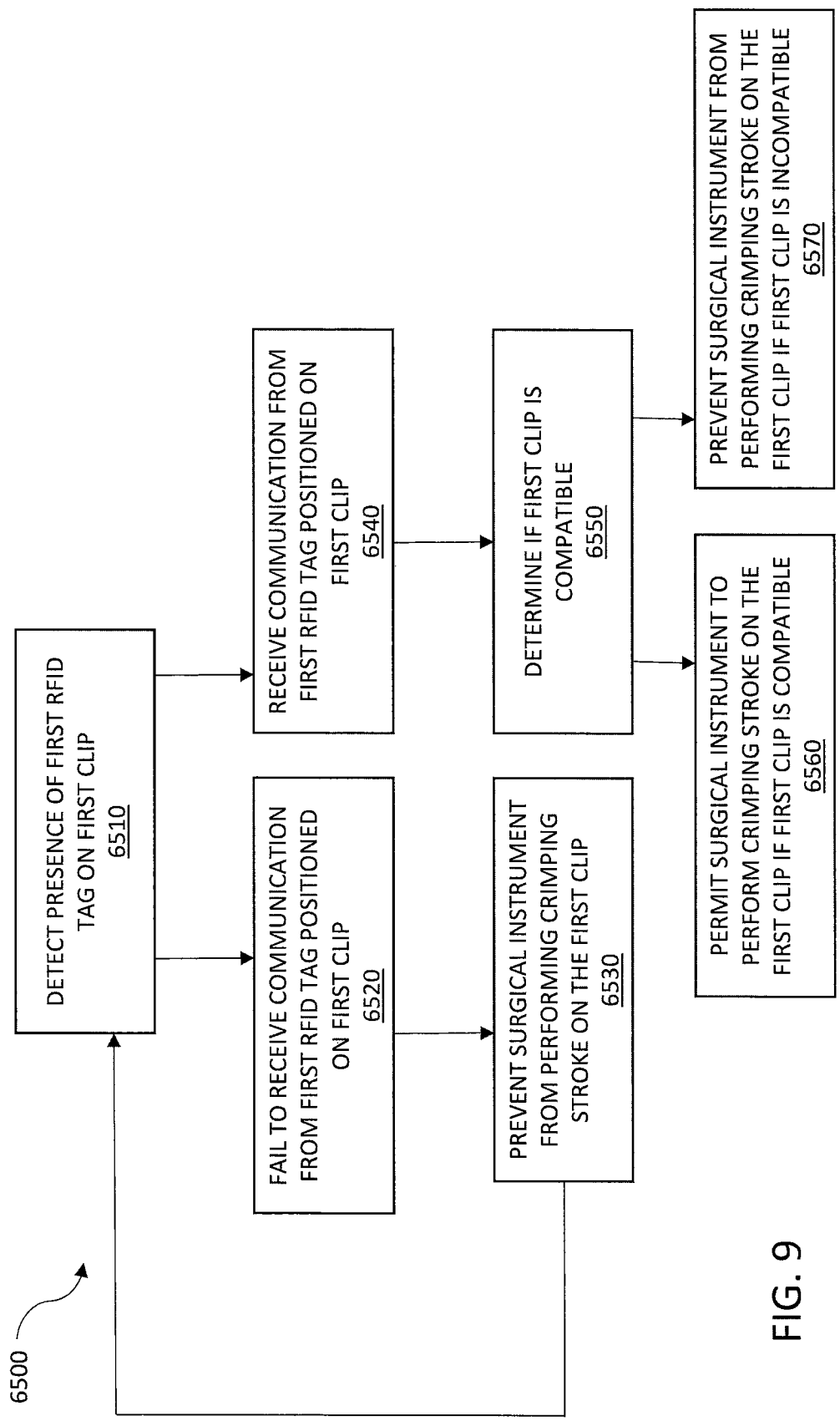
FIG. 9 is a flowchart representative of a process of a controller for detecting the compatibility of an attached clip.

For example, a process 6500 of the control circuit 1210 to determine authenticity and/or compatibility of the clips and/or the clip cartridge attached to the surgical instrument 7200 is depicted in FIG. 9. In instances where each clip comprises an RFID tag, the control circuit 1210 is configured to detect the presence of the first RFID tag supported by the first clip 6510 through an RFID scanner. If the RFID scanner fails to receive a communication from the first RFID tag, the RFID scanner is unable to pass along the communication to the control circuit 1210. In such instances, the control circuit 1210 fails to receive the information stored on the first RFID tag 6520, and the control circuit 1210 prevents the surgical instrument 7200 from performing a crimping stroke on the first clip 6530. The failure for the RFID scanner to detect the first RFID tag can arise from various scenarios such as an inauthentic clip, a defective clip, and/or an improperly aligned clip, among other things. If the RFID scanner receives a communication from the first RFID tag, the RFID scanner is configured to communicate the received information to the control circuit 1210. The control circuit 1210 determines if the first clip is compatible 6550 for use with the surgical instrument 7200 and/or during the surgical procedure. If the control circuit 1210 determines that the first clip is compatible for use, the control circuit 1210 permits the surgical instrument 7200 to perform a function 6560, such as a crimping stroke, on the first clip. If the control circuit 1210 determines that the first clip is incompatible for use, the control circuit 1210 prevents the surgical instrument 7200 from performing the function 6570.

In various instances, the controller can modify various operational parameters based on the identification of the clip cartridge and/or clip 7260 using the information stored on the first RFID tag 7262. Such an identification can include the material the first clip 7260 is comprised of, the number of clips 7260 remaining in the clip cartridge, the size of the clips 7260, and/or the thickness of the first clip 7260, among other things. After identification of the first clip 7260, the controller is configured to permit the surgical instrument to perform the desired function with the firing drive assembly 1163 using the modified operational parameters.

As discussed above, the RFID scanner 7250 comprises a communication range 7252 that spans a distance D from the RFID scanner 7250. When the first RFID tag 7262 on the first clip 7260 is located a distance away from the RFID scanner 7250 that is less than the distance D, the RFID scanner 7250 is able to transmit signals to and receive signals 7265 from the first RFID tag 7262. As discussed above, the surgical clip applier 7200 depicted in FIG. 6 further comprises the second clip 7260' comprising a second RFID tag 7260'. The second RFID tag 7260' comprises an RFID chip and a tag antenna, and the second RFID tag 7260' is similar in function and structure to the first RFID tag 7260. When the RFID scanner 7250 receives signals from both the first RFID tag 7260 and the second RFID tag 7260', the controller of the surgical clip applier 7200 is configured to alert the clinician. Such an alert can notify the clinician that the surgical clip applier 7200 is about to crimp the second clip 7260' in a location that is too close to the first formed clip 7260, for example. The controller can then prevent the clip applier 7200 from performing a crimping stroke on the second clip 7260' until the RFID scanner 7250 is unable to send and/or receive communications and/or signals from the first RFID tag 7262 on the first clip 7260.

In various instances, the information stored on the first RFID tag 7262 is a first serial number that is specific to the first clip 7260 and the information stored on the second RFID tag 7262' is a second serial number that is specific to the second clip 7260'. Based on the information received by the RFID scanner 7250, the controller is able to monitor each individual clip 7260, 7260' for compatibility with the surgical clip applier 7200 and/or authenticity, for example. In various instances, the controller is further able to maintain a count of the number of clips remaining in the loaded clip cartridge. In such instances, the controller is configured to alert the clinician of the number of clips remaining in the clip cartridge so that the clinician can prepare a new clip cartridge for attachment to the clip applier 7200.

Figure 10:
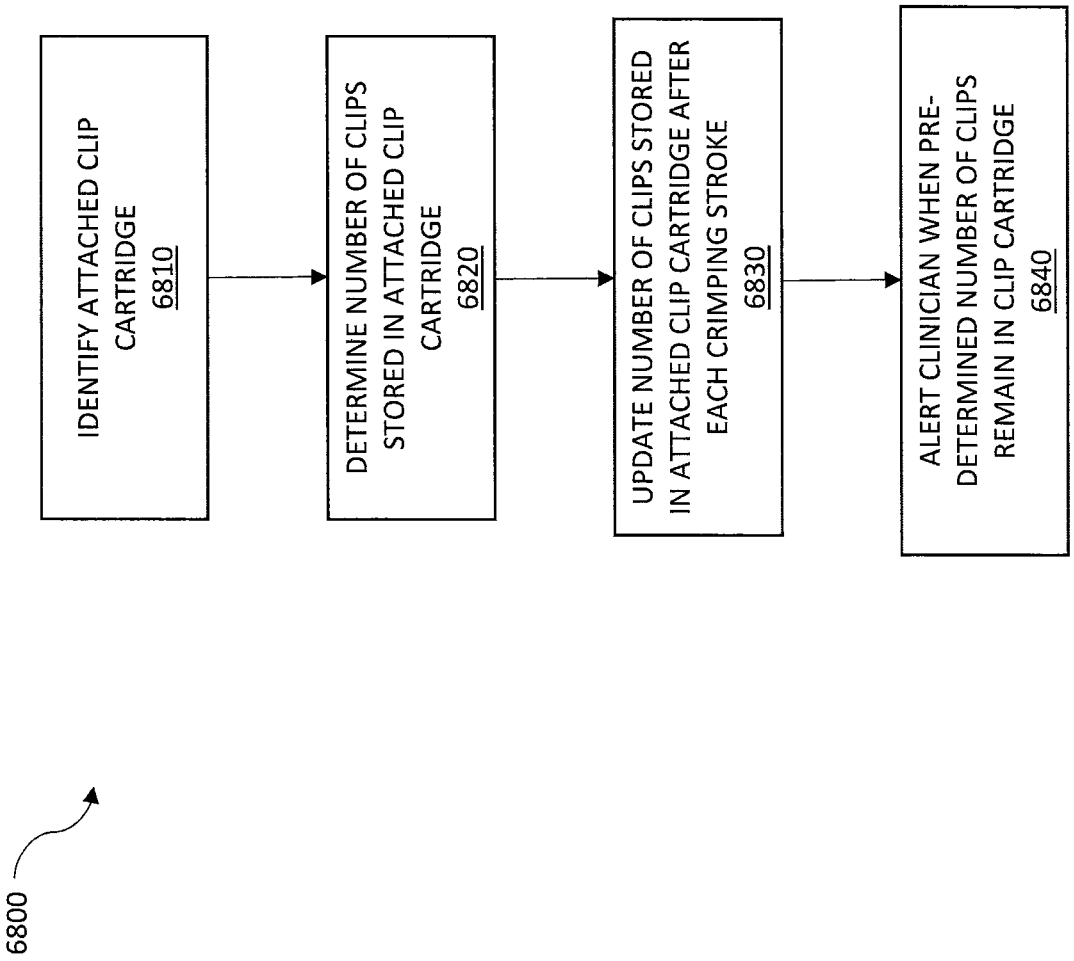
FIG. 10 is a flowchart representative of a process of a controller for monitoring the number of clips remaining in a clip cartridge.

For example, a process 6800 of the control circuit 1210 is depicted in FIG. 10. The control circuit 1210 is configured to identify a characteristic of a clip cartridge 6810 attached to the surgical instrument 7200. Using the identified characteristic, the control circuit 1210 is configured to determine a number 6820 of clips stored and/or remaining in the clip cartridge. The control circuit 1210 is configured to update the count of the number of clips 6830 stored and/or remaining in the clip cartridge after each crimping stroke. The control circuit 1210 is further configured to alert a clinician 6840 when a pre-determined number of clips remain in the clip cartridge. For example, the clinician can be alerted when only one clip remains in the clip cartridge. In various instances, the clinician can be continuously alerted of the clip count.

In various instances, individual surgical clip appliers, such as the clip appliers 6200 and 7200, are configured to be interchangeably used with various configurations of clips and/or clip cartridges. For example, clips can comprise different dimensions, different strengths, different harnesses, and/or different material compositions. Furthermore, the end effector 6230 can be removably attached to the elongate shaft 6220 to allow different end effector configurations to be attached to the clip applier 6200. Such modularity requires the controller of the clip applier to implement different operational parameters for each type of attached clip, attached clip cartridge, and/or attached end effector.

The surgical clip applier 7200 further comprises an electric motor 1160 and a driver 1161 configured to control the operation of the motor 1160 including the flow of electrical energy from a power source. The controller varies and/or modifies parameters of the electric motor 1160 through a motor control program. The motor control program is configured to determine the appropriate operational parameters based on the information received by the RFID scanner. The motor control program can compare the information received from the RFID tag to a look-up table and/or database stored within a memory, such as the memory 1212. Such a look-up table and/or database can comprise recommended operational parameters for the motor control program to implement based on the detected attached components. Operational parameters that can be adjusted based on the identification of the identified replaceable components comprise the overall motor rate, the loading force applied to a clip by the jaws of the end effector during a crimping stroke, the duration of the crimping stroke, the rate of crimping, and/or the duration the jaws of the end effector are held in a closed configuration upon completion of the crimping stroke, for example. Such operational parameters should be changed based on the attached clip to ensure proper clip closing without severing patient tissue, for example.

In various instances, the motor control program is configured to set a maximum load threshold based on the information received from the RFID tag positioned on the attached clip and/or clip cartridge. In such instances, the motor control program prevents the clip applier 7200 from performing a crimping stroke by blocking the power source's ability to supply power to the electric motor 1160 when the maximum load threshold is exceeded. In various instances, the motor control program is configured to prevent the clip applier 7200 from performing functions 1163 when other thresholds are exceeded, such as handling loads and/or elongate shaft twist loads, among others. The motor control program can implement prevent the power source from providing power to the electric motor 1160 after the crimping stroke is completed but before the jaws of the end effector are opened. Such a pause in suppling power to the motor 1160 allows the jaws to hold the crimped clip in place for a predetermined amount of time. In various instances, the clip applier 7200 comprises a locking member that holds the jaw in the closed configuration when power is no longer being supplied to the motor 1160. Such a locking member prevents the jaws from returning to the open configuration when power is no longer being supplied to the motor 1160. In various instances, the motor control program is configured to cause the power source to supply a minimum amount of power to the motor 1160 after the crimping stroke is completed, wherein the minimum amount of power is sufficient to keep the jaws in the closed configuration.

The ability for the end effector 7230 to be interchangeably attached to the elongate shaft of the clip applier 7200 requires the instrument controller to vary and/or otherwise adjust the length an advancing member must be translated to separate an individual clip from the clips stored within a clip cartridge to a crimping position, for example. The controller is configured to account for the differences in distance between the first jaw and the second jaw of the modular end effector 7330 to appropriately crimp the clips. The operational parameters should also be modified based on the attached clip to compensate for the spring back and/or other responses of the clip based on the material composition of the clip and the patient tissue, for example. The ability for the controller of the clip applier 7200 to determine the identification of the clip material and/or size, the clip cartridge side and configuration, and/or the end effector configuration and/or capabilities allows the control system to appropriately adapt by setting maximum threshold limits and/or the rates and/or speeds of performing a crimping stroke, among other things.

Figure 11:
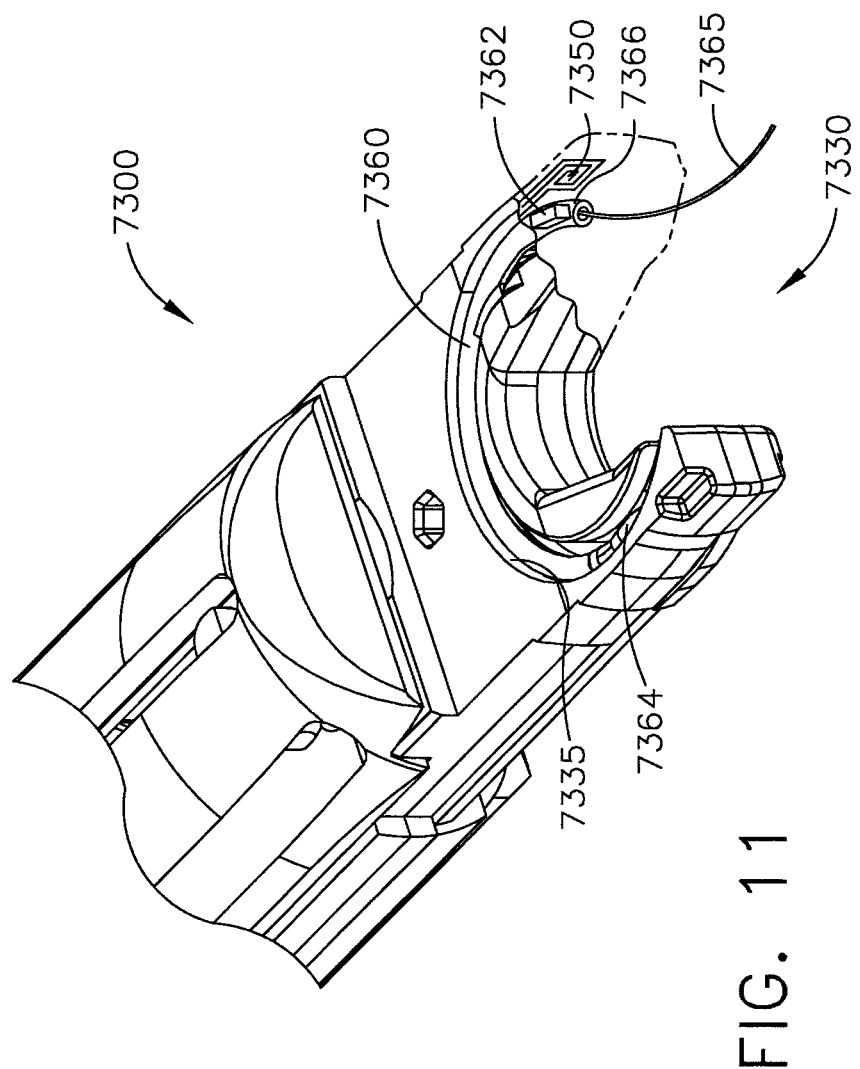
FIG. 11 is a partial perspective view of a surgical suturing device comprising an RFID system.

FIG. 11 illustrates a portion of a surgical suturing device 7300. As discussed in greater detail herein, the surgical suturing device 7300 comprises an end effector 7330. The end effector 7330 comprises a needle track 7335 configured to guide a replaceable needle 7360. The replaceable needle 7360 comprises a first end 7364 comprising a pointed tip configured to pierce through patient tissue. The replaceable needle 7360 comprises a second end 7366, wherein the second end 7366 comprises suturing material 7365 attached thereto. The replaceable needle 7360 is guided by the needle track 7335 and actuated by a firing drive through a firing stroke.

As discussed above, the needle track 7335 of the end effector 7330 is configured to receive a replaceable needle 7360. The replaceable needle 7360 comprises an RFID tag 7362. The RFID tag 7362 comprises a chip, such as a microchip, for example, that stores information about the surgical suturing device 7300, the replaceable needle 7360, and/or the suturing material 7365 attached to the replaceable needle 7360. In various instances, the set of information stored on the RFID chip comprises data that identifies the size of the needle 7360 positioned in the needle track 7335, the material the needle 7360 is comprised of, and/or the material the suturing material 7365 is comprised of. As shown in FIG. 11, the RFID tag 7362 is molded within the replaceable needle 7362. The RFID tag 7362 is molded within the replaceable needle 7362 to allow the needle 7362 to travel through the needle track 7335 uninterrupted, for example. Furthermore, the RFID tag 7362 is molded within the replaceable needle 7362 to allow the needle 7362 to travel through the patient tissue T in a smooth path. In other words, the RFID tag 7362 does not get stuck during the firing stroke and/or require an additional force to fire the replaceable needle through the patient tissue and/or the needle track 7335 during the firing stroke. That said, the RFID tag 7362 can be embedded within and/or attached to the replaceable needle 7360 by any suitable method and/or at any suitable location.

The RFID tag 7362 on the replaceable needle 7360 provides a lockout 7179 for the surgical instrument 7300. The suturing device 7300 will not perform a function with the firing drive assembly 1163, such as the needle firing stroke, for example, if the information stored on the RFID tag 7362 is not received by a controller of the surgical instrument. As mentioned in greater detail herein, the surgical suturing device 7300 comprises an RFID scanner 7350 configured to communicate with nearby RFID tags. The RFID scanner 7350 comprises a scanner antenna configured to transmit radio signals. The radio signals activate RFID tags that are positioned within a pre-determined range of the RFID scanner 7350. The RFID scanner 7350 then receives one or more response signals that are "bounced back" from the RFID tag(s). In various instances, the one or more response signals comprise the same signal as the interrogation signal. In various instances, the one or more response signals comprise a modified signal from the interrogation signal. In various instances, the RFID scanner 7350 comprises reading and writing capabilities. The RFID scanner 7350 is then able to pass the collected information from the RFID tag to a controller for further interpretation. The controller can be positioned in the surgical instrument 7300, the remote console, or in any suitable location. The RFID scanner 7350 and/or the controller can comprise a stored set of compatibility information that corresponds to replaceable needles and/or suturing materials that are compatible with a particular surgical instrument and/or for use during a particular surgical procedure.

More specifically, the surgical system 7300 comprises an RFID scanner 7350 configured to interact with the RFID tag 7362 attached to the replaceable needle 7360. The RFID scanner 7350 can be present in various locations. In the depicted embodiment, the RFID scanner 7350 is positioned on a distal end of the of the end effector 7330. More specifically, the RFID scanner 7350 is positioned at a first end of the needle track 7335 adjacent the second end 7366 of the replaceable needle 7360 when the replaceable needle 7360 is appropriately positioned in the needle track 7335; however, the RFID scanner 7350 can be located in an alternative location within the surgical system 7300 and/or any other suitable location that would allow for communication between the RFID tag 7362 and the RFID scanner 7350. The RFID scanner 7350 and/or the RFID tag 7362 are powered such that the signal(s) they emit can only be detected within a limited radius.

If the replaceable needle 7360 does not comprise an RFID tag and/or the RFID tag 7362 comprises information that is not compatible with the surgical instrument 7300, the supplemental component verification system and/or the controller of the surgical instrument 7300 will be prevent the surgical instrument from performing a function with the firing drive assembly 1163, such as the firing stroke. If the RFID scanner 7350 receives a response to an interrogation signal that is not found within a stored set of compatible supplemental components, the controller of the surgical instrument is programmed to communicate an error to the clinician. Likewise, if the RFID scanner 7350 does not receive a response to the interrogation signal, the controller of the surgical instrument is programmed to communicate an error to the clinician. In various instances, the detection of an error by the controller can render the surgical instrument inoperable for use with that particular replaceable needle 7360. In various instances, a detected error can prevent the surgical instrument from performing a firing stroke. In various instances, the surgical instrument further comprises a manual override that can be activated to allow a clinician to override any system lockout 7179 and utilize operational functions of the surgical instrument in an emergency. As discussed above, the controller is configured to alert the clinician that an error has been detected through an indicator 1209. Such an alert can be communicated through various forms of feedback, including, for example, haptic, acoustic, and/or visual feedback. The alert can be specific or generic. For example, the alert can specifically state that the RFID tag 7362 on the replaceable needle 7360 is unable to be detected, or the alert can specifically state that the RFID tag 7362 comprises information representative of an incompatible and/or defective needle 7360 and/or suturing material 7365.

In various instances, the controller can modify various operational parameters based on the identification of the replaceable needle 7360 and/or the suturing material 7365 using the information stored on the RFID tag 7362. Such an identification can include the material the needle 7360 and/or the suturing material 7365 is comprised of, the length of the suturing material 7365, and/or the thickness of the replaceable needle 7360 and/or the suturing material 7365, among other things. After identification of a characteristic of the replaceable needle 7360, the controller is configured to permit the surgical instrument to perform the desired function with the firing drive assembly 1163 using the modified operational parameters.

Figure 12:
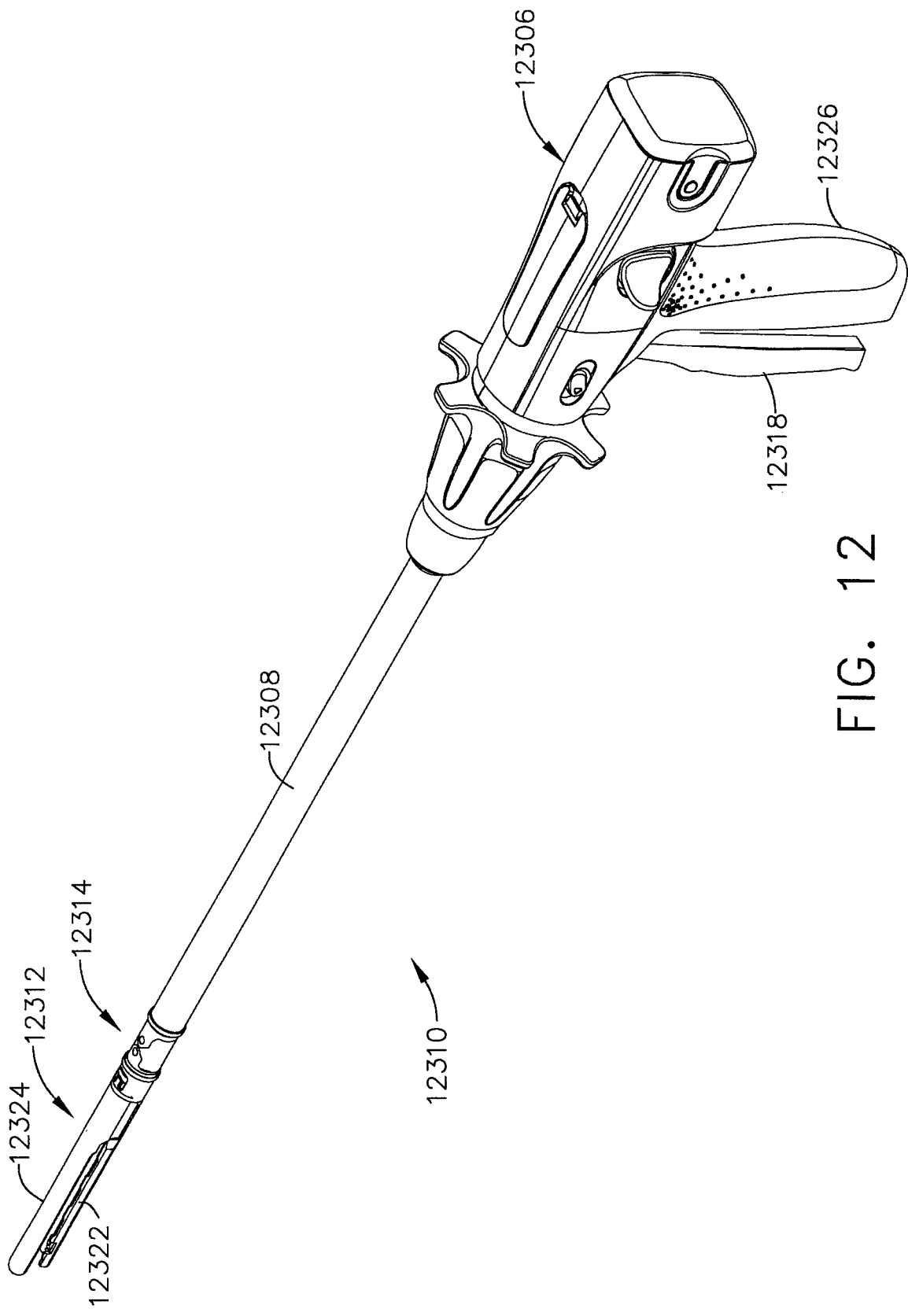
FIG. 12 is a perspective view of a surgical instrument comprising a handle, a shaft, and an articulatable end effector.
Figure 13:
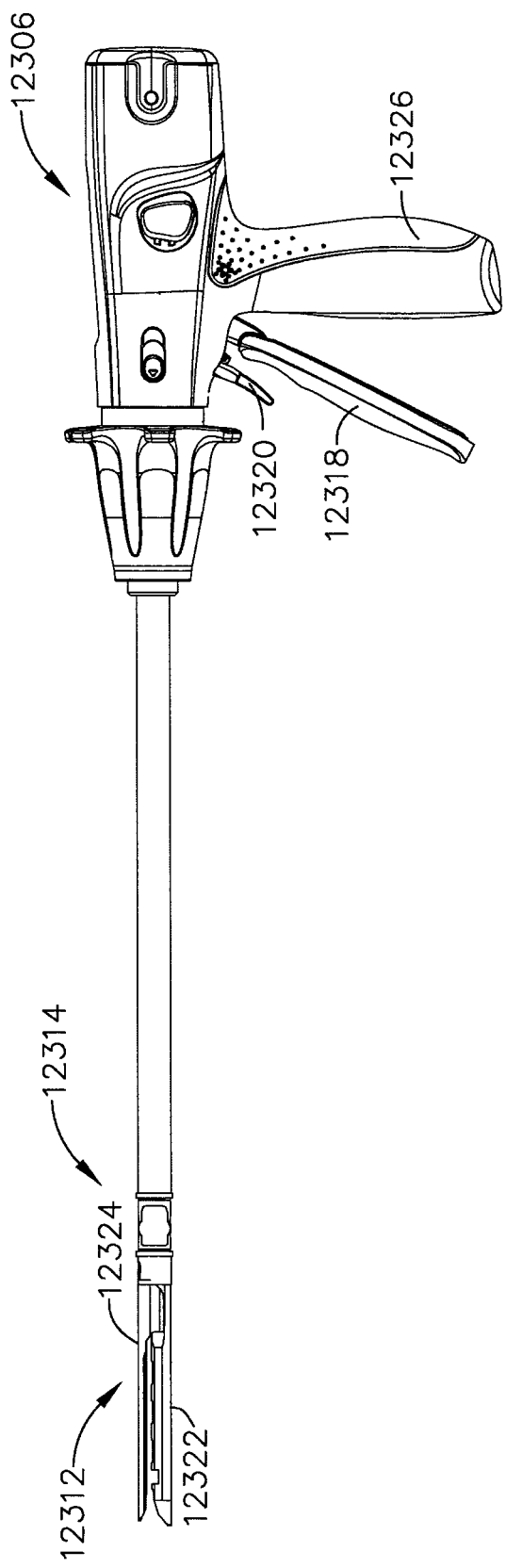
FIG. 13 is a side view of the surgical instrument of FIG. 12.

The embodiments disclosed herein are configured for use with surgical clip appliers and systems such as those disclosed in U.S. patent application Ser. No. 14/200,111, now U.S. Pat. No. 9,629,629, entitled CONTROL SYSTEMS FOR SURGICAL INSTRUMENTS, which is incorporated in its entirety herein. FIGS. 12 and 13 depict a motor-driven surgical cutting and fastening instrument 12310. This illustrated embodiment depicts an endoscopic instrument and, in general, the instrument 12310 is described herein as an endoscopic surgical cutting and fastening instrument; however, it should be noted that the invention is not so limited and that, according to other embodiments, any instrument disclosed herein may comprise a non-endoscopic surgical cutting and fastening instrument. The surgical instrument 12310 depicted in FIGS. 12 and 13 comprises a handle 12306, a shaft 12308, and an end effector 12312 connected to the shaft 12308. In various embodiments, the end effector 12312 can be articulated relative to the shaft 12308 about an articulation joint 12314. Various means for articulating the end effector 12312 and/or means for permitting the end effector 12312 to articulate relative to the shaft 12308 are disclosed in U.S. Pat. No. 7,753,245, entitled SURGICAL STAPLING INSTRUMENTS, which issued on Jul. 13, 2010, and U.S. Pat. No. 7,670,334, entitled SURGICAL INSTRUMENT HAVING AN ARTICULATING END EFFECTOR, which issued on Mar. 2, 2010, the entire disclosures of which are incorporated by reference herein. Various other means for articulating the end effector 12312 are discussed in greater detail below. Similar to the above, the end effector 12312 is configured to act as a surgical stapler for clamping, severing, and/or stapling tissue, although, in other embodiments, different types of end effectors may be used, such as end effectors for other types of surgical devices, graspers, cutters, staplers, clip appliers, access devices, drug/gene therapy devices, ultrasound, RF and/or laser devices, etc. Several RF devices may be found in U.S. Pat. No. 5,403,312, entitled ELECTROSURGICAL HEMOSTATIC DEVICE, which issued on Apr. 4, 1995, and U.S. patent application Ser. No. 12/031,573, entitled SURGICAL CUTTING AND FASTENING INSTRUMENT HAVING RF ELECTRODES, filed Feb. 14, 2008, the entire disclosures of which are incorporated by reference in their entireties.

The end effector 12312 can include, among other things, a staple channel 12322 and a pivotally translatable clamping member, such as an anvil 12324, for example. The handle 12306 of the instrument 12310 may include a closure trigger 12318 and a firing trigger 12320 for actuating the end effector 12312. It will be appreciated that instruments having end effectors directed to different surgical tasks may have different numbers or types of triggers or other suitable controls for operating the end effector 12312. The handle 12306 can include a downwardly extending pistol grip 12326 toward which the closure trigger 12318 is pivotally drawn by the clinician to cause clamping or closing of the anvil 12324 toward the staple channel 12322 of the end effector 12312 to thereby clamp tissue positioned between the anvil 12324 and channel 12322. In other embodiments, different types of clamping members in addition to or lieu of the anvil 12324 could be used. The handle 12306 can further include a lock which can be configured to releasably hold the closure trigger 12318 in its closed position. More details regarding embodiments of an exemplary closure system for closing (or clamping) the anvil 12324 of the end effector 12312 by retracting the closure trigger 12318 are provided in U.S. Pat. No. 7,000,818, entitled SURGICAL STAPLING INSTRUMENT HAVING SEPARATE DISTINCT CLOSING AND FIRING SYSTEMS, which issued on Feb. 21, 2006, U.S. Pat. No. 7,422,139, entitled MOTOR-DRIVEN SURGICAL CUTTING AND FASTENING INSTRUMENT WITH TACTILE POSITION FEEDBACK, which issued on Sep. 9, 2008, and U.S. Pat. No. 7,464,849, entitled ELECTRO-MECHANICAL SURGICAL INSTRUMENT WITH CLOSURE SYSTEM AND ANVIL ALIGNMENT COMPONENTS, which issued on Dec. 16, 2008, the entire disclosures of which are incorporated by reference herein.

Once the clinician is satisfied with the positioning of the end effector 12312, the clinician may draw back the closure trigger 12318 to its fully closed, locked position proximate to the pistol grip 12326. The firing trigger 12320 may then be actuated, or fired. In at least one such embodiment, the firing trigger 12320 can be farther outboard of the closure trigger 12318 wherein the closure of the closure trigger 12318 can move, or rotate, the firing trigger 12320 toward the pistol grip 12326 so that the firing trigger 12320 can be reached by the operator using one hand. Thereafter, the operator may pivotally draw the firing trigger 12320 toward the pistol grip 12312 to cause the stapling and severing of clamped tissue in the end effector 12312. Thereafter, the firing trigger 12320 can be returned to its unactuated, or unfired, position after the clinician relaxes or releases the force being applied to the firing trigger 12320. A release button on the handle 12306, when depressed, may release the locked closure trigger 12318. The release button may be implemented in various forms such as, for example, those disclosed in published U.S. Patent Application Publication No. 2007/0175955, entitled SURGICAL CUTTING AND FASTENING INSTRUMENT WITH CLOSURE TRIGGER LOCKING MECHANISM, which was filed on Jan. 31, 2006, the entire disclosure of which is incorporated herein by reference in its entirety.

Further to the above, the end effector 12312 may include a cutting instrument, such as knife, for example, for cutting tissue clamped in the end effector 12312 when the firing trigger 12320 is retracted by a user. Also further to the above, the end effector 12312 may also comprise means for fastening the tissue severed by the cutting instrument, such as staples, RF electrodes, and/or adhesives, for example. A longitudinally movable drive shaft located within the shaft 12308 of the instrument 12310 may drive/actuate the cutting instrument and the fastening means in the end effector 12312. An electric motor, located in the handle 12306 of the instrument 12310 may be used to drive the drive shaft, as described further herein. In various embodiments, the motor may be a DC brushed driving motor having a maximum rotation of, approximately, 25,000 RPM, for example. In other embodiments, the motor may include a brushless motor, a cordless motor, a synchronous motor, a stepper motor, or any other suitable electric motor. A battery (or "power source" or "power pack"), such as a Li ion battery, for example, may be provided in the pistol grip portion 12326 of the handle 12306 adjacent to the motor wherein the battery can supply electric power to the motor via a motor control circuit. According to various embodiments, a number of battery cells connected in series may be used as the power source to power the motor. In addition, the power source may be replaceable and/or rechargeable.

Figure 14:
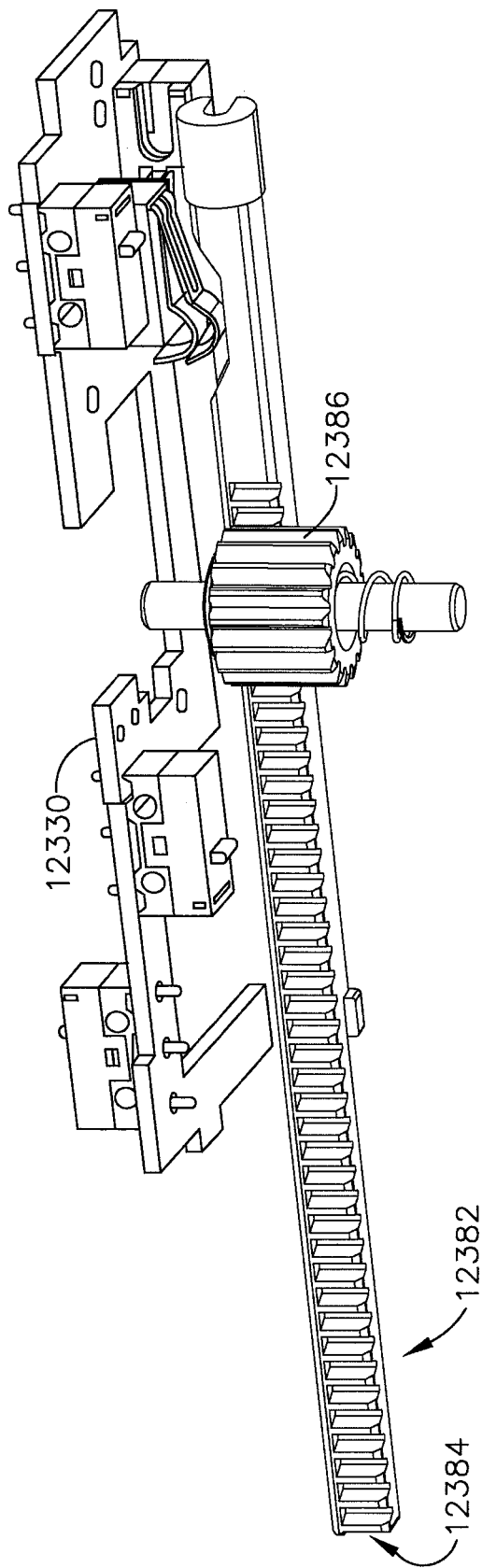
FIG. 14 is a perspective view of a firing member and a pinion gear positioned within the handle of FIG. 12.
Figure 15:
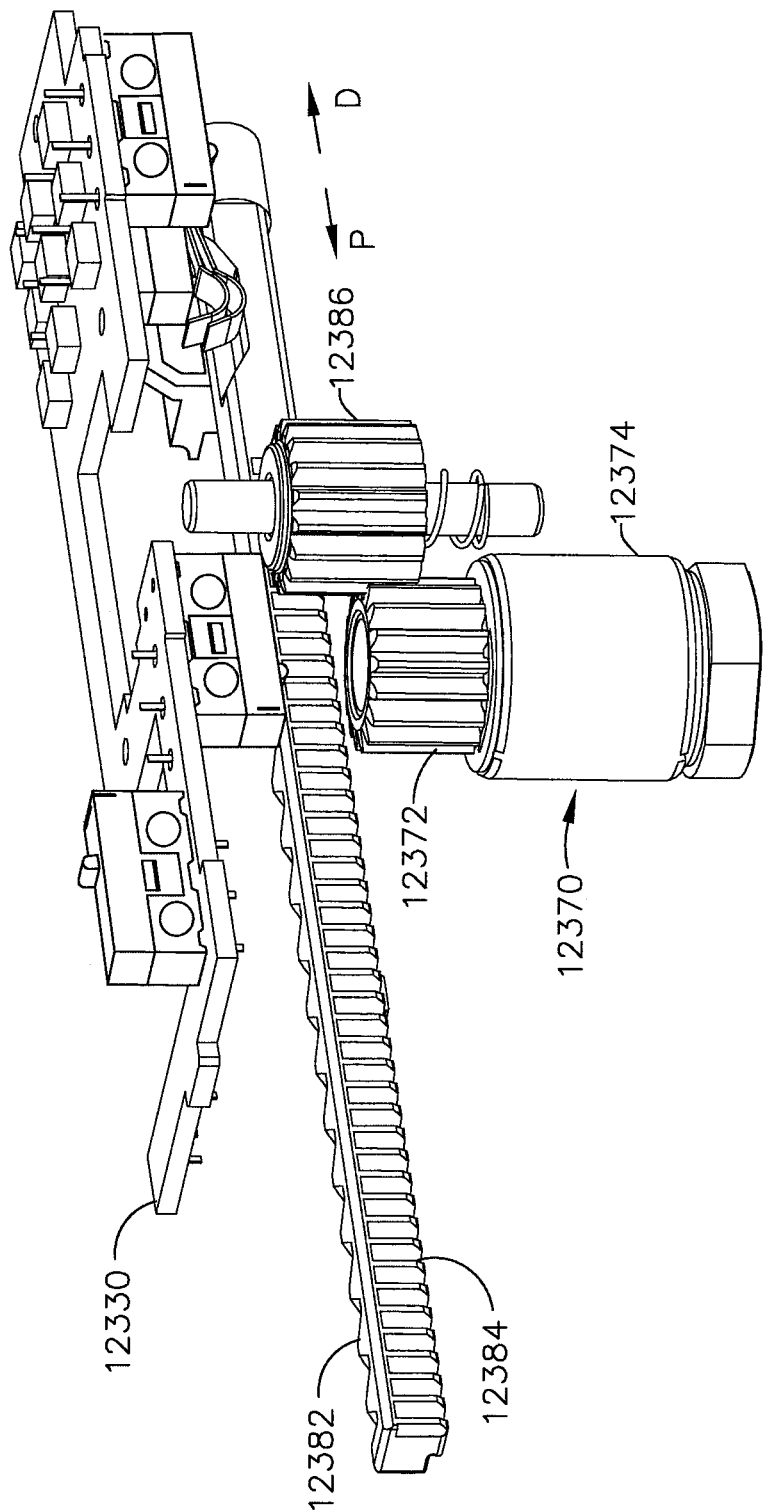
FIG. 15 is a perspective view of the firing member and the pinion gear of FIG. 14 and a gear reducer assembly operably engaged with the pinion gear.
Figure 16:
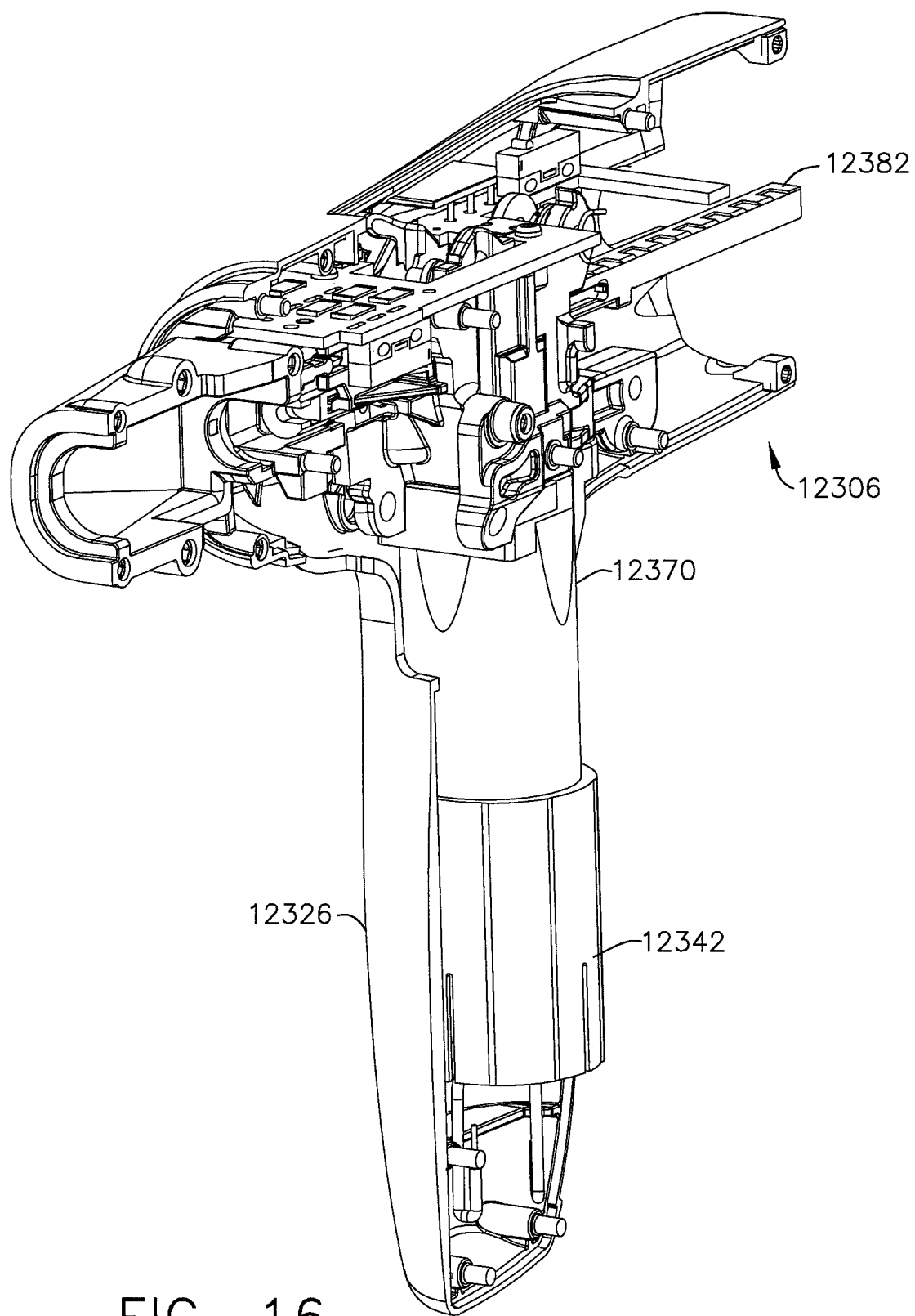
FIG. 16 is a perspective view of the handle of FIG. 12 with portions thereof removed to illustrate the firing member and the pinion gear of FIG. 14, the gear reducer assembly of FIG. 15, and an electric motor configured to drive the firing member distally and/or proximally depending on the direction in which the electric motor is turned.

As outlined above, the electric motor in the handle 12306 of the instrument 12310 can be operably engaged with the longitudinally-movable drive member positioned within the shaft 12308. Referring now to FIGS. 14-16, an electric motor 12342 can be mounted to and positioned within the pistol grip portion 12326 of the handle 12306. The electric motor 12342 can include a rotatable shaft operably coupled with a gear reducer assembly 12370 wherein the gear reducer assembly 12370 can include, among other things, a housing 12374 and an output pinion gear 12372. In certain embodiments, the output pinion gear 12372 can be directly operably engaged with a longitudinally-movable drive member 12382 or, alternatively, operably engaged with the drive member 12382 via one or more intermediate gears 12386. The intermediate gear 12386, in at least one such embodiment, can be meshingly engaged with a set, or rack, of drive teeth 12384 defined in the drive member 12382. In use, the electric motor 12342 can be drive the drive member distally, indicated by an arrow D (FIG. 9), and/or proximally, indicated by an arrow D (FIG. 10), depending on the direction in which the electric motor 12342 rotates the intermediate gear 12386. In use, a voltage polarity provided by the battery can operate the electric motor 12342 in a clockwise direction wherein the voltage polarity applied to the electric motor by the battery can be reversed in order to operate the electric motor 12342 in a counter-clockwise direction. The handle 12306 can include a switch which can be configured to reverse the polarity applied to the electric motor 12342 by the battery. The handle 12306 can also include a sensor 12330 configured to detect the position of the drive member 12382 and/or the direction in which the drive member 12382 is being moved.

Figure 17:
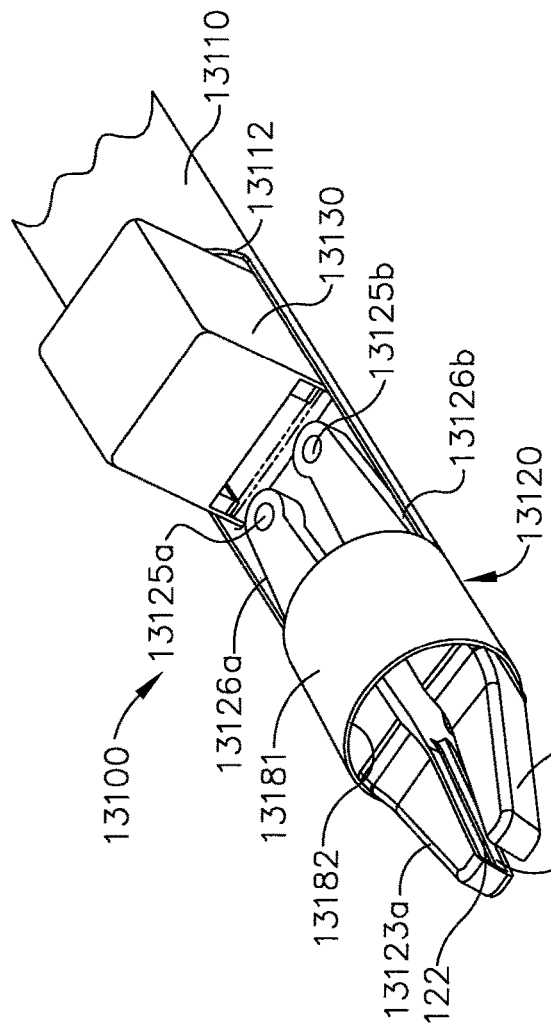
FIG. 17 is a partial perspective view of a clip applier.
Figure 25:
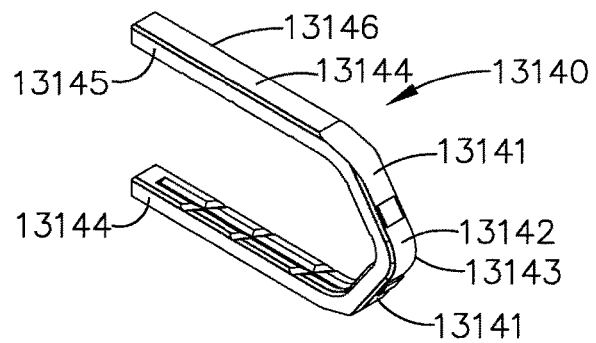
FIG. 25 is a perspective view of a clip illustrated in FIG. 18.

The embodiments disclosed herein are configured for use with surgical clip appliers and systems such as those disclosed in U.S. patent application Ser. No. 16/112,237, filed on Aug. 24, 2018, now U.S. Patent Application Publication No. 2019/0125347, entitled SURGICAL CLIP APPLIER CONFIGURED TO STORE CLIPS IN A STORED STATE, which is incorporated in its entirety herein. Referring to FIG. 17, a surgical instrument, such as a clip applier 13100, for example, can be configured to apply one or more clips to tissue located within a surgical site in the patient. Generally, referring now to FIG. 25, the clip applier 13100 can be structured and arranged to position a clip 13140 relative to the tissue in order to compress the tissue within the clip 13140. The clip applier 13100 can be configured to deform the clip 13140 as illustrated in FIGS. 19 and 20, for example, and as described in greater detail further below. Each clip 13140 can comprise a base 13142 and opposing legs 13144 extending from the base 13142. The base 13142 and the legs 13144 can comprise any suitable shape and can define a substantially U-shaped configuration and/or a substantially V-shaped configuration, for example. The base 13142 can comprise angled portions 13141 which are connected together by a joint 13143. In use, the legs 13144 of the clip 13140 can be positioned on opposite sides of the tissue wherein the legs 13144 can be pushed toward one another to compress the tissue positioned between the legs 13144. The joint 13143 can be configured to permit the angled portions 13141 of the base 13142, and the legs 13144 extending therefrom, to deform inwardly. In various circumstances, the clip 13140 can be configured to yield, or deform plastically, when the clip 13140 is sufficiently compressed, although some amount of elastic deformation, or spring-back, may occur within the deformed clip 13140.

Figure 18:
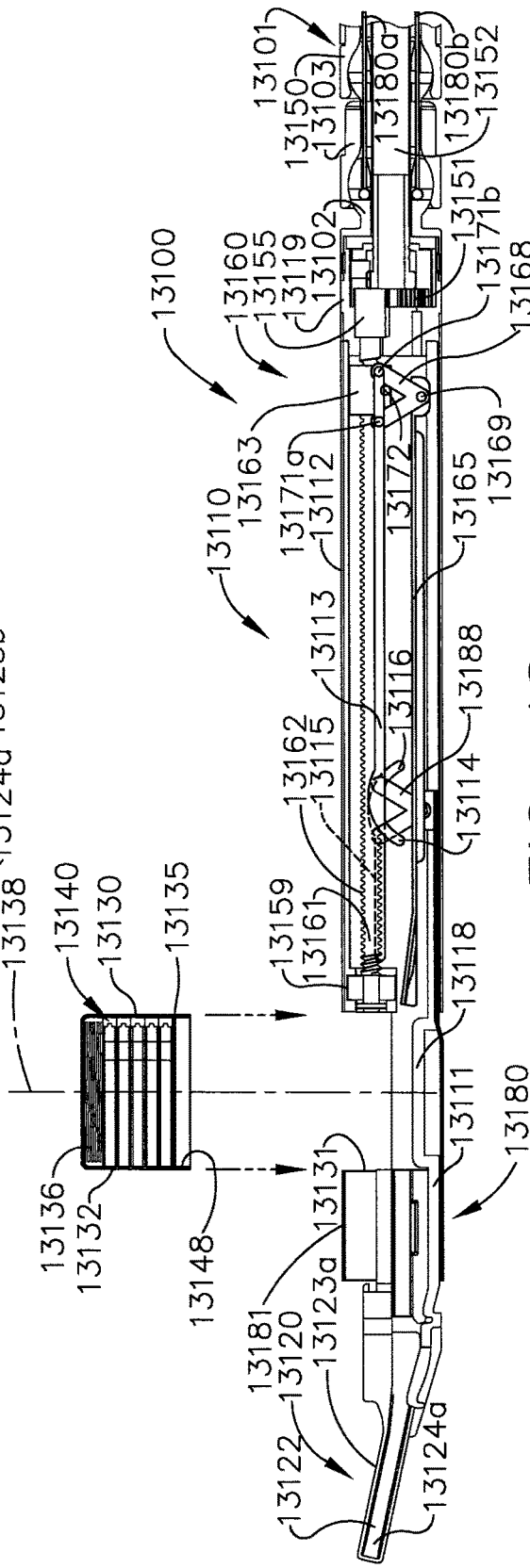
FIG. 18 is a cross-sectional view of an end effector of the clip applier of FIG. 17 comprising a removable clip cartridge, a reciprocating firing drive for sequentially advancing the clips, a receiver for receiving the clips, and a crimping drive for deforming the clips.
Figure 26:
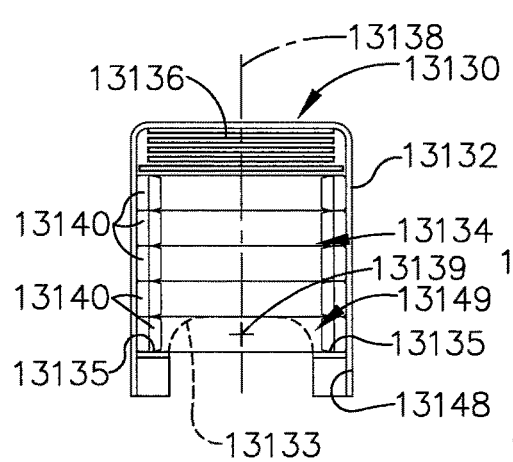
FIG. 26 is a front view of a cartridge illustrated in FIG. 18 comprising a plurality of clips with portions of the cartridge removed to illustrate the clips stored in the cartridge.
Figure 27:
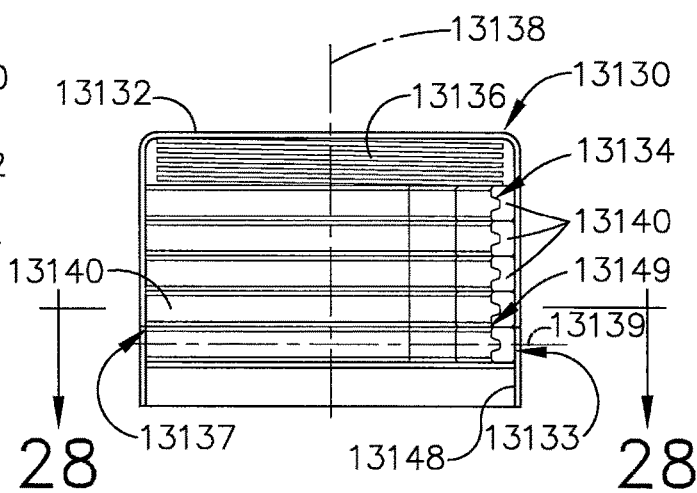
FIG. 27 is a side view of the cartridge of FIG. 26 illustrated with portions removed to illustrate the clips stored in the cartridge.
Figure 28:
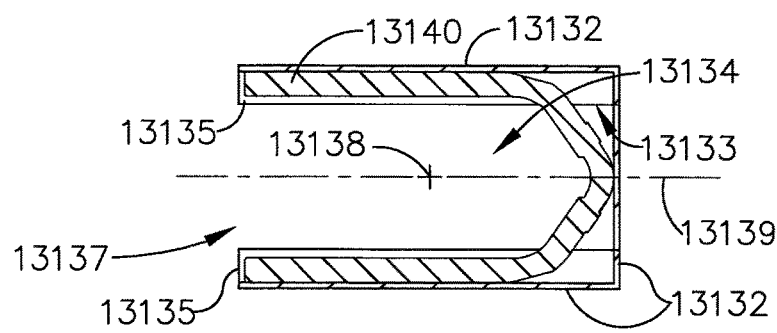
FIG. 28 is a cross-sectional plan view of the cartridge of FIG. 26 taken along line 28-28 in FIG. 27.
Figure 29:
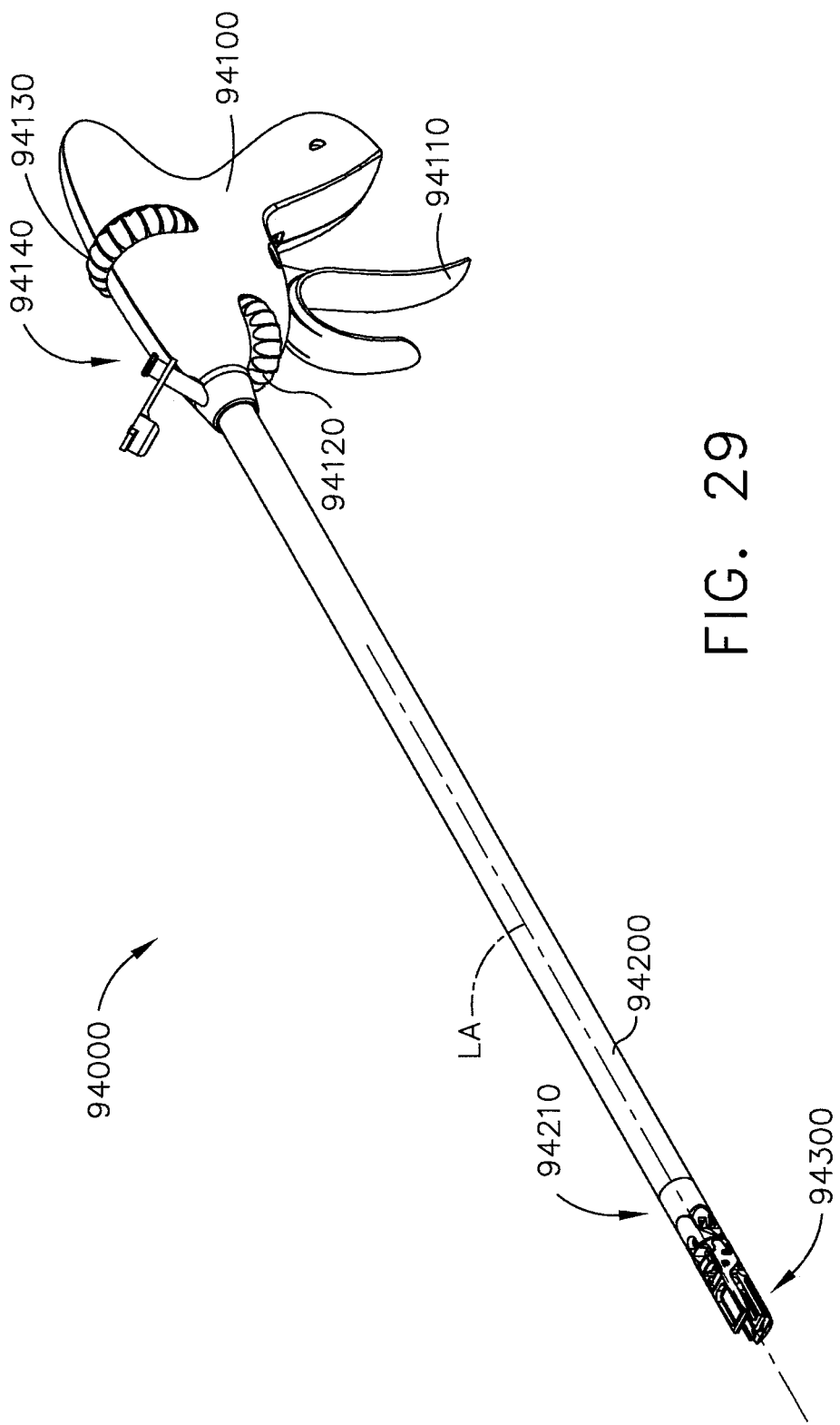
FIG. 29 is a perspective view of a surgical suturing instrument comprising a handle, a shaft, and an end effector.
Figure 30:
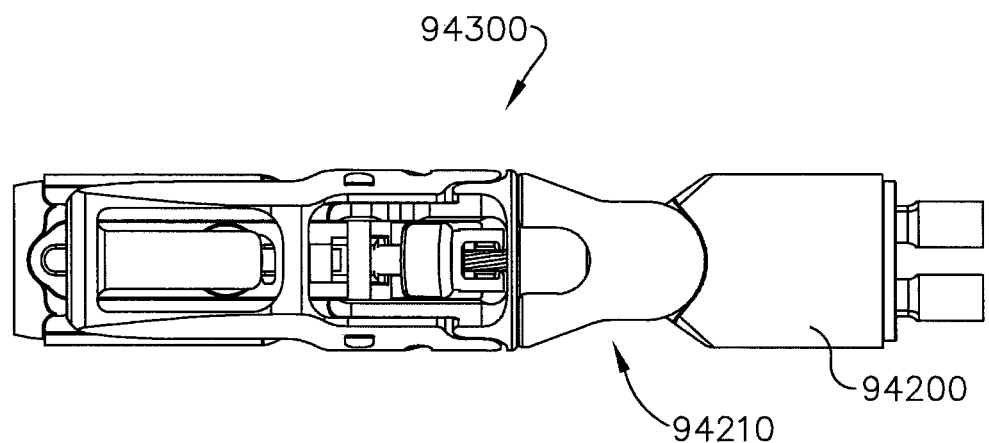
FIG. 30 is a partial plan view of the surgical suturing instrument of FIG. 29.
Figure 31:
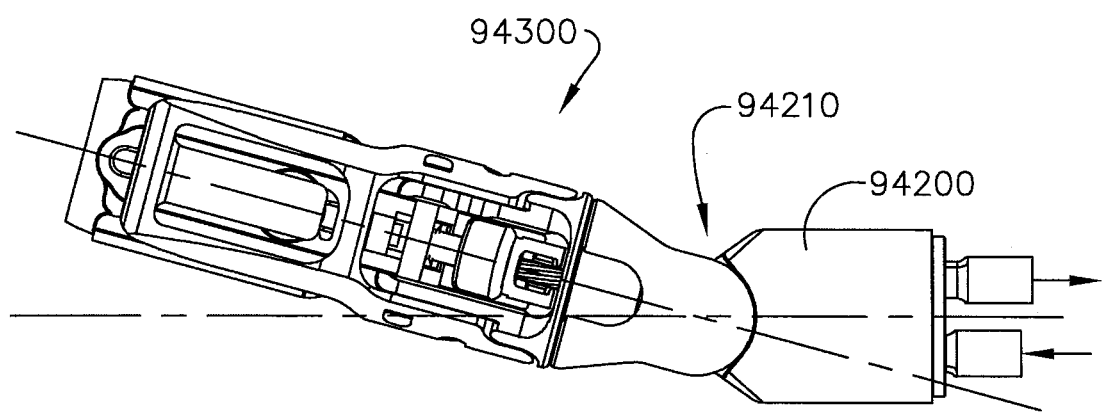
FIG. 31 is a partial plan view of the surgical suturing instrument of FIG. 29, wherein the end effector is in an articulated state.
Figure 32:
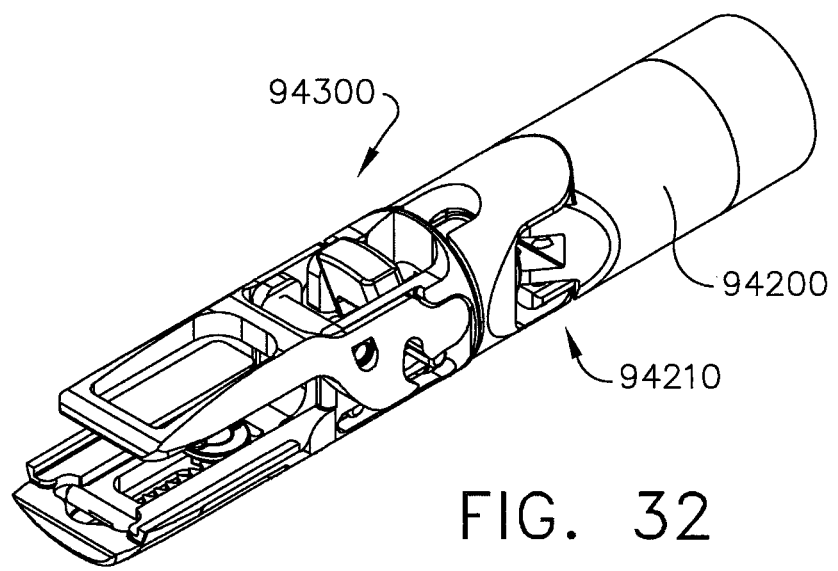
FIG. 32 is a partial perspective view of the surgical suturing instrument of FIG. 29.
Figure 33:
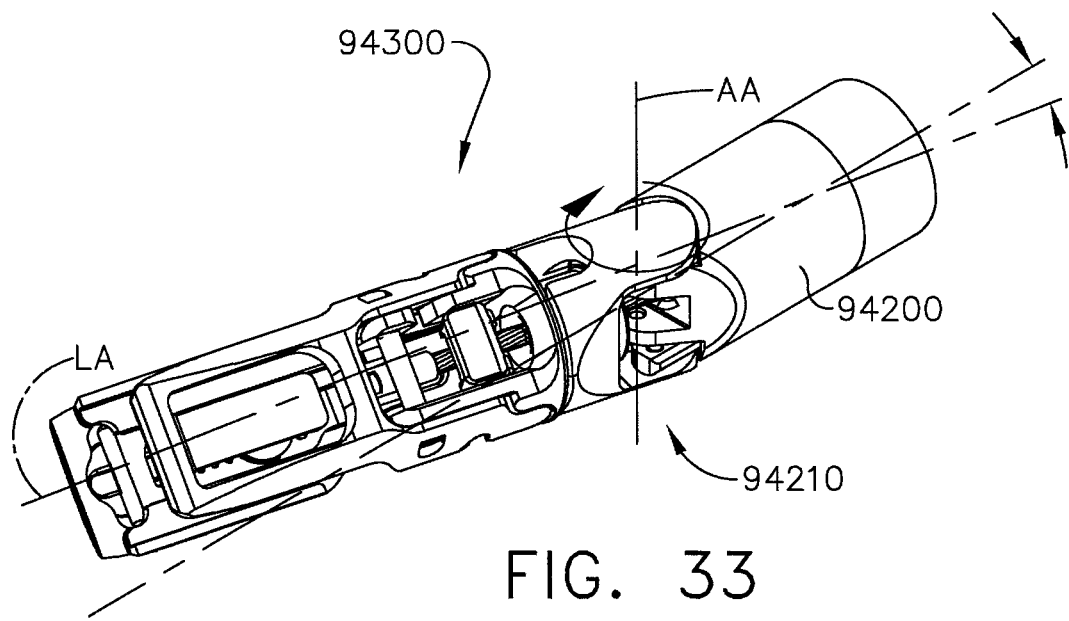
FIG. 33 is a partial perspective view of the surgical suturing instrument of FIG. 29, wherein the end effector is in an articulated and rotated state.

Referring now to FIGS. 17 and 18, the clip applier 13100 can include a shaft 13110, an end effector 13120, and a replaceable clip cartridge, or magazine, 13130. Referring to FIGS. 26-28, the clip cartridge 13130 can comprise a housing 13132 and a plurality of clips 13140 positioned within the housing 13132. The housing 13132 can define a storage chamber 13134 in which the clips 13140 can be stacked. The storage chamber 13134 can comprise sidewalls which extend around, or at least substantially around, the perimeter of the clips 13140. Referring again to FIG. 25, each clip 13140 can comprise opposing faces, such as a top face 13145 and a bottom face 13146 on opposite sides of the clip 13140 wherein, when the clips 13140 are stacked in the housing 13132, the top face 13145 of a clip 13140 can be positioned against the bottom face 13146 of an adjacent clip 13140 and wherein the bottom face 13146 of the clip 13140 can be positioned against the top face 13145 of another adjacent clip 13140. In various circumstances, the bottom faces 13146 of the clips 13140 can face downwardly toward one or more support shelves, or platforms, 13135 defined in the housing 13132 while the top faces 13145 of the clips 13140 can face upwardly away from the support shelves 13135. The top faces 13145 and the bottom faces 13146 of the clips 13140 may be identical, or at least substantially identical, in some cases, while, in other cases, the top faces 13145 and the bottom faces 13146 may be different. The stack of clips 13140 depicted in FIGS. 26-28 comprises five clips 13140, for example; however, other embodiments are envisioned in which the stack of clips 13140 can include more than five clips 13140 or less than five clips 13140. In any event, the clip cartridge 13130 can further comprise at least one biasing member, such as biasing member 13136, for example, positioned intermediate the housing 13132 and the top clip 13140 in the stack of clips 13140. As described in greater detail below, the biasing member 13136 can be configured to bias the bottom clip 13140 in the stack of clips 13140 or, more particularly, the bottom face 13146 of the bottom clip 13140, against the support shelves 13135 defined in the housing 13132. The biasing member 13136 can comprise a spring, and/or any suitable compressed elastic element, for example, which can be configured to apply a biasing force to the clips 13140, or at least apply a biasing force to the top clip 13140 which is transmitted downwardly through the stack of clips 13140.

When a clip 13140 is positioned against the support shelves 13135 as described above, the clip 13140 can be supported in a firing position in which the clip 13140 can be advanced and ejected from the cartridge 13130. In various circumstances, the support shelves 13135 can define at least a portion of a firing chamber 13149 in which the clips 13140 can be sequentially positioned in the firing position. In some cases, the firing chamber 13149 can be entirely defined within the cartridge 13130 or, in other cases, the firing chamber 13149 can be defined within and/or between the shaft 13110 and the cartridge 13130. In any event, as described in greater detail further below, the clip applier 13100 can comprise a firing drive which can advance a firing member into the cartridge 13130 and push the clip 13140 from its firing position positioned against the support shelves 13135 to a fired position in which it is received within the end effector 13120 of the clip applier 13100. Referring primarily to FIGS. 26-28, the housing 13132 of the cartridge 13130 can comprise a proximal opening, or window, 13133 which can be aligned, or at least substantially aligned, with the support shelves 13135 such that the firing member can enter into the cartridge 13130 through the proximal opening 13133 and advance a clip 13140 distally out of the cartridge 13130. In at least one such embodiment, the housing 13132 can further comprise a distal, or discharge, opening, or window, 13137 which is also aligned with the support shelves 13135 such that the clip 13140 can be advanced, or fired, distally along a firing axis 13139 extending through the proximal opening 13133, the firing chamber 13149, and the distal opening 13137, for example.

In order to advance a clip 13140 out of the cartridge 13130, further to the above, the firing member of the firing drive can be advanced into to the cartridge housing 13132 and, in various circumstances, into the firing chamber 13149. As disclosed in greater detail further below, the firing member can pass entirely through the cartridge 13130 in order to advance the clip 13140 into its fired position within the end effector 13120. After the clip 13140 positioned in the firing chamber 13149 has been advanced distally by the firing member, as outlined above, the firing member can be retracted sufficiently such that the biasing member 13136 can position another clip 13140 against the support shelves 13135. In various circumstances, the biasing member 13136 can bias a clip 13140 against the firing member while the firing member is positioned within the housing 13132. Such a clip 13140 can be referred to as a queued clip. After the firing member has been sufficiently retracted and slid out from underneath the queued clip 13140, the biasing member 13136 can then bias the clip 13140 against the support shelves 13135 where it is staged for the next stroke of the reciprocating firing member. Referring primarily to FIGS. 18 and 26-28, the cartridge 13130 can be configured to supply the clips 13140 to the firing chamber 13149 along a predetermined path, such as supply axis 13138, for example. The supply axis 13138 can be transverse to the firing axis 13139 such that the clips 13140 are fed into the firing chamber 13149 in a direction which is different than the direction in which the firing member passes through the firing chamber 13149. In at least one such embodiment, the supply axis 13138 can be perpendicular, or at least substantially perpendicular, to the firing axis 13139, for example.

Referring again to FIG. 18, the shaft 13110 can comprise a cartridge, or magazine, aperture 13131 which can be sized and configured to receive a clip cartridge 13130, for example, therein. The cartridge aperture 13131 can be sized and configured such that the housing 13132 of the cartridge 13130 is closely received within the cartridge aperture 13131. The sidewalls which define the cartridge aperture 13131 can limit, or at least substantially limit, the lateral movement of the cartridge 13130 relative to the shaft 13110. The shaft 13110 and/or the cartridge 13130 can further comprise one or more locks which can be configured to releasably hold the cartridge 13130 in the cartridge aperture 13131. As illustrated in FIG. 18, the cartridge 13130 can be loaded into the cartridge aperture 13131 along an axis which is, in at least one embodiment, parallel to or collinear with the supply axis 13138. As also illustrated in FIG. 18, the shaft 13110 can further comprise a pad or seat 13118 extending from the sidewall 13111 of the shaft 13110 wherein the pad 13118 can be configured to be received within and/or engaged with the housing 13132 of the cartridge 13130. The pad 13118 can be sized and configured to be closely received within a recess 13148 defined in the cartridge housing such that the pad 13118 can limit, or at least substantially limit, the lateral movement of the cartridge 13130 relative to the shaft 13110. The pad 13118 can be sized and configured to align the cartridge 13130 within the shaft 13110 and/or support the cartridge housing 13132.

Figure 21:
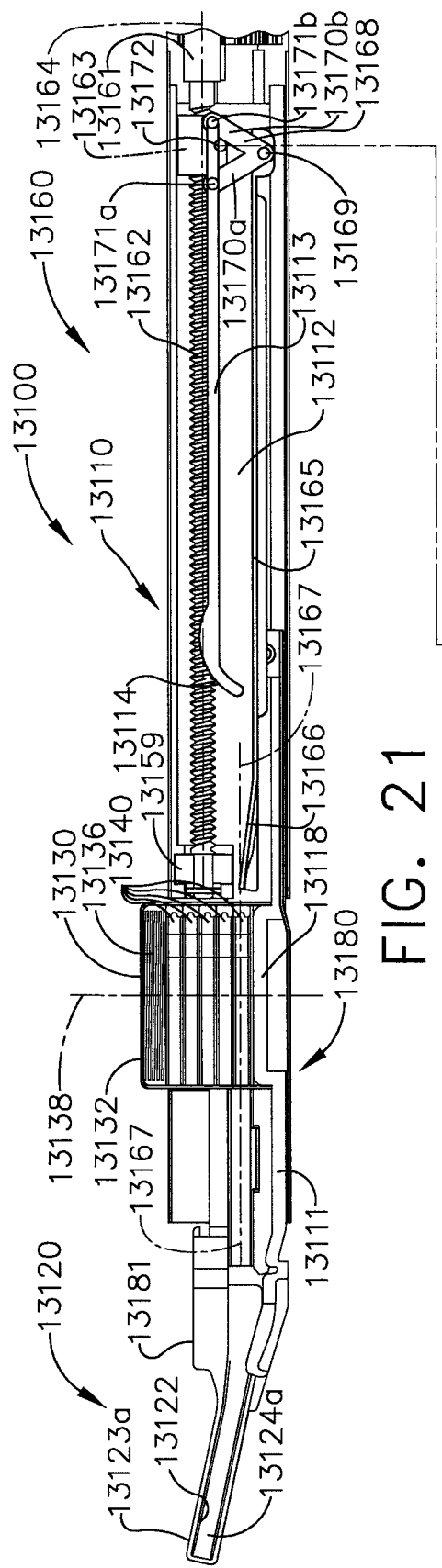
FIG. 21 is a cross-sectional view of the end effector of FIG. 18 in an unfired condition.
Figure 22:
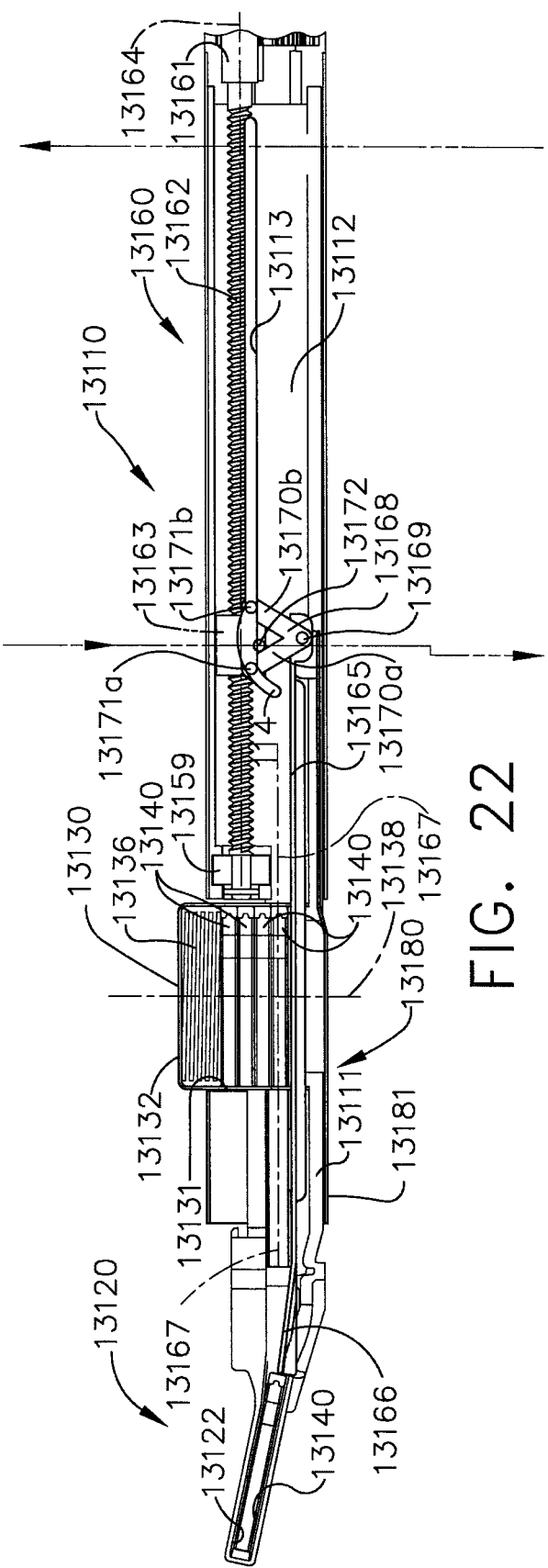
FIG. 22 is a cross-sectional view of the end effector of FIG. 18 illustrating the firing drive in a partially fired condition in which a firing member of the firing drive has advanced a clip into the receiver.

Once the clip cartridge 13130 has been positioned and seated within the shaft aperture 13131, referring now to FIGS. 21 and 22, a firing drive 13160 of the clip applier 13100 can be actuated to advance the clips 13140 from the clip cartridge 13130 as described above. The firing drive 13160 can comprise a rotary drive input such as a drive screw 13161, for example, and a displaceable firing nut 13163 operably engaged with the drive screw 13161. The drive screw 13161 can comprise at least one drive thread 13162 which can be threadably engaged with a threaded aperture extending through the firing nut 13163. In various embodiments, the clip applier 13100 can further include an electric motor, for example, operably coupled with the drive screw 13161. In various instances, the drive screw 13161 can be operably coupled with the motor of a surgical instrument system comprising a hand-held instrument or a robotic arm, for example. In any event, the movement of the firing nut 13163 within the shaft 13110 can be constrained such that the firing nut 13163 moves along a longitudinal axis 13164 when the drive screw 13161 is rotated about the longitudinal axis 13164 by the motor. For instance, when the drive screw 13161 is rotated in a first direction by the motor, the drive screw 13161 can advance the firing nut 13163 distally toward the end effector 13120, as illustrated in FIG. 22. When the drive screw 13161 is rotated in a direction opposite the first direction by the motor, the drive screw 13161 can retract the firing nut 13163 proximally away from the end effector 13120. The shaft 13110 can comprise one or more bearings which can be configured to rotatably support the drive screw 13161. For instance, a bearing 13159 can be configured to rotatably support the distal end of the drive screw 13161, for example, as illustrated in FIGS. 21 and 22.

The firing drive 13160 can further comprise a firing member 13165 extending from the firing nut 13163 which can be advanced distally and retracted proximally with the firing nut 13163, as described in greater detail further below. Upon comparing FIGS. 21 and 22, the reader will note that the firing nut 13163 and the firing member 13165 have been advanced from a proximal, unfired position, illustrated in FIG. 21, to a distal, fired position, illustrated in FIG. 22, in which the firing member 13165 has advanced a clip 13140 from the clip cartridge 13130 into the end effector 13120. Referring primarily to FIG. 21, the clip cartridge 13130 is illustrated as comprising a plurality of clips 13140 stored therein wherein one of the clips 13140 is positioned in a firing position, as described above. As illustrated in FIGS. 21 and 22, the firing member 13165 can include a distal portion 13166 which can be advanced into the staple cartridge 13130 along a firing axis 13167 and engage the clip 13140 positioned in the firing position when the firing member 13165 and the firing nut 13163 are advanced distally. In some cases, the firing member 13165 can comprise a linear member while, in other cases, the distal end 13166 of the firing member 13165 can extend upwardly from the firing member 13165, for example. Further to the above, the firing member 13165 can advance the clip 13140 distally out of the clip cartridge 13130 along the firing axis 13167 and into a receiving cavity 13122 defined in the end effector 13120.

In various cases, the firing member 13165 can be attached to and extend distally from the firing nut 13163 while, in other cases, the firing member 13165 and the firing nut 13163 can be operably connected to one another by a firing actuator 13168. The firing actuator 13168 can be pivotably mounted to the firing member 13165 at a pivot 13169 and can include a distal arm 13170a and a proximal arm 13170b which can be engaged with a longitudinal slot 13113 defined in the housing 13112 of the shaft 13110. In at least one such embodiment, each of the arms 13170a, 13170b can include a projection, such as projections 13171a and 13171b, respectively, extending therefrom which can be configured to slide within the longitudinal slot 13113. Further to the above, the firing nut 13163 can further include a firing pin 13172 extending therefrom which can be configured to engage the distal arm 13170a in order to advance the actuator 13168 and the firing member 13165 distally, as described above. In use, referring again to the progression illustrated in FIGS. 21 and 22, the firing nut 13163 can be advanced distally by the drive screw 13161 wherein the firing pin 13172, which is positioned intermediate the distal arm 13170a and the proximal arm 13170b, can contact the distal arm 13170a and drive the actuator 13168 and the firing member 13165 distally. As the actuator 13168 is advanced distally, the actuator 13168 may be prevented from rotating about the pivot pin 13169 as one or both of the projections 13171a and 13171b sliding in the shaft slot 13113 can be prevented from being moved laterally relative to the longitudinal shaft slot 13113 until the actuator 13168 reaches the position illustrated in FIG. 22.

Once a clip 13140 has been positioned within the receiving cavity 13122, further to the above, the clip 13140 can be deformed by a crimping drive 13180, for example. Referring now to FIGS. 19 and 20, the end effector 13120 of the clip applier 13100 can further comprise a first jaw 13123a and a second jaw 13123b wherein the first jaw 13123a and the second jaw 13123b can at least partially define the receiving chamber 13122. As illustrated in FIGS. 19 and 20, the first jaw 13123a can comprise a first channel 13124a and the second jaw 13123b can comprise a second channel 13124b which can each be configured to receive and support at least a portion of a clip 13140 therein. The first jaw 13123a can be pivotably coupled to a frame 13111 of the shaft 13110 by a pin 13125a and the second jaw 13123b can be pivotably coupled to the frame 13111 by a pin 13125b. In use, the crimping drive 13180 can be configured to rotate the first jaw 13123a toward the second jaw 13123b and/or rotate the second jaw 13123b toward the first jaw 13123a in order to compress the clip 13140 positioned therebetween. In at least one such embodiment, the crimping drive 13180 can comprise a cam actuator 13181 which can be configured to engage a first cam surface 13126a defined on the first jaw 13123a and a second cam surface 13126b on the second jaw 13123b in order to pivot the first jaw 13123a and the second jaw 13123b toward one another. The cam actuator 13181 can comprise a collar which at least partially surrounds the first jaw 13123a and the second jaw 13123b. In at least one such embodiment, the collar can comprise an inner cam surface 13182 which can be contoured to contact the cam surfaces 13126a, 13126b of the jaws 13123a, 13123b and drive them inwardly toward one another. In various circumstances, the clip 13140 positioned within the receiving chamber 13122 defined in the end effector 13120 can be positioned relative to tissue before the crimping drive 13180 is actuated. In some circumstances, the crimping drive 13180 can be at least partially actuated prior to positioning the clip 13140 relative to the tissue in order to at least partially compress the clip 13140. In certain instances, the clip 13140 and the receiving chamber 13122 can be sized and configured such that the clip 13140 can be biased or flexed inwardly when the end effector 13120 is in its unactuated state, as illustrated in FIG. 19. In various instances, the crimping first jaw 13123a and the second jaw 13123b can be actuated to elastically crimp and/or permanently crimp the clip 13140 positioned therebetween.

Further to the above, the firing nut 13163 can be configured to actuate the crimping drive 13180. More particularly, referring now to FIG. 23, the crimping drive 13180 can comprise a crimping actuator 13188 operably coupled with the cam actuator 13181 wherein the crimping actuator 13188 can be selectively engaged by the firing nut 13163 as the firing nut 13163 is advanced distally as described above. In at least one such embodiment, the firing nut 13163 can further comprise a second firing pin, such as firing pin 13184, for example, extending therefrom which can be configured to engage the crimping actuator 13188 as the firing nut 13163 is advancing the firing actuator 13168. Referring again to FIG. 23, the crimping actuator 13188 is positioned in an unactuated position and, when the firing nut 13163 is advanced sufficiently to engage a distal arm 13190a of the crimping actuator 13188, the firing nut 13163 can rotate the crimping actuator 13188 upwardly into an actuated position as illustrated in FIG. 24. As also illustrated in FIG. 24, the distal arm 13190a and a proximal arm 13190b can each comprise a projection, such as projections 13191a and 13191b, respectively, extending therefrom which can be positioned within a second longitudinal slot defined in shaft 13110, such as slot 13115, for example. As the crimping actuator 13188 is rotated upwardly from its unactuated position about a pivot 13189, the projections 13191a and 13191b can move from the proximal curved end 13116 of the longitudinal slot 13115 into a portion of the longitudinal slot 13115 which is substantially linear. Similar to the above, the sidewalls of the longitudinal slot 13115 can be configured to confine the movement of the crimping actuator 13188 along a longitudinal path and can be configured to limit or prevent the rotation of the crimping actuator 13188 once the crimping actuator 13188 has been rotated upwardly into an at least partially actuated position, as discussed above. As the reader will understand, the firing pin 13172 of the firing drive 13160 and the firing pin 13184 of the crimping drive 13180 both extend from the firing nut 13163. For the sake of expediency and demonstration, the firing pins 13172 and 13184 are illustrated as extending from the same side of the firing nut 13163; however, it is envisioned that the firing pin 13172 can extend from a first lateral side of the firing nut 13163 while the firing pin 13184 can extend from the other lateral side of the firing nut 13163. In such circumstances, the firing actuator 13168 can be positioned alongside the first lateral side of the drive screw 13161 and the crimping actuator 13188 can be positioned alongside the opposite lateral side of the drive screw 13161. Correspondingly, the longitudinal slot 13113 can be defined in a first lateral side of the shaft housing 13112 while the longitudinal slot 13115 can be defined in the opposite lateral side of the shaft housing 13112.

Further to the above, the cam actuator 13181 can be operably coupled with crimping actuator 13188 such that, when the crimping actuator 13188 is advanced distally by the firing nut 13163, the cam actuator 13181 can be advanced distally, as illustrated in FIG. 24, until the distal projection 13191*a* extending from the distal arm 13190*a* reaches the distal end 13117 of the longitudinal slot 13115. In such a distal position, the cam actuator 13181 may be in a fully advanced position and the clip 13140 positioned within the receiving chamber 13122 can be in a fully deformed or crimped configuration. Thereafter, the cam actuator 13181 can be retracted and the end effector 13120 can be reopened. More particularly, the drive screw 13161 can be rotated in an opposite direction in order to move the firing nut 13163 proximally and retract the cam actuator 13181 wherein, in certain instances, the end effector 13120 can further include a biasing member which can be configured to bias the first jaw 13123 and the second jaw 13123*b* from the closed, or fired, position illustrated in FIG. 20 into the open, or unfired, position illustrated in FIG. 19.

The embodiments disclosed herein are configured for use with surgical suturing instruments and systems such as those disclosed in U.S. patent application Ser. No. 16/112,168, filed on Aug. 24, 2018, now U.S. Patent Application Publication No. 2019/0125336, entitled SURGICAL SUTURING INSTRUMENT COMPRISING A NON-CIRCULAR NEEDLE, U.S. patent application Ser. No. 13/832,786, now U.S. Pat. No. 9,398,905, entitled CIRCULAR NEEDLE APPLIER WITH OFFSET NEEDLE AND CARRIER TRACKS; U.S. patent application Ser. No. 14/721,244, now U.S. Patent Application Publication No. 2016/0345958, entitled SURGICAL NEEDLE WITH RECESSED FEATURES; and U.S. patent application Ser. No. 14/740,724, now U.S. Patent Application Publication No. 2016/0367243, entitled SUTURING INSTRUMENT WITH MOTORIZED NEEDLE DRIVE, which are incorporated by reference in their entireties herein. The embodiments discussed herein are also usable with the instruments, systems, and methods disclosed in U.S. patent application Ser. No. 15/908,021, entitled SURGICAL INSTRUMENT WITH REMOTE RELEASE, filed on Feb. 28, 2018, U.S. patent application Ser. No. 15/908,012, entitled SURGICAL INSTRUMENT HAVING DUAL ROTATABLE MEMBERS TO EFFECT DIFFERENT TYPES OF END EFFECTOR MOVEMENT, filed on Feb. 28, 2018, U.S. patent application Ser. No. 15/908,040, entitled SURGICAL INSTRUMENT WITH ROTARY DRIVE SELECTIVELY ACTUATING MULTIPLE END EFFECTOR FUNCTIONS, filed on Feb. 28, 2018, U.S. patent application Ser. No. 15/908,057, entitled SURGICAL INSTRUMENT WITH ROTARY DRIVE SELECTIVELY ACTUATING MULTIPLE END EFFECTOR FUNCTIONS, filed on Feb. 28, 2018, U.S. patent application Ser. No. 15/908,058, entitled SURGICAL INSTRUMENT WITH MODULAR POWER SOURCES, filed on Feb. 28, 2018, and U.S. patent application Ser. No. 15/908,143, entitled SURGICAL INSTRUMENT WITH SENSOR AND/OR CONTROL SYSTEMS, filed on Feb. 28, 2018, which are incorporated in their entireties herein. Generally, these surgical suturing instruments comprise, among other things, a shaft, an end effector attached to the shaft, and drive systems positioned within the shaft to transfer motion from a source motion to the end effector. The motion source can comprise a manually driven actuator, an electric motor, and/or a robotic surgical system. The end effector comprises a body portion, a needle track defined within the body portion, and a needle driver configured to drive a needle through a rotational firing stroke. The needle is configured to be guided through its rotational firing stroke within the body portion by the needle track. In various instances, the needle driver is similar to that of a ratchet system. In at least one instance, the needle driver is configured to drive the needle through a first half of the rotational firing stroke which places the needle in a hand-off position—a position where a tissue-puncturing end of the needle has passed through the target tissue and reentered the body portion of the end effector. At such point, the needle driver can be returned to its original position to pick up the tissue-puncturing end of the needle and drive the needle through a second half of its rotational firing stroke. Once the needle driver pulls the needle through the second half of its rotational firing stroke, the needle driver is then returned to its original unfired position to grab the needle for another rotational firing stroke. The drive systems can be driven by one or more motors and/or manual drive actuation systems. The needle comprises suturing material, such as thread, for example, attached thereto. The suturing material is configured to be pulled through tissue as the needle is advanced through its rotational firing stroke to seal the tissue and/or attached the tissue to another structure, for example.

FIGS. 29-33 depict a surgical suturing instrument 94000 configured to suture the tissue of a patient. The surgical suturing instrument 94000 comprises a handle 94100, a shaft 94200 extending distally from the handle 94100, and an end effector 94300 attached to the shaft 94200 by way of an articulation joint 94210. The handle 94100 comprises a firing trigger 94110 configured to actuate a firing drive of the surgical suturing instrument 94000, a first rotational actuator 94120 configured to articulate the end effector 94300 about an articulation axis AA defined by the articulation joint 94210, and a second rotational actuator 94130 configured to rotate the end effector 94300 about a longitudinal axis LA defined by the end effector 94300. The surgical suturing instrument 94000 further comprises a flush port 94140. Examples of surgical suturing devices, systems, and methods are disclosed in U.S. patent application Ser. No. 13/832,786, now U.S. Pat. No. 9,398,905, entitled CIRCULAR NEEDLE APPLIER WITH OFFSET NEEDLE AND CARRIER TRACKS; U.S. patent application Ser. No. 14/721,244, now U.S. Patent Application Publication No. 2016/0345958, entitled SURGICAL NEEDLE WITH RECESSED FEATURES; and U.S. patent application Ser. No. 14/740,724, now U.S. Patent Application Publication No. 2016/0367243, entitled SUTURING INSTRUMENT WITH MOTORIZED NEEDLE DRIVE, which are incorporated by reference in their entireties herein.

Figure 34:
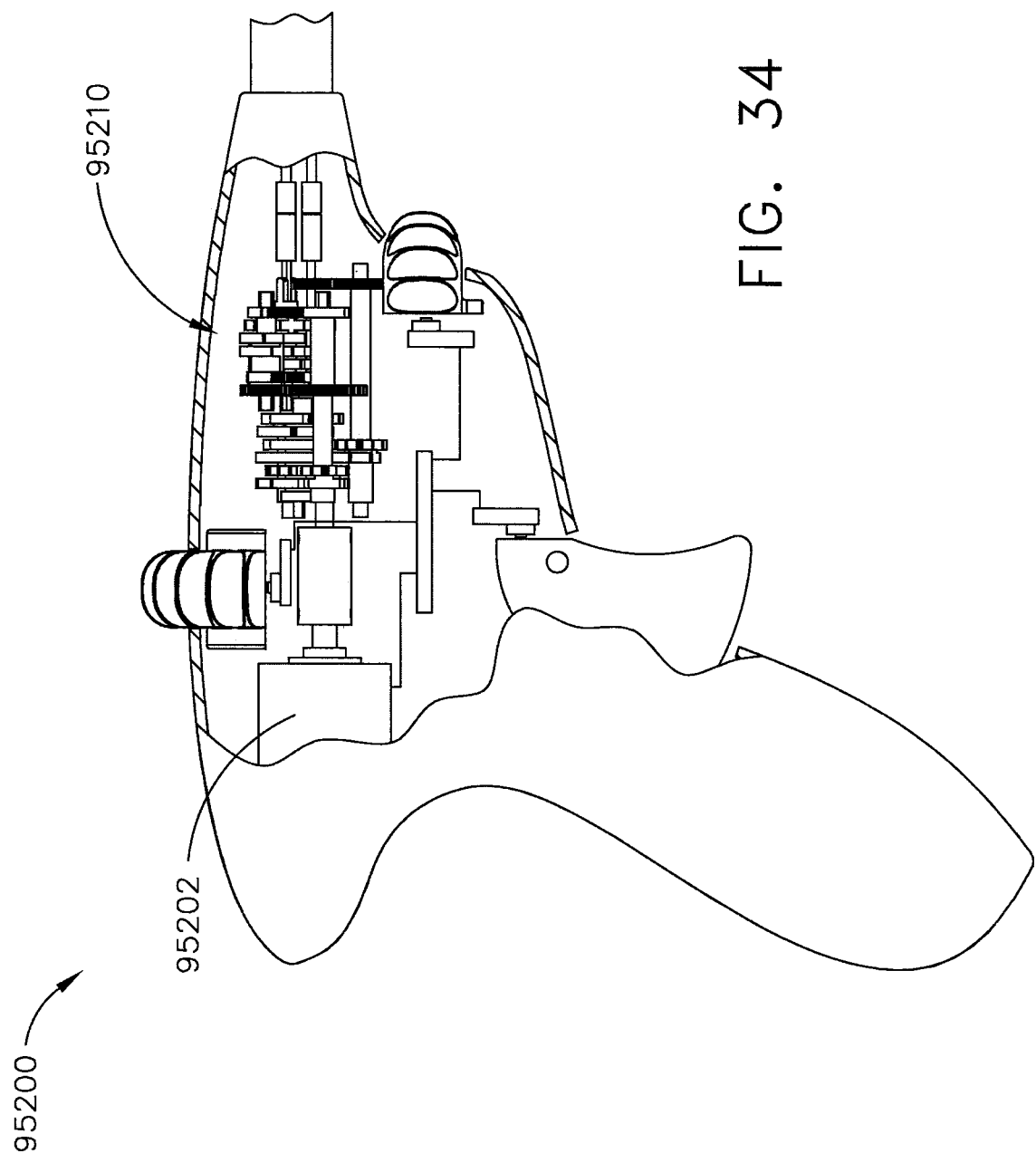
FIG. 34 is a perspective view of a surgical suturing instrument handle comprising a motor.

FIG. 34 depicts a handle assembly 95200 that is operable for use a surgical suturing instrument. The handle assembly 95200 is connected to a proximal end of a shaft. The handle assembly 95200 includes a motor 95202 and a transmission assembly 95210. The motor 95202 is configured to actuate a needle of a surgical suturing end effector by way of a needle driver, articulate the end effector, and rotate the end effector by way of the transmission assembly 95210. The transmission assembly 95210 is shifted between three states by a double acting solenoid, for example, so as to allow the motor 95202 to be used to actuate a needle of a surgical suturing end effector, articulate the end effector, and/or rotate the end effector. In at least one embodiment, the handle assembly 95200 could take the form of a robotic interface or a housing comprising gears, pulleys, and/or servomechanisms, for example. Such an arrangement could be used with a robotic surgical system.

Figure 35:
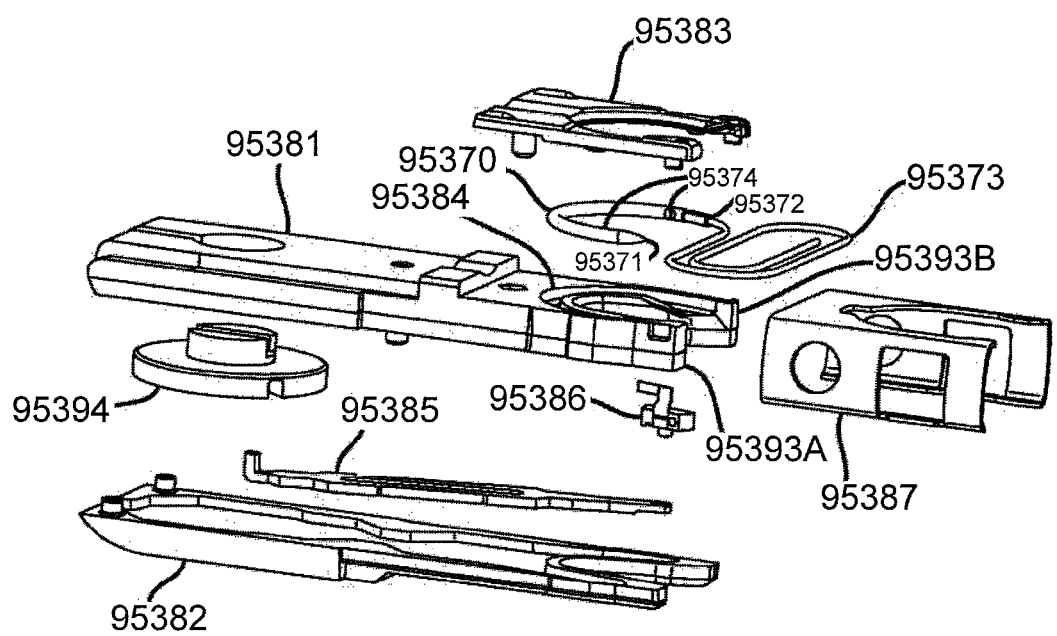
FIG. 35 is an exploded view of a suturing cartridge for use with a surgical suturing system.

FIG. 35 depicts a suturing cartridge 93590 comprising a lower body 93581, an upper body 93582, and a needle cover 93583. The cartridge 93590 further comprises a drive system comprising a needle driver 93586, a rotary input 93594, and a link 93585 connecting the needle driver 93586 and the rotary input 93594. The needle driver 93586, rotary input 93594, and link 93585 are captured between the lower body 93581 and the upper body 93582. The needle driver 93586, the link 93585, and the rotary input 93594 are configured to be actuated to drive a needle 93570 through a needle firing stroke by way of a motor-driven system, a manually-driven handheld system, and/or a robotic system, for example. The lower and upper bodies 93581, 93582 are attached to one another using any suitable technique, such as, for example, welds, pins, adhesives, and/or the like to form the cartridge body. The needle 93570 comprises a leading end 93571 configured to puncture tissue, a trailing end 93572, and a length of suture 93573 extending from and attached to the trailing end 93572. The needle 93570 is configured to rotate in a circular path defined by a needle track 93584. The needle track 93584 is defined in the cartridge body. The needle 93570 is configured to exit one of a first arm 95393A and a second arm 95393B of the cartridge body and enter the other of the first arm 95393A and the second arm 95393B during a needle firing stroke. Recessed features 93574 are provided to so that the needle driver 93586 can engage and drive the needle 93570 through the needle firing stroke in a ratchet-like motion. The needle 93570 is positioned between the needle track 93584 and the needle cover 93583. The suturing cartridge 93590 further comprises a cage 93587 that is configured to slide over the cartridge body to attach the needle cover 93583 to the lower body 93581.

Various aspects of the subject matter described herein are set out in the following examples.

Example Set 1

Example 1. A surgical device for applying clips, wherein the surgical device comprises an elongate shaft extending from a housing, an end effector extending from the elongate shaft, a cartridge, a crimping drive, an RFID tag comprising stored data, an RFID scanner configured to send an interrogation signal to the RFID tag and receive a first signal from the RFID tag in response to the interrogation signal, and a controller in communication with the RFID scanner. The end effector comprises a first jaw and a second jaw, wherein the first jaw and the second jaw are movable relative to each other between an open position and a closed position. The cartridge comprises a storage chamber and a plurality of clips removably positioned within the storage chamber. The crimping drive is configured to move the first jaw and the second jaw to the closed position during a crimping stroke, wherein one of the plurality of clips is crimped around tissue of a patient during the crimping stroke. The stored data on the RFID tag relates to an identifying characteristic of at least one of the plurality of clips within the cartridge. The first signal comprises the stored data on the RFID tag. The controller is configured to compare the stored data received by the RFID scanner to a set of compatibility data stored in a memory of the controller and vary an operational parameter of the surgical device based on the stored data received by the RFID scanner.

Example 2. The surgical device of Example 1, wherein the controller is further configured to permit the surgical device to perform the crimping stroke using the varied operational parameter when the controller determines the cartridge is compatible for use with the surgical device.

Example 3. The surgical device of Example 1 or 2, wherein the controller is further configured to prevent the surgical device from performing the crimping stroke when the controller is unable to recognize the cartridge as compatible for use with the surgical device.

Example 4. The surgical device of any one of Examples 1-3, wherein the controller is configured to vary the operational parameter of the surgical device based on the stored data received by the RFID scanner and the set of compatibility data stored in the memory.

Example 5. The surgical device of any one of Examples 1-4, wherein the stored data on the RFID tag comprises a number of clips contained within the cartridge.

Example 6. The surgical device of any one of Examples 1-5, wherein the stored data on the RFID tag comprises a type of material of which the plurality of clips within the cartridge are comprised.

Example 7. The surgical device of any one of Examples 1-6, wherein the stored data on the RFID tag comprises a size of the plurality of clips positioned within the cartridge.

Example 8. The surgical device of any one of Examples 1-7, wherein the operating parameter is a maximum load threshold.

Example 9. The surgical device of any one of Examples 1-7, wherein the operating parameter is a lockout load threshold, wherein the controller prevents the surgical device from performing the crimping stroke if the lockout load threshold is exceeded.

Example 10. The surgical device of any one of Examples 1-9, further comprising an electric motor and a power source, wherein the power source supplies power to the electric motor, and wherein the controller is configured to vary the power supplied to the electric motor based on the stored data received by the RFID scanner.

Example 11. The surgical device of any one of Examples 1-10, wherein the RFID tag is positioned on the cartridge.

Example 12. The surgical device of any one of Examples 1-10, wherein the RFID tag is positioned on one of the plurality of clips.

Example 13. The surgical device of Example 12, wherein the RFID tag is positioned on a portion of the clip that does not bend during the crimping stroke.

Example 14. A surgical device for applying clips, wherein the surgical device comprises an elongate shaft extending from a housing, an end effector extending from the elongate shaft, a clip comprising an RFID tag, a crimping drive, an RFID scanner, and a controller in communication with the RFID scanner. The end effector comprises a first jaw and a second jaw, wherein the first jaw is movable relative to the second jaw between an open position and a closed position. The RFID tag comprises stored data, wherein the stored data on the RFID tag is representative of the clip. The crimping drive is configured to move the first jaw and the second jaw to the closed position during a crimping stroke, wherein the clip is crimped around tissue of a patient during the crimping stroke. The RFID scanner is configured to receive the stored data on the RFID tag. The controller is configured to determine if the clip is compatible for use with the surgical device by comparing the stored data received by the RFID scanner to a set of compatibility data, permit the surgical device to perform a function when the controller determines the clip is compatible for use with the surgical device, and prevent the surgical device from performing the function when the controller determines the clip is incompatible for use with the surgical device.

Example 15. The surgical device of Example 14, wherein the controller determines the clip is incompatible for use with the surgical device when the stored data received by the RFID scanner is not found within the set of compatibility data.

Example 16. The surgical device of Examples 14 or 15, wherein the controller determines the clip is incompatible for use with the surgical device when the RFID scanner fails to receive the stored data the RFID tag.

Example 17. The surgical device of any one of Examples 14-16, further comprising an electric motor and a power source, wherein the power source is configured to supply power to the electric motor, and wherein the controller is configured to vary an operating condition of the electric motor based on the stored data received from the RFID tag.

Example 18. The surgical device of any one of Examples 14-17, wherein the RFID tag is positioned on a portion of the clip that is not bent during the crimping stroke.

Example 19. The surgical device of any one of Examples 14-17, wherein the clip comprises an inner surface and an outer surface, wherein the inner surface is in contact with the tissue of the patient after the crimping stroke, and wherein the RFID tag is positioned on the outer surface of the clip.

Example 20. A surgical device for applying clips, wherein the surgical device comprises an elongate shaft extending from a housing, an end effector extending from the elongate shaft, a cartridge, a crimping drive, an RFID tag comprising stored data, an RFID scanner configured to communicate with the RFID tag, and a controller in communication with the RFID scanner. The end effector comprises a first jaw and a second jaw, wherein the first jaw and the second jaw are movable relative to each other between an open position and a closed position. The cartridge comprises a storage chamber and a plurality of clips removably positioned within the storage chamber. The crimping drive is configured to move the first jaw and the second jaw to the closed position during a crimping stroke, wherein one of the plurality of clips is crimped around tissue of a patient during the crimping stroke. The stored data on the RFID tag relates to an identifying characteristic of the plurality of clips within the cartridge. The RFID scanner is configured to receive the stored data from the RFID tag. The controller is configured to compare the stored data received by the RFID scanner to a set of authenticity data, permit the surgical device to perform the crimping stroke when the controller determines that the plurality of clips are authentic, and prevent the surgical device from performing the crimping stroke when the controller determines that the plurality of clips are inauthentic.

Example Set 2

Example 1. A surgical suturing system comprising an elongate shaft, a firing drive, an end effector extending distally from the elongate shaft, wherein the end effector comprises a needle track and a replaceable needle guided by the needle track and actuated by the firing drive through a firing stroke, wherein the replaceable needle comprises suturing material attached thereto and an RFID tag comprising stored data. The surgical suturing system further comprises an RFID scanner, wherein the RFID scanner receives a signal from the RFID tag comprising the stored data, and wherein the signal is indicative of the stored data. The surgical suturing system further comprises a controller in communication with the RFID scanner, wherein the controller is configured to determine compatibility between the replaceable needle and the surgical suturing system based on the stored data received by the RFID scanner and prevent the surgical suturing system from performing the firing stroke when the replaceable needle is incompatible with the surgical suturing system.

Example 2. The surgical suturing system of Example 1, wherein the controller is further configured to prevent the surgical suturing system from performing the firing stroke when the RFID scanner fails to receive the signal from the RFID tag.

Example 3. The surgical suturing system of Examples 1 or 2, wherein the RFID scanner comprises reading capabilities and writing capabilities.

Example 4. The surgical suturing system of any one of Examples 1-3, wherein the RFID tag is positioned on the replaceable needle.

Example 5. The surgical suturing system of any one of Examples 1-3, wherein the RFID tag is positioned on the suturing material.

Example 6. The surgical suturing system of any one of Examples 1-5, wherein the RFID tag comprises an integrated battery.

Example 7. The surgical suturing system of Example 6, wherein the replaceable needle is stored in a packaging prior to being attached to the surgical suturing system, wherein the packaging comprises a first layer and a second layer, wherein the first layer and the second layer form a seal around the replaceable needle, and wherein the RFID tag is positioned on the packaging.

Example 8. The surgical suturing system of Example 7, further comprising an insulator attached to the second layer which electrically decouples the integrated battery from the RFID tag, wherein the RFID tag is attached to the first layer of the packaging, wherein the insulator detaches from the integrated battery when the first layer is removed from the second layer, and wherein the RFID tag becomes active and transmits the stored data when the insulator is detached from the integrated battery.

Example 9. A surgical device for applying clips, wherein the surgical device comprises an elongate shaft extending from a housing, an end effector extending from the elongate shaft, a cartridge, a crimping drive, an RFID tag comprising a first set of information, an RFID scanner configured to receive a first signal from the RFID tag, and a controller in communication with the RFID scanner. The end effector comprises a first jaw and a second jaw, wherein the first jaw and the second jaw are movable relative to each other between an open position and a closed position. The cartridge comprises a storage chamber and a plurality of clips removably positioned within the storage chamber. The crimping drive is configured to move the first jaw and the second jaw to the closed position during a crimping stroke, wherein one of the plurality of clips is crimped around tissue of a patient during the crimping stroke. The first set of information corresponds to the cartridge. The first signal comprises the first set of information. The controller is configured to determine if the cartridge is compatible with the surgical device by comparing the first set of information received by the RFID scanner to a set of compatibility data stored in a memory of the controller, permit the surgical device to perform the crimping stroke when the controller determines the cartridge is compatible for use with the surgical device, prevent the surgical device from performing the crimping stroke when the controller is unable to recognize the cartridge as compatible for use with the surgical device, and prevent the surgical device from performing the crimping stroke when the RFID scanner does not receive the first signal.

Example 10. The surgical device of Example 9, wherein the RFID tag is positioned on the cartridge.

Example 11. The surgical device of Example 9, wherein the RFID tag is positioned on a first clip from the plurality of clips and a second RFID tag is positioned on a second clip from the plurality of clips, and wherein the second RFID tag comprises a second set of information.

Example 12. The surgical device of Example 11, wherein the controller is configured to prevent the crimping stroke when the RFID scanner receives the first signal from the RFID tag and a second signal from the second RFID tag.

Example 13. The surgical device of Example 11, wherein the RFID scanner comprises a communication range, wherein the RFID scanner can only communicate with RFID tags positioned within the communication range, and wherein the controller is configured to prevent the crimping stroke if the RFID scanner receives signals from more than one RFID tag.

Example 14. The surgical device of any one of Examples 9-13, further comprising an electric motor and a power source, wherein the power source is configured to supply power to the electric motor, and wherein the controller is configured to vary an operating parameter of the electric motor based on the first set of information received by the RFID scanner.

Example 15. A surgical stapling system comprising a surgical instrument, a replaceable component assembly, an RFID scanner comprising a communication range, and a controller in communication with the RFID scanner. The surgical instrument comprises an elongate shaft, an end effector extending from the elongate shaft, wherein the end effector comprises a first jaw and a second jaw, and a staple cartridge replaceably seated in the second jaw, wherein the staple cartridge comprises a cartridge body comprising a cartridge deck and staples removably positioned in the cartridge body. The replaceable component assembly comprises a mounting member, a replaceable component configured to be positioned on the cartridge deck of the staple cartridge, wherein the replaceable component is supported on the mounting member as the replaceable component is being attached to the cartridge deck, and an RFID tag comprising a first set of data. The RFID scanner is configured to transmit a first signal to the RFID tag and receive a second signal from the RFID tag as the replaceable component is brought within the communication range, wherein the second signal comprises the first set of data. The controller comprises a memory comprising a second set of data, wherein the controller is configured to determine if the replaceable component is compatible with the surgical instrument by comparing the first set of data received by the RFID scanner to the second set of data stored in the memory of the controller, permit the surgical instrument to perform a function when the controller determines the replaceable component is compatible for use with the surgical instrument, prevent the surgical instrument from performing the function when the controller is unable to recognize the replaceable component as compatible for use with the surgical instrument, and prevent the surgical instrument from performing the function when the RFID scanner does not receive the second signal in response to the first signal.

Example 16. The surgical stapling system of Example 15, wherein the mounting member comprises a back wall, wherein the RFID tag is positioned on the back wall, and wherein the RFID scanner is positioned on a distal end of the end effector.

Example 17. The surgical stapling system of Example 16, wherein the RFID tag is in the communication range of the RFID scanner when the end effector and the replaceable component are aligned.

Example 18. The surgical stapling system of any one of Examples 15-17, wherein the function comprises a staple firing stroke.

Example 19. The surgical stapling system of any one of Examples 15-18, wherein the replaceable component comprises a tissue thickness compensator.

Example 20. The surgical stapling system of any one of Examples 15-19, further comprising an electric motor and a power source configured to supply power to the electric motor, wherein the controller is configured to vary an operating parameter of the electric motor based on the first set of data received by the RFID scanner.

While several forms have been illustrated and described, it is not the intention of the applicant to restrict or limit the scope of the appended claims to such detail. Numerous modifications, variations, changes, substitutions, combinations, and equivalents to those forms may be implemented and will occur to those skilled in the art without departing from the scope of the present disclosure. Moreover, the structure of each element associated with the described forms can be alternatively described as a means for providing the function performed by the element. Also, where materials are disclosed for certain components, other materials may be used. It is therefore to be understood that the foregoing description and the appended claims are intended to cover all such modifications, combinations, and variations as falling within the scope of the disclosed forms. The appended claims are intended to cover all such modifications, variations, changes, substitutions, modifications, and equivalents.

The foregoing detailed description has set forth various forms of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, and/or examples can be implemented, individually and/or collectively, by a wide range of hardware, software, firmware, or virtually any combination thereof. Those skilled in the art will recognize that some aspects of the forms disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as one or more program products in a variety of forms, and that an illustrative form of the subject matter described herein applies regardless of the particular type of signal bearing medium used to actually carry out the distribution.

Instructions used to program logic to perform various disclosed aspects can be stored within a memory in the system, such as dynamic random access memory (DRAM), cache, flash memory, or other storage. Furthermore, the instructions can be distributed via a network or by way of other computer readable media. Thus a machine-readable medium may include any mechanism for storing or transmitting information in a form readable by a machine (e.g., a computer), but is not limited to, floppy diskettes, optical disks, compact disc, read-only memory (CD-ROMs), and magneto-optical disks, read-only memory (ROMs), random access memory (RAM), erasable programmable read-only memory (EPROM), electrically erasable programmable read-only memory (EEPROM), magnetic or optical cards, flash memory, or a tangible, machine-readable storage used in the transmission of information over the Internet via electrical, optical, acoustical or other forms of propagated signals (e.g., carrier waves, infrared signals, digital signals, etc.). Accordingly, the non-transitory computer-readable medium includes any type of tangible machine-readable medium suitable for storing or transmitting electronic instructions or information in a form readable by a machine (e.g., a computer).

As used in any aspect herein, the term "control circuit" may refer to, for example, hardwired circuitry, programmable circuitry (e.g., a computer processor comprising one or more individual instruction processing cores, processing unit, processor, microcontroller, microcontroller unit, controller, digital signal processor (DSP), programmable logic device (PLD), programmable logic array (PLA), or field programmable gate array (FPGA)), state machine circuitry, firmware that stores instructions executed by programmable circuitry, and any combination thereof. The control circuit may, collectively or individually, be embodied as circuitry that forms part of a larger system, for example, an integrated circuit (IC), an application-specific integrated circuit (ASIC), a system on-chip (SoC), desktop computers, laptop computers, tablet computers, servers, smart phones, etc. Accordingly, as used herein "control circuit" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

As used in any aspect herein, the term "logic" may refer to an app, software, firmware and/or circuitry configured to perform any of the aforementioned operations. Software may be embodied as a software package, code, instructions, instruction sets and/or data recorded on non-transitory computer readable storage medium. Firmware may be embodied as code, instructions or instruction sets and/or data that are hard-coded (e.g., nonvolatile) in memory devices.

As used in any aspect herein, the terms "component," "system," "module" and the like can refer to a computer-related entity, either hardware, a combination of hardware and software, software, or software in execution.

As used in any aspect herein, an "algorithm" refers to a self-consistent sequence of steps leading to a desired result, where a "step" refers to a manipulation of physical quantities and/or logic states which may, though need not necessarily, take the form of electrical or magnetic signals capable of being stored, transferred, combined, compared, and otherwise manipulated. It is common usage to refer to these signals as bits, values, elements, symbols, characters, terms, numbers, or the like. These and similar terms may be associated with the appropriate physical quantities and are merely convenient labels applied to these quantities and/or states.

A network may include a packet switched network. The communication devices may be capable of communicating with each other using a selected packet switched network communications protocol. One example communications protocol may include an Ethernet communications protocol which may be capable permitting communication using a Transmission Control Protocol/Internet Protocol (TCP/IP). The Ethernet protocol may comply or be compatible with the Ethernet standard published by the Institute of Electrical and Electronics Engineers (IEEE) titled "IEEE 802.3 Standard", published in December, 2008 and/or later versions of this standard. Alternatively or additionally, the communication devices may be capable of communicating with each other using an X.25 communications protocol. The X.25 communications protocol may comply or be compatible with a standard promulgated by the International Telecommunication Union-Telecommunication Standardization Sector (ITU-T). Alternatively or additionally, the communication devices may be capable of communicating with each other using a frame relay communications protocol. The frame relay communications protocol may comply or be compatible with a standard promulgated by Consultative Committee for International Telegraph and Telephone (CCITT) and/or the American National Standards Institute (ANSI). Alternatively or additionally, the transceivers may be capable of communicating with each other using an Asynchronous Transfer Mode (ATM) communications protocol. The ATM communications protocol may comply or be compatible with an ATM standard published by the ATM Forum titled "ATM-MPLS Network Interworking 2.0" published August 2001, and/or later versions of this standard. Of course, different and/or after-developed connection-oriented network communication protocols are equally contemplated herein.

In various aspects, a microcontroller of control circuit in accordance with the present disclosure may be any single-core or multicore processor such as those known under the trade name ARM Cortex by Texas Instruments. In one aspect, the main microcontroller 461 may be an LM4F230H5QR ARM Cortex-M4F Processor Core, available from Texas Instruments, for example, comprising an on-chip memory of 256 KB single-cycle flash memory, or other non-volatile memory, up to 40 MHz, a prefetch buffer to improve performance above 40 MHz, a 32 KB single-cycle SRAM, and internal ROM loaded with StellarisWare® software, a 2 KB EEPROM, one or more PWM modules, one or more QEI analogs, and/or one or more 12-bit ADCs with 12 analog input channels, details of which are available for the product datasheet.

Unless specifically stated otherwise as apparent from the foregoing disclosure, it is appreciated that, throughout the foregoing disclosure, discussions using terms such as "processing," "computing," "calculating," "determining," "displaying," or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

One or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

The terms "proximal" and "distal" are used herein with reference to a clinician manipulating the housing portion of the surgical instrument. The term "proximal" refers to the portion closest to the clinician and the term "distal" refers to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Those skilled in the art will recognize that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flow diagrams are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

It is worthy to note that any reference to "one aspect," "an aspect," "an exemplification," "one exemplification," and the like means that a particular feature, structure, or characteristic described in connection with the aspect is included in at least one aspect. Thus, appearances of the phrases "in one aspect," "in an aspect," "in an exemplification," and "in one exemplification" in various places throughout the specification are not necessarily all referring to the same aspect. Furthermore, the particular features, structures or characteristics may be combined in any suitable manner in one or more aspects.

Any patent application, patent, non-patent publication, or other disclosure material referred to in this specification and/or listed in any Application Data Sheet is incorporated by reference herein, to the extent that the incorporated materials is not inconsistent herewith. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

In summary, numerous benefits have been described which result from employing the concepts described herein. The foregoing description of the one or more forms has been presented for purposes of illustration and description. It is not intended to be exhaustive or limiting to the precise form disclosed. Modifications or variations are possible in light of the above teachings. The one or more forms were chosen and described in order to illustrate principles and practical application to thereby enable one of ordinary skill in the art to utilize the various forms and with various modifications as are suited to the particular use contemplated. It is intended that the claims submitted herewith define the overall scope.

What is claimed is:

1. A surgical device for applying clips, wherein said surgical device comprises:
   an elongate shaft extending from a housing;
   an end effector extending from said elongate shaft, wherein said end effector comprises:
   a first jaw; and a second jaw, wherein said first jaw and said second jaw are movable relative to each other between an open position and a closed position;
a cartridge, comprising:
a storage chamber; and
a plurality of clips removably positioned within said storage chamber, wherein said plurality of clips comprises a first clip;
a crimping drive configured to move said first jaw and said second jaw to said closed position during a crimping stroke, wherein one of said plurality of clips is crimped around tissue of a patient during the crimping stroke;
an RFID tag positioned on said first clip, wherein said RFID tag comprises stored data, wherein said stored data on said RFID tag relates to an identifying characteristic of said first clip;
an RFID scanner configured to send an interrogation signal to said RFID tag and receive a first signal from said RFID tag in response to said interrogation signal, wherein said first signal comprises said stored data on said RFID tag; and
a controller in communication with said RFID scanner, wherein said controller is configured to:
compare said stored data received by said RFID scanner to a set of compatibility data stored in a memory of said controller; and
vary an operational parameter of said surgical device based on said stored data received by said RFID scanner.

2. The surgical device of claim 1, wherein said controller is further configured to permit said surgical device to perform the crimping stroke on said first clip using said varied operational parameter when said controller determines said first clip is compatible for use with said surgical device.

3. The surgical device of claim 1, wherein said controller is further configured to prevent said surgical device from performing the crimping stroke on said first clip when said controller is unable to recognize said first clip as compatible for use with said surgical device.

4. The surgical device of claim 1, wherein said controller is configured to vary said operational parameter of said surgical device based on said stored data received by said RFID scanner and said set of compatibility data stored in said memory.

5. The surgical device of claim 1, wherein said stored data on said RFID tag comprises a type of material of which said first clip is comprised.

6. The surgical device of claim 1, wherein said stored data on said RFID tag comprises a size of said first clip.

7. The surgical device of claim 1, wherein said operational parameter is a maximum load threshold.

8. The surgical device of claim 1, wherein said operational parameter is a lockout load threshold, and wherein said controller prevents said surgical device from performing the crimping stroke on said first clip if said lockout load threshold is exceeded.

9. The surgical device of claim 1, further comprising an electric motor and a power source, wherein said power source supplies power to said electric motor, and wherein said controller is configured to vary said power supplied to said electric motor based on said stored data received by said RFID scanner.

10. The surgical device of claim 1, wherein said RFID tag is positioned on a portion of said first clip that does not bend during the crimping stroke.

11. The surgical device of claim 1, wherein said RFID tag is a first RFID tag, wherein said plurality of clips further comprises a second clip, and wherein said surgical device further comprises a second RFID tag positioned on said second clip.

12. The surgical device of claim 1, wherein said RFID tag is a first RFID tag, wherein said cartridge further comprises a second RFID tag comprising second stored data.

13. The surgical device of claim 12, wherein said controller is further configured to maintain a count of the number of clips remaining in the cartridge.

14. A surgical device for applying clips, wherein said surgical device comprises:
an elongate shaft extending from a housing;
an end effector extending from said elongate shaft, wherein said end effector comprises:
a first jaw; and
a second jaw, wherein said first jaw is movable relative to said second jaw between an open position and a closed position;
a clip comprising an RFID tag, wherein said RFID tag is positioned on a portion of said clip, wherein said RFID tag comprises stored data, and wherein said stored data on said RFID tag is representative of said clip;
a crimping drive configured to move said first jaw and said second jaw to said closed position during a crimping stroke, wherein said clip is crimped around tissue of a patient during the crimping stroke;
an RFID scanner configured to receive said stored data on said RFID tag; and
a controller in communication with said RFID scanner, wherein said controller is configured to:
determine if said clip is compatible for use with said surgical device by comparing said stored data received by said RFID scanner to a set of compatibility data;
permit said surgical device to perform a function when said controller determines said clip is compatible for use with said surgical device; and
prevent said surgical device from performing said function when said controller determines said clip is incompatible for use with said surgical device.

15. The surgical device of claim 14, wherein said controller determines said clip is incompatible for use with said surgical device when said stored data received by said RFID scanner is not found within said set of compatibility data.

16. The surgical device of claim 14, wherein said controller determines said clip is incompatible for use with said surgical device when said RFID scanner fails to receive said stored data said RFID tag.

17. The surgical device of claim 14, further comprising an electric motor and a power source, wherein said power source is configured to supply power to said electric motor, and wherein said controller is configured to vary an operating condition of said electric motor based on said stored data received from said RFID tag.

18. The surgical device of claim 14, wherein said RFID tag is positioned on a portion of said clip that is not bent during the crimping stroke.

19. The surgical device of claim 14, wherein said clip comprises an inner surface and an outer surface, wherein said inner surface is in contact with the tissue of the patient after the crimping stroke, and wherein said RFID tag is positioned on said outer surface of said clip.

20. A surgical device for applying clips, wherein said surgical device comprises:
an elongate shaft extending from a housing;

an end effector extending from said elongate shaft, wherein said end effector comprises:
- a first jaw; and
- a second jaw, wherein said first jaw and said second jaw are movable relative to each other between an open position and a closed position;

a cartridge, comprising:
- a storage chamber; and
- a plurality of clips removably positioned within said storage chamber, wherein said plurality of clips comprises a first clip;

a crimping drive configured to move said first jaw and said second jaw to said closed position during a crimping stroke, wherein one of said plurality of clips is crimped around tissue of a patient during the crimping stroke;

an RFID tag positioned on said first clip, wherein said RFID tag comprises stored data, wherein said stored data on said RFID tag relates to an identifying characteristic of said first clip;

an RFID scanner configured to communicate with said RFID tag, wherein said RFID scanner is configured to receive said stored data from said RFID tag; and a controller in communication with said RFID scanner, wherein said controller is configured to:
- compare said stored data received by said RFID scanner to a set of authenticity data;
- permit said surgical device to perform the crimping stroke on said first clip when said controller determines that said first clip is authentic; and
- prevent said surgical device from performing the crimping stroke on said first clip when said controller determines that said first clip is inauthentic.

21. A surgical device for applying clips, wherein the surgical device comprises:
a shaft;
an end effector extending from the shaft, wherein the end effector comprises:
- a first jaw; and
- a second jaw, wherein the first jaw is movable relative to the second jaw between an open position and a closed position;

a clip comprising an RFID tag with stored data representative of the clip;

a crimping drive configured to transition the end effector to the closed position during a crimping stroke for crimping a tissue of a patient by the clip;

an RFID scanner configured to receive the stored data from the RFID tag; and a controller configured to:
- determine a usage compatibility of the clip with the surgical device by comparing stored date; and
- select between permitting the surgical device to perform a function and preventing the surgical device from performing the function based on the determined usage compatibility.

22. A surgical device for applying clips, wherein the surgical device comprises:
a shaft;
an end effector extending from the shaft, wherein the end effector comprises:
- a first jaw; and
- a second jaw, wherein the first jaw is movable relative to the second jaw between an open position and a closed position;

a clip comprising an RFID tag with stored data representative of the clip;

a crimping drive configured to transition the end effector to the closed position during a crimping stroke for crimping a tissue of a patient by the clip;

an RFID scanner configured to receive the stored data from the RFID tag; and a controller configured to:
- compare the stored data received by the RFID scanner to compatibility data; and
- adjust an operational parameter of the surgical device based on the stored data.

* * * * *